United States Patent [19]
Petrie et al.

[11] Patent Number: 5,965,573
[45] Date of Patent: Oct. 12, 1999

[54] COMPOSITIONS AND METHODS FOR TREATING BONE DEFICIT CONDITIONS

[75] Inventors: Charles Petrie, Woodinville; Mark W. Orme, Seattle; Nand Baindur, Edmonds; Kirk G. Robbins, Renton; Maria Kontoyianni, Seattle, all of Wash.; Gregory R. Mundy, San Antonio, Tex.

[73] Assignees: Zymogenetics, Inc., Seattle, Wash.; Osteoscreen, Inc., San Antonio, Tex.

[21] Appl. No.: 08/812,141

[22] Filed: Mar. 6, 1997

Related U.S. Application Data

[63] Continuation of application No. 08/735,874, Oct. 23, 1996, abandoned.

[51] Int. Cl.$^6$ .................. A61K 31/33; A61K 31/445; A61K 31/495; A61K 31/40
[52] U.S. Cl. .................. 514/316; 514/183; 514/247; 514/255; 514/256; 514/272; 514/351; 514/187; 514/275; 514/277; 514/299; 514/329; 514/330; 514/349; 514/350; 514/317; 514/357; 514/422
[58] Field of Search .................. 514/183, 247, 514/255, 256, 272, 316, 351, 187, 275, 277, 299, 329, 330, 349, 350, 317, 357, 422

[56] References Cited

U.S. PATENT DOCUMENTS

| | | | |
|---|---|---|---|
| 5,280,040 | 1/1994 | Labroo et al. | 514/422 |
| 5,441,964 | 8/1995 | Bryant et al. | 514/324 |
| 5,523,309 | 6/1996 | Bryant et al. | 514/320 |
| 5,622,974 | 4/1997 | Muehl | 514/320 |

FOREIGN PATENT DOCUMENTS

| | | |
|---|---|---|
| WO93/10113 A1 | 5/1993 | WIPO . |
| WO95/10513 A1 | 4/1995 | WIPO . |

OTHER PUBLICATIONS

Chem. abstr. vol. 127, abstract No. 127:17703, Petrie et al. Preparation of (hetero aromatic compounds for treating bone deficit conditions, WO–97/15308 (Eng.).
Chem abstr. vol. 107, abst. No. 107:109578, Watts et al., Studies on the ligand specificity and potential identify of microsomal antiestrogen–binding sites, Mol. Pharmocol. 1987, 31(5), 541–51.
Chem abstr. vol. 108, abstract No. 108:69162, Jordan et al., Effects of antiestrogens on bone in castrated and intact female rats, Breast Cancer Res. Treat. 1987, 10(1), 31–5.
Chem. abstr. vol. 115, abstract No. 115:8533, Schwarz et al. 1,2–diphenyl–1–pyridybut–1–enes–potential antigestrogens. part 1. synthesis Arch. Pharm. 1991, 324(4), 223–9.
Neelam et al. Structure–activity relationship of antiestrogens: A study using triarylbutenone, benzofuran and triayrlfuran analogues as models for triarylethylenes and triarylpropenones. J. Med. chem. 1989, vol. 32, pp. 1700–1707, see entire article.
Von Angerer et al. Studies on heterocycle–based pure estrogen antagonists. Ann. N.Y. Academy Sciences. 1995, vol. 761, pp. 176–191, see especially pp. 178–180.
Mundy, G.R., "Cytokines and Growth Factors in the Regulation of Bone Remodeling," *Journal of Bone and Mineral Research* (1993) 8(2):S505–S510.
Mundy, G.R., "Regulation of Bone Formation by Bone Morphogenetic Proteins and Other Growth Factors," *Clinical Orthopaedics and Related Research* (1996) 324:24–28.
Harris, S.E., et al., "Effects of Transforming Growth Factor β on Bone Nodule Formation and Expression of Bone Morphogenetic Protein 2, Osteocalcin, Osteopontin, Alkaline Phosphatase, and Type I Collagen mRNA in Long–Term Cultures of Fetal Rat Calvarial Osteoblasts," *Journal of Bone and Mineral Research* (1994) 9(6):855–863.
Stein, G.S., et al., "Bone cell differentiation: a functionally coupled relationship between expression of cell–growth– and tissue–specific genes," *Current Opinion in Cell Biology* (1990) 2:1018–1027.
Urist, M.R., "Bone: Formation by Autoinduction," *Science* (1965) 150:893–899.
Wozney, J.M., et al., "Novel Regulators of Bone Formation: Molecular Clones and Activities," *Science* (1988) 242:1528–1534.
Wozney, J.M., "The Bone Morphogenetic Protein Family and Osteogenesis," *Molecular Reproduction and Development* (1992) 32:160–167.

*Primary Examiner*—Theodore J. Criares
*Attorney, Agent, or Firm*—Morrison & Foerster LLP

[57] ABSTRACT

Compounds containing two aromatic systems covalently linked through a linker containing one or more atoms, or "linker" defined as including a covalent bond per se so as to space the aromatic systems at a distance 1.5–15 Å, are effective in treating conditions associated with bone deficits. The compounds can be administered to vertebrate subjects alone or in combination with additional agents that promote bone growth or that inhibit bone resorption. They can be screened for activity prior to administration by assessing their ability to effect the transcription of a reporter gene coupled to a promoter associated with a bone morphogenetic protein and/or their ability to stimulate calvarial growth in model animal systems.

15 Claims, 91 Drawing Sheets

| At least 1N $Ar^1$-linker - $Ar^2$ 1.5-15Å | | (I) |
|---|---|---|
| $Ar^1$ | $Ar^2$ | |
| contains 5-membered heterocycle | substituted or unsubsituted benzene | II-A |
| contains 5-membered heterocycle | substituted or unsubstituted naphthalene | II-B |
| contains 5-membered heterocycle | contains 6-membered heterocycle | II-C |
| contains 5-membered heterocycle | contains 5-membered heterocycle | II-D |
| contains 6-membered heterocycle | substituted or unsubstituted benzene | II-E |
| contains 6-membered heterocycle | substituted or unsubstituted naphthalene | II-F |
| contains 6-membered heterocycle | contains 6-membered heterocycle | II-G |
| substituted or unsubstituted naphthalene | substituted or unsubstituted benzene | II-H |
| substituted or unsubstituted naphthalene | substituted or unsubstituted naphthalene | II-I |
| substituted or unsubstituted benzene | substituted or unsubstituted benzene | II-J |

FIG. 1

| NNC# | MOL.WEIGHT | CONCENTRATION | | %RESPONSE | |
|---|---|---|---|---|---|
| 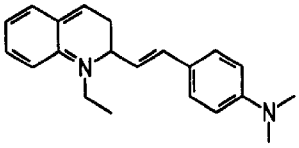 50-0194 | 430.33 | | | | |
| 50-0194 | | 100.00 | uM | -19.190 | |
| | | 31.25 | uM | 32.450 | |
| | | 9.77 | uM | -14.240 | |
| | | 3.05 | uM | -11.330 | |
| | | 953.67 | nM | -12.790 | |
| | | 298.02 | nM | -13.450 | |
| | | 93.13 | nM | -12.290 | |
| | | 29.10 | nM | -9.440 | |
| | | 9.09 | nM | -6.450 | |
| | | 2.84 | nM | -8.130 | |
| | | 888.18 | pM | -3.320 | |
| 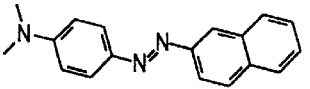 50-0195 | 275.36 | | | | |
| 50-0195 | | 100.00 | uM | -4.630 | |
| | | 31.25 | uM | 16.790 | |
| | | 9.77 | uM | 62.830 | |
| | | 3.05 | uM | 102.720 | |
| | | 953.67 | nM | 60.860 | |
| | | 298.02 | nM | 32.450 | |
| | | 93.13 | nM | 19.340 | |
| | | 29.10 | nM | 17.220 | |
| | | 9.09 | nM | 5.640 | |
| | | 2.84 | nM | 4.840 | |
| | | 888.18 | pM | 5.640 | |
| 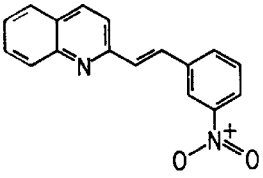 50-0196 | 276.30 | | | | |
| 50-0196 | | 100.00 | uM | -16.210 | |
| | | 31.25 | uM | -8.560 | |
| | | 9.77 | uM | 11.620 | |
| | | 3.05 | uM | 27.790 | |
| | | 953.67 | nM | 18.390 | |
| | | 298.02 | nM | 6.230 | |
| | | 93.13 | nM | 12.420 | |
| | | 29.10 | nM | 12.630 | |
| | | 9.09 | nM | 6.590 | |
| | | 2.84 | nM | 7.970 | |
| | | 888.18 | pM | 5.060 | |
FIG. 3A

| Structure | ID | MW | Conc | Unit | Value | |
|---|---|---|---|---|---|---|
| 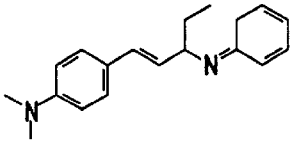 | 50-0197 | 274.37 | | | | |
| | 50-0197 | | 100.00 | uM | -18.250 | |
| | | | 31.25 | uM | -14.980 | |
| | | | 9.77 | uM | 4.040 | |
| | | | 3.05 | uM | 93.790 | |
| | | | 953.67 | nM | 205.530 | |
| | | | 298.02 | nM | 242.920 | |
| | | | 93.13 | nM | 195.890 | |
| | | | 29.10 | nM | 115.320 | |
| | | | 9.09 | nM | 85.630 | |
| | | | 2.84 | nM | 54.380 | |
| | | | 888.18 | pM | 33.180 | |
| 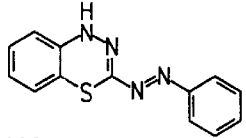 | 59-0008 | 254.32 | | | | |
| 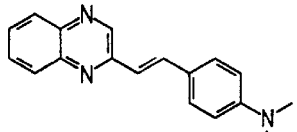 | 59-0019 | | | | | |
| | 59-0019 | | 100.00 | uM | -22.240 | |
| | | | 31.25 | uM | -22.670 | |
| | | | 9.77 | uM | -17.470 | |
| | | | 3.05 | uM | 74.490 | |
| | | | 953.67 | nM | 198.080 | |
| | | | 298.02 | nM | 258.340 | |
| | | | 93.13 | nM | 225.350 | |
| | | | 29.10 | nM | 75.220 | |
| | | | 9.09 | nM | 24.030 | |
| | | | 2.84 | nM | 34.480 | |
| | | | 888.18 | pM | -3.740 | |
| 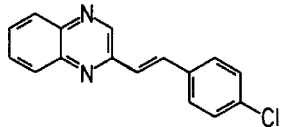 | 59-0020 | 266.73 | | | | |
| | 59-0020 | | 100.00 | uM | -16.510 | |
| | | | 31.25 | uM | -16.040 | |
| | | | 9.77 | uM | -0.270 | |
| | | | 3.05 | uM | 96.490 | |
| | | | 953.67 | nM | 153.320 | |
| | | | 298.02 | nM | 110.240 | |
| | | | 93.13 | nM | 60.030 | |
FIG. 3B

| | | 29.10 | nM | 37.870 | |
|---|---|---|---|---|---|
| | | 9.09 | nM | 24.820 | |
| | | 2.84 | nM | 20.500 | |
| | | 888.18 | pM | 13.310 | |

FIG. 3C

| | | | | | |
|---|---|---|---|---|---|
| 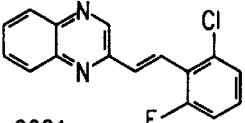 59-0021 | 284.72 | | | | |
| 59-0021 | | 100.00 | uM | -16.310 | |
| | | 31.25 | uM | -12.850 | |
| | | 9.77 | uM | 84.130 | |
| | | 3.05 | uM | 89.940 | |
| | | 953.67 | nM | 65.750 | |
| | | 298.02 | nM | 33.940 | |
| | | 93.13 | nM | 22.560 | |
| | | 29.10 | nM | 25.020 | |
| | | 9.09 | nM | 13.910 | |
| | | 2.84 | nM | 33.270 | |
| | | 888.18 | pM | 15.500 | |
| 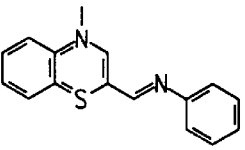 59-0022 | 266.37 | | | | |
| 59-0022 | | 100.00 | uM | 7.250 | |
| | | 31.25 | uM | -2.070 | |
| | | 9.77 | uM | -0.270 | |
| | | 3.05 | uM | 4.390 | |
| | | 953.67 | nM | 3.060 | |
| | | 298.02 | nM | -1.800 | |
| | | 93.13 | nM | -0.200 | |
| | | 29.10 | nM | -3.270 | |
| | | 9.09 | nM | 1.130 | |
| | | 2.84 | nM | 2.590 | |
| | | 888.18 | pM | 2.460 | |
| 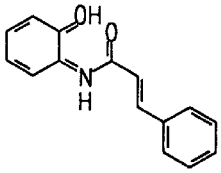 59-0023 | 239.28 | | | | |
| 59-0023 | | 100.00 | uM | -12.720 | |
| | | 31.25 | uM | 33.140 | |
| | | 9.77 | uM | 56.500 | |
| | | 3.05 | uM | 29.550 | |
| | | 953.67 | nM | 25.360 | |
| | | 298.02 | nM | 15.700 | |
| | | 93.13 | nM | 7.380 | |
| | | 29.10 | nM | 9.710 | |
| | | 9.09 | nM | 1.000 | |
| | | 2.84 | nM | 4.520 | |
| | | 888.18 | pM | -0.010 | |
FIG. 3D

| | | | | |
|---|---|---|---|---|
| 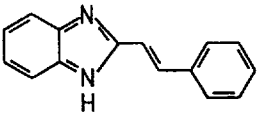 59-0024 | 220.28 | | | |
| 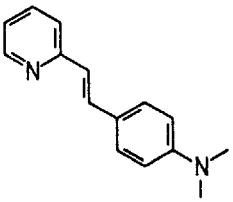 59-0025 | 224.31 | | | |
| 59-0025 | | 100.00 | uM | -25.590 |
| | | 31.25 | uM | 14.150 |
| | | 9.77 | uM | 50.690 |
| | | 3.05 | uM | 57.880 |
| | | 953.67 | nM | 38.900 |
| | | 298.02 | nM | 28.530 |
| | | 93.13 | nM | 19.660 |
| | | 29.10 | nM | 17.490 |
| | | 9.09 | nM | -0.600 |
| | | 2.84 | nM | -4.190 |
| | | 888.18 | pM | 4.670 |
| 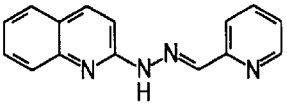 59-0026 | 248.29 | | | |
| 59-0026 | | 100.00 | uM | -29.830 |
| | | 31.25 | uM | -9.440 |
| | | 9.77 | uM | -10.470 |
| | | 3.05 | uM | 46.220 |
| | | 953.67 | nM | 107.760 |
| | | 298.02 | nM | 86.720 |
| | | 93.13 | nM | 36.850 |
| | | 29.10 | nM | 26.720 |
| | | 9.09 | nM | 8.520 |
| | | 2.84 | nM | -1.240 |
| | | 888.18 | pM | 4.020 |
FIG. 3E

| | | | | |
|---|---|---|---|---|
| 59-0027 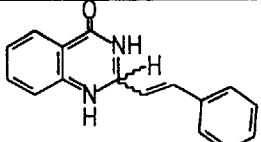 | 250.30 | | | |
| 59-0027 | | 100.00 uM | 89.810 | |
| | | 31.25 uM | 54.670 | |
| | | 9.77 uM | 44.940 | |
| | | 3.05 uM | 23.780 | |
| | | 953.67 nM | 8.380 | |
| | | 298.02 nM | 6.330 | |
| | | 93.13 nM | 7.360 | |
| | | 29.10 nM | 3.380 | |
| | | 9.09 nM | -1.620 | |
| | | 2.84 nM | -3.670 | |
| | | 888.18 pM | -0.720 | |
| 59-0028 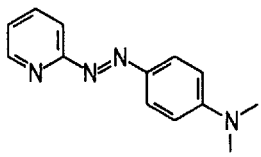 | 226.28 | | | |
| 59-0028 | | 100.00 uM | -26.750 | |
| | | 31.25 uM | -16.740 | |
| | | 9.77 uM | 29.550 | |
| | | 3.05 uM | 100.580 | |
| | | 953.67 nM | 54.940 | |
| | | 298.02 nM | 31.340 | |
| | | 93.13 nM | 7.500 | |
| | | 29.10 nM | 7.500 | |
| | | 9.09 nM | 7.880 | |
| | | 2.84 nM | 3.140 | |
| | | 888.18 pM | 4.670 | |
FIG. 3F

| | | | | | |
|---|---|---|---|---|---|
| 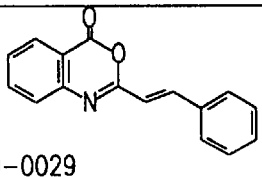 59-0029 | | 249.27 | | | |
| 59-0029 | | | 100.00 | uM | -15.150 |
| | | | 31.25 | uM | 41.940 |
| | | | 9.77 | uM | 36.630 |
| | | | 3.05 | uM | 7.120 |
| | | | 953.67 | nM | 21.880 |
| | | | 298.02 | nM | 15.540 |
| | | | 93.13 | nM | 1.810 |
| | | | 29.10 | nM | 1.370 |
| | | | 9.09 | nM | 12.140 |
| | | | 2.84 | nM | -4.230 |
| | | | 888.18 | pM | 9.040 |
| 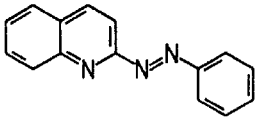 59-0030A | | 233.28 | | | |
| 59-0030A | | | 100.00 | uM | -27.970 |
| | | | 31.25 | uM | -22.830 |
| | | | 9.77 | uM | -5.420 |
| | | | 3.05 | uM | 57.280 |
| | | | 953.67 | nM | 72.620 |
| | | | 298.02 | nM | 53.000 |
| | | | 93.13 | nM | 29.990 |
| | | | 29.10 | nM | 14.630 |
| | | | 9.09 | nM | 3.870 |
| | | | 2.84 | nM | 6.970 |
| | | | 888.18 | pM | 1.810 |
| 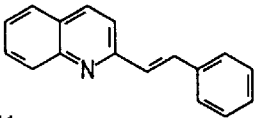 59-0031 | | 231.30 | | | |
| 59-0031 | | | 100.00 | uM | -25.790 |
| | | | 31.25 | uM | -17.810 |
| | | | 9.77 | uM | 20.840 |
| | | | 3.05 | uM | 87.380 |
| | | | 953.67 | nM | 49.320 |
| | | | 298.02 | nM | 43.110 |
| | | | 93.13 | nM | 29.530 |
| | | | 29.10 | nM | 1.810 |
| | | | 9.09 | nM | 1.220 |
| | | | 2.84 | nM | -0.550 |
| | | | 888.18 | pM | 4.160 |
FIG. 3G

| | | | | |
|---|---|---|---|---|
| 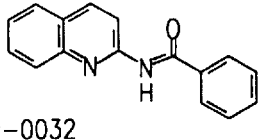 59-0032 | 248.29 | | | |
| 59-0032 | | 100.00 | uM | -7.780 |
| | | 31.25 | uM | 40.750 |
| | | 9.77 | uM | 42.820 |
| | | 3.05 | uM | 25.700 |
| | | 953.67 | nM | 31.170 |
| | | 298.02 | nM | 34.410 |
| | | 93.13 | nM | 3.570 |
| | | 29.10 | nM | 4.320 |
| | | 9.09 | nM | -10.000 |
| | | 2.84 | nM | 5.650 |
| | | 888.18 | pM | 11.990 |
| 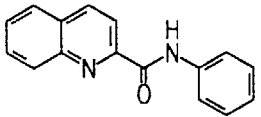 59-0033 | 248.29 | | | |
| 59-0033 | | 100.00 | uM | -28.180 |
| | | 31.25 | uM | -11.590 |
| | | 9.77 | uM | 55.300 |
| | | 3.05 | uM | 49.710 |
| | | 953.67 | nM | 47.410 |
| | | 298.02 | nM | 0.250 |
| | | 93.13 | nM | 7.980 |
| | | 29.10 | nM | -8.940 |
| | | 9.09 | nM | -7.630 |
| | | 2.84 | nM | -0.400 |
| | | 888.18 | pM | -5.980 |
| 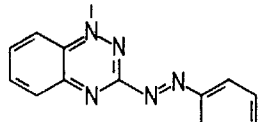 59-0034 | 268.34 | | | |
| 59-0034 | | 100.00 | uM | -28.51 |
| | | 31.25 | uM | 24 |
| | | 9.77 | uM | 73.58 |
| | | 3.05 | uM | 37.91 |
| | | 953.67 | nM | 20.09 |
| | | 298.02 | nM | 16.87 |
| | | 93.13 | nM | 15.23 |
| | | 29.10 | nM | 28.83 |
| | | 9.09 | nM | 9.08 |
| | | 2.84 | nM | 23.02 |
| | | 888.18 | pM | -0.32 |
FIG. 3H

| | | | | |
|---|---|---|---|---|
| 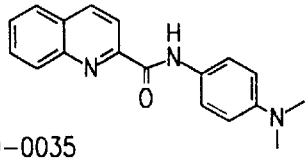 59-0035 | 291.36 | | | |
| 59-0035 | | 100.00 | uM | -14.92 |
| | | 31.25 | uM | 29.17 |
| | | 9.77 | uM | 15.87 |
| | | 3.05 | uM | 18.8 |
| | | 953.67 | nM | 3.88 |
| | | 298.02 | nM | 6.15 |
| | | 93.13 | nM | 3.22 |
| | | 29.10 | nM | -10.03 |
| | | 9.09 | nM | 15.58 |
| | | 2.84 | nM | -3.56 |
| | | 888.18 | pM | -7.13 |
| 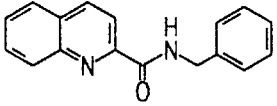 59-0036 | 262.31 | | | |
| 59-0036 | | 100.00 | uM | -0.98 |
| | | 31.25 | uM | -3.25 |
| | | 9.77 | uM | -4.54 |
| | | 3.05 | uM | -1.95 |
| | | 953.67 | nM | 0.32 |
| | | 298.02 | nM | -6.49 |
| | | 93.13 | nM | -17.19 |
| | | 29.10 | nM | -0.66 |
| | | 9.09 | nM | -5.52 |
| | | 2.84 | nM | -9.4 |
| | | 888.18 | pM | -16.53 |
| 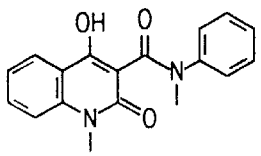 59-0037 | 308.00 | | | |
| 59-0037 | | 100.00 | uM | -10.69 |
| | | 31.25 | uM | -11.99 |
| | | 9.77 | uM | -10.03 |
| | | 3.05 | uM | -19.11 |
| | | 953.67 | nM | -9.4 |
| | | 298.02 | nM | 2.27 |
| | | 93.13 | nM | -2.9 |
| | | 29.10 | nM | -10.69 |
| | | 9.09 | nM | 2.59 |
| | | 2.84 | nM | 0.66 |
| | | 888.18 | pM | -2.59 |
FIG. 31

| Structure | ID | MW | Conc | Unit | Value | |
|---|---|---|---|---|---|---|
| 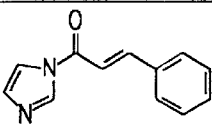 | 59-0038 | 291.36 | | | | |
| | 59-0038 | | 100.00 | uM | -23.430 | |
| | | | 31.25 | uM | -8.390 | |
| | | | 9.77 | uM | -0.100 | |
| | | | 3.05 | uM | -2.860 | |
| | | | 953.67 | nM | -2.240 | |
| | | | 298.02 | nM | 3.900 | |
| | | | 93.13 | nM | 6.350 | |
| | | | 29.10 | nM | 1.150 | |
| | | | 9.09 | nM | 6.960 | |
| | | | 2.84 | nM | -4.390 | |
| | | | 888.18 | pM | 0.380 | |
| 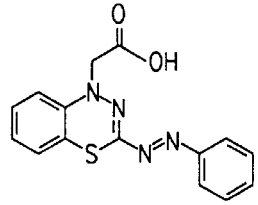 | 59-0039 | 312.35 | | | | |
| | 59-0039 | | 100.00 | uM | 14.170 | |
| | | | 31.25 | uM | 7.620 | |
| | | | 9.77 | uM | 1.940 | |
| | | | 3.05 | uM | -3.140 | |
| | | | 953.67 | nM | -7.770 | |
| | | | 298.02 | nM | -5.980 | |
| | | | 93.13 | nM | -8.820 | |
| | | | 29.10 | nM | -2.390 | |
| | | | 9.09 | nM | -16.580 | |
| | | | 2.84 | nM | -4.480 | |
| | | | 888.18 | pM | -0.450 | |
| 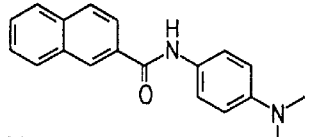 | 59-0040 | 290.37 | | | | |
| | 59-0040 | | 100.00 | uM | -20.400 | |
| | | | 31.25 | uM | -17.310 | |
| | | | 9.77 | uM | -8.110 | |
| | | | 3.05 | uM | 32.180 | |
| | | | 953.67 | nM | 36.180 | |
| | | | 298.02 | nM | 17.440 | |
| | | | 93.13 | nM | 2.040 | |
| | | | 29.10 | nM | 10.350 | |
| | | | 9.09 | nM | 6.070 | |
| | | | 2.84 | nM | 6.960 | |
| | | | 888.18 | pM | 13.440 | |
FIG. 3J

| | | | | |
|---|---|---|---|---|
| 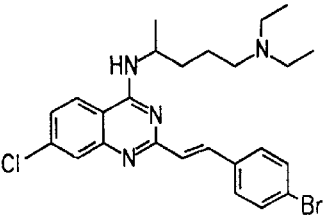 59-0041 | 501.90 | | | |
| 59-0041 | | 100.00 | uM | -18.37 |
| | | 31.25 | uM | -17.33 |
| | | 9.77 | uM | -5.11 |
| | | 3.05 | uM | 3.31 |
| | | 953.67 | nM | -0.77 |
| | | 298.02 | nM | -1.56 |
| | | 93.13 | nM | 3.55 |
| | | 29.10 | nM | -11.24 |
| | | 9.09 | nM | 0.25 |
| | | 2.84 | nM | -0.27 |
| | | 888.18 | pM | 2.02 |
| 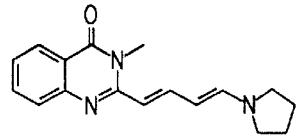 59-0042 | 281.36 | | | |
| 59-0042 | | 100.00 | uM | 163.51 |
| | | 31.25 | uM | -7.67 |
| | | 9.77 | uM | 9.41 |
| | | 3.05 | uM | 0.75 |
| | | 953.67 | nM | 6.11 |
| | | 298.02 | nM | 3.82 |
| | | 93.13 | nM | 2.54 |
| | | 29.10 | nM | 4.07 |
| | | 9.09 | nM | -9.73 |
| | | 2.84 | nM | -0.02 |
| | | 888.18 | pM | 18.37 |
| 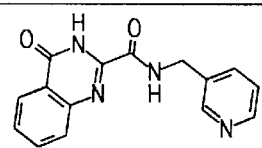 59-0043 | 280.29 | | | |
| 59-0043 | | 100.00 | uM | 20.66 |
| | | 31.25 | uM | 7.4 |
| | | 9.77 | uM | -1.29 |
| | | 3.05 | uM | -2.31 |
| | | 953.67 | nM | 1.54 |
| | | 298.02 | nM | -0.79 |
| | | 93.13 | nM | 1.52 |
| | | 29.10 | nM | 2.79 |
| | | 9.09 | nM | -0.27 |
| | | 2.84 | nM | 8.92 |
| | | 888.18 | pM | -4.34 |
FIG. 3K

| | | | | | |
|---|---|---|---|---|---|
| 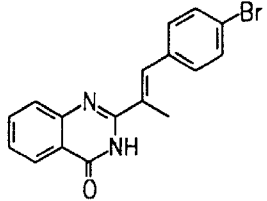 | | | | | |
| 59-0044 | 341.21 | | | | |
| 59-0044 | | 100.00 | uM | 7.38 | |
| | | 31.25 | uM | 11.72 | |
| | | 9.77 | uM | 12.49 | |
| | | 3.05 | uM | -0.52 | |
| | | 953.67 | nM | 0.5 | |
| | | 298.02 | nM | 6.11 | |
| | | 93.13 | nM | -1.54 | |
| | | 29.10 | nM | 19.14 | |
| | | 9.09 | nM | 7.13 | |
| | | 2.84 | nM | -2.06 | |
| | | 888.18 | pM | 5.84 | |
| 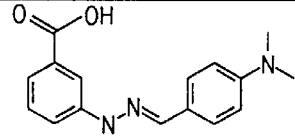 | | | | | |
| 59-0045 | 283.33 | | | | |
| 59-0045 | | 100.00 | uM | 52.37 | 64.460 |
| | | 31.25 | uM | 148.43 | 192.960 |
| | | 9.77 | uM | 204.47 | 422.540 |
| | | 3.05 | uM | 280.3 | 437.020 |
| | | 953.67 | nM | 254.82 | 410.890 |
| | | 298.02 | nM | 218.21 | 266.090 |
| | | 93.13 | nM | 196.98 | 183.730 |
| | | 29.10 | nM | 96.06 | 80.440 |
| | | 9.09 | nM | 67.35 | 55.530 |
| | | 2.84 | nM | 52.99 | 44.160 |
| 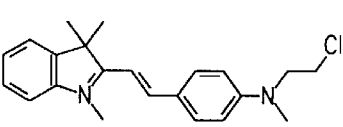 | | | | | |
| 59-0046 | 389.37 | | | | |
| 59-0046 | | 100.00 | uM | 79.33 | |
| | | 31.25 | uM | 2.24 | |
| | | 9.77 | uM | -1.67 | |
| | | 3.05 | uM | -6.18 | |
| | | 953.67 | nM | 0.001 | |
| | | 298.02 | nM | -3.63 | |
| | | 93.13 | nM | -0.84 | |
| | | 29.10 | nM | -8.42 | |
| | | 9.09 | nM | 3.92 | |
| | | 2.84 | nM | 0.3 | |
| | | 888.18 | pM | 5.61 | |
FIG. 3L

| Compound | MW | Conc | Unit | Value |
|---|---|---|---|---|
| 59-0047 (structure) | 303.37 | | | |
| 59-0047 | | 100.00 | uM | -6.73 |
| | | 31.25 | uM | 10.38 |
| | | 9.77 | uM | -6.16 |
| | | 3.05 | uM | -1.39 |
| | | 953.67 | nM | -10.11 |
| | | 298.02 | nM | -4.49 |
| | | 93.13 | nM | -7.28 |
| | | 29.10 | nM | -12.34 |
| | | 9.09 | nM | -3.08 |
| | | 2.84 | nM | -2.26 |
| | | 888.18 | pM | -5.34 |
| 59-0048 (structure) | 384.50 | | | |
| 59-0048 | | 100.00 | uM | -6.73 |
| | | 31.25 | uM | 0.27 |
| | | 9.77 | uM | -5.61 |
| | | 3.05 | uM | -2.26 |
| | | 953.67 | nM | -12.89 |
| | | 298.02 | nM | -1.69 |
| | | 93.13 | nM | -4.77 |
| | | 29.10 | nM | -8.14 |
| | | 9.09 | nM | -3.92 |
| | | 2.84 | nM | -11.2 |
| | | 888.18 | pM | -4.77 |
| 59-0049 (structure) | 251.29 | | | |
| 59-0049 | | 100.00 | uM | 4.49 |
| | | 31.25 | uM | 0 |
| | | 9.77 | uM | -4.77 |
| | | 3.05 | uM | 1.96 |
| | | 953.67 | nM | 8.69 |
| | | 298.02 | nM | -5.04 |
| | | 93.13 | nM | -2.24 |
| | | 29.10 | nM | 1.69 |
| | | 9.09 | nM | -4.49 |
| | | 2.84 | nM | 2.24 |
| | | 888.18 | pM | -0.3 |

FIG. 3M

| | | | | |
|---|---|---|---|---|
| 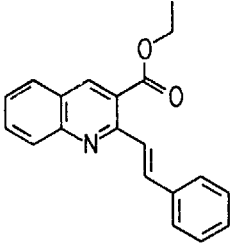 59-0050 | 303.36 | | | |
| 59-0050 | | 100.00 | uM | 45.79 |
| | | 31.25 | uM | 10.02 |
| | | 9.77 | uM | 11.29 |
| | | 3.05 | uM | -4.68 |
| | | 953.67 | nM | -6.92 |
| | | 298.02 | nM | -5.65 |
| | | 93.13 | nM | 1.69 |
| | | 29.10 | nM | -7.57 |
| | | 9.09 | nM | -12.05 |
| | | 2.84 | nM | -13.63 |
| | | 888.18 | pM | 5.2 |
| 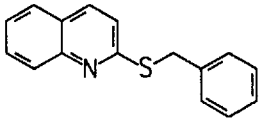 59-0051 | 251.35 | | | |
| 59-0051 | | 100.00 | uM | 32.36 |
| | | 31.25 | uM | -18.42 |
| | | 9.77 | uM | -0.55 |
| | | 3.05 | uM | -13.94 |
| | | 953.67 | nM | -12.02 |
| | | 298.02 | nM | -14.59 |
| | | 93.13 | nM | -7.55 |
| | | 29.10 | nM | -11.4 |
| | | 9.09 | nM | -14.91 |
| | | 2.84 | nM | -10.74 |
| | | 888.18 | pM | -20.03 |
FIG. 3N

| | | | | | |
|---|---|---|---|---|---|
| 59-0052 | 393.28 | | | | |
| 59-0052 | | 100.00 | uM | -21.62 | |
| | | 31.25 | uM | -13.32 | |
| | | 9.77 | uM | -21.31 | |
| | | 3.05 | uM | -11.08 | |
| | | 953.67 | nM | -20.66 | |
| | | 298.02 | nM | -17.14 | |
| | | 93.13 | nM | -16.49 | |
| | | 29.10 | nM | -11.4 | |
| | | 9.09 | nM | -10.74 | |
| | | 2.84 | nM | -11.08 | |
| | | 888.18 | pM | -14.59 | |
| 59-0053 | 354.41 | | | | |
| 59-0053 | | 100.00 | uM | -17.14 | |
| | | 31.25 | uM | -21.31 | |
| | | 9.77 | uM | -9.47 | |
| | | 3.05 | uM | -11.08 | |
| | | 953.67 | nM | -0.83 | |
| | | 298.02 | nM | -11.4 | |
| | | 93.13 | nM | -9.47 | |
| | | 29.10 | nM | -19.72 | |
| | | 9.09 | nM | -18.45 | |
| | | 2.84 | nM | -10.09 | |
| | | 888.18 | pM | -2.76 | |

FIG. 30

| | | | | | |
|---|---|---|---|---|---|
| 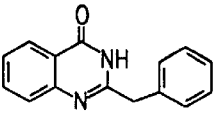 | | | | | |
| 59-0054 | | 236.28 | | | |
| 59-0054 | | | 100.00 | uM | -20.04 |
| | | | 31.25 | uM | -6.95 |
| | | | 9.77 | uM | 8.3 |
| | | | 3.05 | uM | -3.37 |
| | | | 953.67 | nM | -2.4 |
| | | | 298.02 | nM | -0.99 |
| | | | 93.13 | nM | -0.99 |
| | | | 29.10 | nM | -1.94 |
| | | | 9.09 | nM | 5.92 |
| | | | 2.84 | nM | -2.17 |
| | | | 888.18 | pM | -9.31 |
| 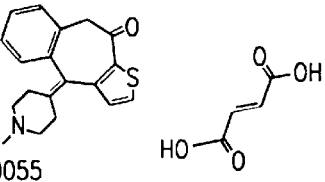 | | | | | |
| 59-0055 | | 425.51 | | | |
| 59-0055 | | | 100.00 | uM | -13.76 |
| | | | 31.25 | uM | -9.51 |
| | | | 9.77 | uM | -2.02 |
| | | | 3.05 | uM | 3.24 |
| | | | 953.67 | nM | -6.27 |
| | | | 298.02 | nM | -4.05 |
| | | | 93.13 | nM | -1.62 |
| | | | 29.10 | nM | -7.49 |
| | | | 9.09 | nM | -7.09 |
| | | | 2.84 | nM | -3.04 |
| 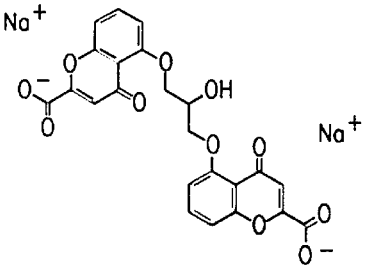 | | | | | |
| 59-0056 | | 512.34 | | | |
| 59-0056 | | | 100.00 | uM | -1.42 |
| | | | 31.25 | uM | -4.87 |
| | | | 9.77 | uM | 0.18 |
| | | | 3.05 | uM | 3.84 |
| | | | 953.67 | nM | -5.07 |
| | | | 298.02 | nM | -7.29 |
| | | | 93.13 | nM | 0.001 |
| | | | 29.10 | nM | -4.25 |
| | | | 9.09 | nM | -1.02 |
| | | | 2.84 | nM | -3.85 |
FIG. 3P

| | | | | | |
|---|---|---|---|---|---|
| 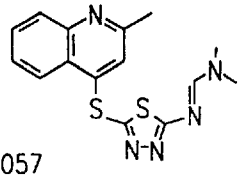 59-0057 | | | | | |
| 59-0057 | | 100.00 | uM | -24.150 | |
| | | 31.25 | uM | -24.300 | |
| | | 9.77 | uM | -5.980 | |
| | | 3.05 | uM | -11.500 | |
| | | 953.67 | nM | -13.000 | |
| | | 298.02 | nM | -6.280 | |
| | | 93.13 | nM | -12.550 | |
| | | 29.10 | nM | -6.870 | |
| | | 9.09 | nM | -8.520 | |
| | | 2.84 | nM | -16.290 | |
| 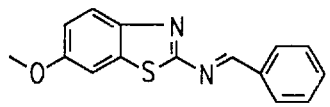 59-0058 | | | | | |
| 59-0058 | | 100.00 | uM | 4.170 | |
| | | 31.25 | uM | 7.620 | |
| | | 9.77 | uM | -1.790 | |
| | | 3.05 | uM | -7.320 | |
| | | 953.67 | nM | -1.940 | |
| | | 298.02 | nM | -6.870 | |
| | | 93.13 | nM | -1.490 | |
| | | 29.10 | nM | -8.370 | |
| | | 9.09 | nM | -5.080 | |
| | | 2.84 | nM | -12.400 | |
| 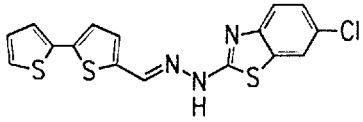 59-0059 | | | | | |
| 59-0059 | | 100.00 | uM | -18.700 | |
| | | 31.25 | uM | -16.140 | |
| | | 9.77 | uM | -3.090 | |
| | | 3.05 | uM | 0.150 | |
| | | 953.67 | nM | 6.010 | |
| | | 298.02 | nM | -1.910 | |
| | | 93.13 | nM | -1.760 | |
| | | 29.10 | nM | -9.100 | |
| | | 9.09 | nM | -8.220 | |
| | | 2.84 | nM | -5.720 | |
FIG. 3Q

| | | | | | |
|---|---|---|---|---|---|
|  59-0060 | | | | | |
| 59-0060 | | 100.00 | uM | -4.250 | |
| | | 31.25 | uM | -14.520 | |
| | | 9.77 | uM | 1.030 | |
| | | 3.05 | uM | -1.180 | |
| | | 953.67 | nM | -13.200 | |
| | | 298.02 | nM | -0.740 | |
| | | 93.13 | nM | -3.670 | |
| | | 29.10 | nM | -7.340 | |
| | | 9.09 | nM | -1.310 | |
| | | 2.84 | nM | 0.290 | |
|  59-0061 | | | | | |
| 59-0061 | | 100.00 | uM | -17.890 | |
| | | 31.25 | uM | -18.770 | |
| | | 9.77 | uM | -17.170 | |
| | | 3.05 | uM | -14.080 | |
| | | 953.67 | nM | -17.020 | |
| | | 298.02 | nM | -7.190 | |
| | | 93.13 | nM | -1.910 | |
| | | 29.10 | nM | -0.440 | |
| | | 9.09 | nM | -6.010 | |
| | | 2.84 | nM | -4.560 | |
|  59-0062 | | | | | |
| 59-0062 | | 100.00 | uM | -13.940 | |
| | | 31.25 | uM | -12.910 | |
| | | 9.77 | uM | -4.560 | |
| | | 3.05 | uM | -4.540 | |
| | | 953.67 | nM | -6.900 | |
| | | 298.02 | nM | -4.100 | |
| | | 93.13 | nM | -1.620 | |
| | | 29.10 | nM | 3.230 | |
FIG. 3R

| | | | | |
|---|---|---|---|---|
| | | 9.09 | nM | 8.070 |
| | | 2.84 | nM | 0.440 |
| 59-0063 (structure) | | | | |
| 59-0063 | | 100.00 | uM | -2.510 |
| | | 31.25 | uM | -6.130 |
| | | 9.77 | uM | -8.950 |
| | | 3.05 | uM | -8.020 |
| | | 953.67 | nM | -8.010 |
| | | 298.02 | nM | -2.520 |
| | | 93.13 | nM | -5.810 |
| | | 29.10 | nM | -3.450 |
| | | 9.09 | nM | -4.390 |
| | | 2.84 | nM | -6.280 |
| 59-0064 (structure) | | | | |
| 59-0064 | | 100.00 | uM | -23.090 |
| | | 31.25 | uM | -21.040 |
| | | 9.77 | uM | 78.400 |
| | | 3.05 | uM | 155.220 |
| | | 953.67 | nM | 113.120 |
| | | 298.02 | nM | 30.640 |
| | | 93.13 | nM | 15.240 |
| | | 29.10 | nM | 22.150 |
| | | 9.09 | nM | -0.770 |
| | | 2.84 | nM | 4.410 |
| 59-0065 (structure) | | | | |
| 59-0065 | | 100.00 | uM | -2.030 |
| | | 31.05 | uM | -2.980 |
| | | 9.77 | uM | -15.240 |
| | | 3.05 | uM | -15.400 |
| | | 953.67 | nM | -15.240 |
| | | 298.02 | nM | -10.520 |
| | | 93.13 | nM | -13.830 |
| | | 29.10 | nM | -5.810 |
| | | 9.09 | nM | -3.620 |
| | | 2.84 | nM | -7.070 |

FIG. 3S

| | | | | | |
|---|---|---|---|---|---|
| 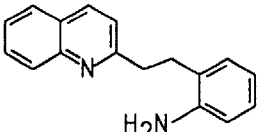 59-0066 | | | | | |
| 59-0066 | | 100.00 | uM | 10.060 | |
| | | 31.25 | uM | 2.680 | |
| | | 9.77 | uM | 10.850 | |
| | | 3.05 | uM | 14.610 | |
| | | 953.67 | nM | 0.950 | |
| | | 298.02 | nM | 3.780 | |
| | | 93.13 | nM | 1.730 | |
| | | 29.10 | nM | -2.820 | |
| | | 9.09 | nM | -2.820 | |
| | | 2.84 | nM | -3.920 | |
| 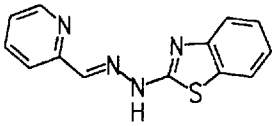 59-0067 | | | | | |
| 59-0067 | | 100.00 | uM | -24.040 | |
| | | 31.25 | uM | -24.890 | |
| | | 9.77 | uM | -1.450 | |
| | | 3.05 | uM | 60.900 | |
| | | 953.67 | nM | 133.860 | |
| | | 298.02 | nM | 75.330 | |
| | | 93.13 | nM | 28.760 | |
| | | 29.10 | nM | 20.070 | |
| | | 9.09 | nM | 4.980 | |
| | | 2.84 | nM | 4.450 | |
| 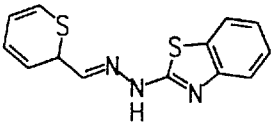 59-0068 | | | | | |
| 59-0068 | | 100.00 | uM | -22.130 | |
| | | 31.25 | uM | -7.880 | |
| | | 9.77 | uM | 93.900 | |
| | | 3.05 | uM | 81.060 | |
| | | 953.67 | nM | 22.330 | |
| | | 298.02 | nM | 17.300 | |
| | | 93.13 | nM | 8.460 | |
| | | 29.10 | nM | -3.530 | |
| | | 9.09 | nM | -4.230 | |
| | | 2.84 | nM | -6.140 | |
FIG. 3T

| | | | | | |
|---|---|---|---|---|---|
| 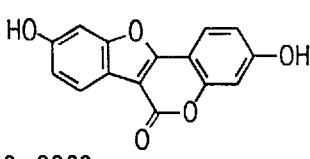 59-0069 | | | | | |
| 59-0069 | | | 100.00 | uM | 5.490 |
| | | | 31.25 | uM | 9.670 |
| | | | 9.77 | uM | 16.090 |
| | | | 3.05 | uM | -7.180 |
| | | | 953.67 | nM | -2.840 |
| | | | 298.02 | nM | -3.710 |
| | | | 93.13 | nM | -11.180 |
| | | | 29.10 | nM | -5.790 |
| | | | 9.09 | nM | -7.180 |
| | | | 2.84 | nM | -4.750 |
| 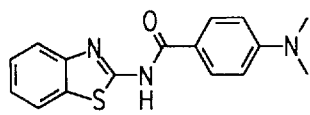 59-0070 | | | | | |
| 59-0070 | | | 100.00 | uM | -25.930 |
| | | | 31.25 | uM | -23.000 |
| | | | 9.77 | uM | 36.060 |
| | | | 3.05 | uM | 214.280 |
| | | | 953.67 | nM | 158.530 |
| | | | 298.02 | nM | 72.890 |
| | | | 93.13 | nM | 20.940 |
| | | | 29.10 | nM | 7.760 |
| | | | 9.09 | nM | 7.590 |
| | | | 2.84 | nM | -8.400 |
| 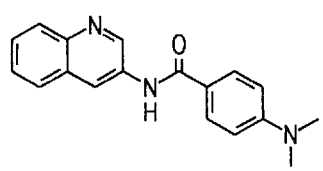 59-0071 | | | | | |
| 59-0071 | | | 100.00 | uM | -18.650 |
| | | | 31.25 | uM | -15.540 |
| | | | 9.77 | uM | 17.060 |
| | | | 3.05 | uM | 176.090 |
| | | | 953.67 | nM | 76.070 |
| | | | 298.02 | nM | 31.260 |
| | | | 93.13 | nM | 16.410 |
| | | | 29.10 | nM | 4.870 |
| | | | 9.09 | nM | -7.330 |
| | | | 2.84 | nM | -4.660 |
FIG. 3U

| | | | | | |
|---|---|---|---|---|---|
| 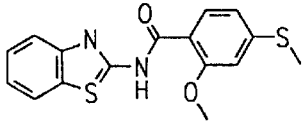 59-0072 | | | | | |
| 59-0072 | | 100.00 | uM | −19.750 | |
| | | 31.25 | uM | −18.650 | |
| | | 9.77 | uM | −18.430 | |
| | | 3.05 | uM | −15.770 | |
| | | 953.67 | nM | 9.970 | |
| | | 298.02 | nM | 74.740 | |
| | | 93.13 | nM | 175.430 | |
| | | 29.10 | nM | 213.580 | |
| | | 9.09 | nM | 164.320 | |
| | | 2.84 | nM | 119.100 | |
| | | 888.18 | pM | 60.770 | |
| 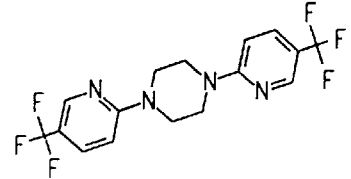 59-0073 | | | | | |
| 59-0073 | | 100.00 | uM | −3.010 | |
| | | 31.25 | uM | −4.830 | |
| | | 9.77 | uM | −9.660 | |
| | | 3.05 | uM | −4.680 | |
| | | 953.67 | nM | −6.500 | |
| | | 298.02 | nM | −2.510 | |
| | | 93.13 | nM | 7.140 | |
| | | 29.10 | nM | 0.97 | |
| | | 9.09 | nM | −5.5 | |
| | | 2.84 | nM | 5.3 | |
| 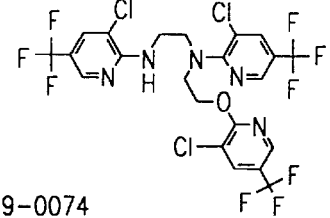 59-0074 | | | | | |
| 59-0074 | | 100.00 | uM | −2.85 | |
| | | 31.25 | uM | 2.14 | |
| | | 9.77 | uM | −4.85 | |
| | | 3.05 | uM | −3.5 | |
| | | 953.67 | nM | −4.85 | |
| | | 298.02 | nM | 9.95 | |
| | | 93.13 | nM | 4.47 | |
| | | 29.10 | nM | −8 | |
| | | 9.09 | nM | −4.17 | |
| | | 2.84 | nM | 6.97 | |
FIG. 3V

| | | | | | |
|---|---|---|---|---|---|
| 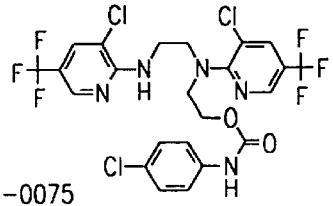 59-0075 | | | | | |
| 59-0075 | | 100.00 uM | | −0.68 | |
| | | 31.25 uM | | −10.16 | |
| | | 9.77 uM | | −5.35 | |
| | | 3.05 uM | | −6.5 | |
| | | 953.67 nM | | −0.85 | |
| | | 298.02 nM | | 5.97 | |
| | | 93.13 nM | | 0.97 | |
| | | 29.10 nM | | −2.35 | |
| | | 9.09 nM | | 0.32 | |
| | | 2.84 nM | | 10.47 | |
| 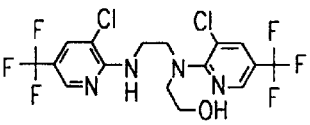 59-0076 | | | | | |
| 59-0076 | | 100.00 uM | | −19.12 | |
| | | 31.25 uM | | 9.29 | |
| | | 9.77 uM | | 10.63 | |
| | | 3.05 uM | | 22.43 | |
| | | 953.67 nM | | 19.93 | |
| | | 298.02 nM | | 3.47 | |
| | | 93.13 nM | | 19.93 | |
| | | 29.10 nM | | 10.63 | |
| | | 9.09 nM | | 14.28 | |
| | | 2.84 nM | | 11.3 | |
| 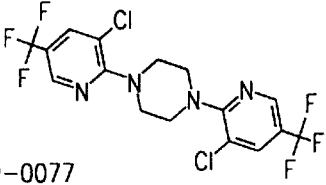 59-0077 | | | | | |
| 59-0077 | | 100.00 uM | | −20.96 | |
| | | 31.25 uM | | −16.23 | |
| | | 9.77 uM | | −10.58 | |
| | | 3.05 uM | | −11.96 | |
| | | 953.67 nM | | −19.44 | |
| | | 298.02 nM | | −17.3 | |
| | | 93.13 nM | | −13.79 | |
| | | 29.10 nM | | −15.62 | |
| | | 9.09 nM | | −14.09 | |
| | | 2.84 nM | | −14.4 | |
FIG. 3W

| | | | | | |
|---|---|---|---|---|---|
| 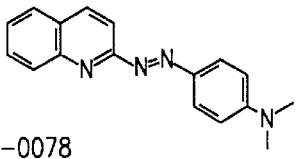 59-0078 | | | | | |
| 59-0078 | | 100.00 | uM | -26.540 | |
| | | 31.25 | uM | -22.560 | |
| | | 9.77 | uM | 71.530 | |
| | | 3.05 | uM | 207.960 | |
| | | 953.67 | nM | 379.230 | |
| | | 298.02 | nM | 241.460 | |
| | | 93.13 | nM | 136.100 | |
| | | 29.10 | nM | 84.020 | |
| | | 9.09 | nM | 50.350 | |
| | | 2.84 | nM | 56.600 | |
| | | 888.18 | pM | 92.520 | |
| 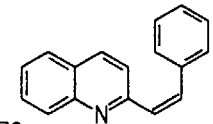 59-0079 | | | | | |
| 59-0079 | | 100.00 | uM | -34.980 | |
| | | 31.25 | uM | -21.390 | |
| | | 9.77 | uM | 37.200 | |
| | | 3.05 | uM | 122.580 | |
| | | 953.67 | nM | 69.010 | |
| | | 298.02 | nM | 64.000 | |
| | | 93.13 | nM | 46.490 | |
| | | 29.10 | nM | 30.310 | |
| | | 9.09 | nM | 33.490 | |
| | | 2.84 | nM | 29.760 | |
| 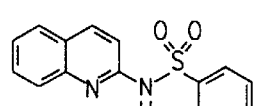 59-0080 | | | | | |
| 59-0080 | | 100.00 | uM | 5.390 | |
| | | 31.25 | uM | 5.560 | |
| | | 9.77 | uM | 6.440 | |
| | | 3.05 | uM | 2.440 | |
| | | 953.67 | nM | -5.030 | |
| | | 298.02 | nM | 7.660 | |
| | | 93.13 | nM | -3.630 | |
| | | 29.10 | nM | 3.650 | |
| | | 9.09 | nM | 1.050 | |
| | | 2.84 | nM | 6.940 | |
| 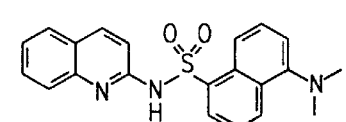 59-0081 | | | | | |
FIG. 3X

| | | | | |
|---|---|---|---|---|
| 59-0081 | | 100.00 | uM | 62.840 |
| | | 31.25 | uM | 11.300 |
| | | 9.77 | uM | -8.670 |
| | | 3.05 | uM | 2.440 |
| | | 953.67 | nM | -5.200 |
| | | 298.02 | nM | -2.080 |
| | | 93.13 | nM | 1.220 |
| | | 29.10 | nM | -2.250 |
| | | 9.09 | nM | 1.050 |
| | | 2.84 | nM | -3.300 |
| 59-0082 | (structure) | | | |
| 59-0082 | | 100.00 | uM | 111.79 |
| | | 31.25 | uM | 62.68 |
| | | 9.77 | uM | 32.36 |
| | | 3.05 | uM | 9.11 |
| | | 953.67 | nM | -10.62 |
| | | 298.02 | nM | -1.86 |
| | | 93.13 | nM | -6.89 |
| | | 29.10 | nM | -3.91 |
| | | 9.09 | nM | 2.22 |
| | | 2.84 | nM | 16.36 |
| 59-0083 | (structure) | | | |
| 59-0083 | | 100.00 | uM | 48.93 |
| | | 31.25 | uM | 40.91 |
| | | 9.77 | uM | 25.85 |
| | | 3.05 | uM | 17.85 |
| | | 953.67 | nM | 8.55 |
| | | 298.02 | nM | 3.9 |
| | | 93.13 | nM | 2.05 |
| | | 29.10 | nM | 7.99 |
| | | 9.09 | nM | -3.91 |
| | | 2.84 | nM | 3.35 |
| 59-0084 | (structure) | | | |
| 59-0084 | | 100.00 | uM | 37.670 |
| | | 31.25 | uM | 26.050 |
| | | 9.77 | uM | 9.210 |
| | | 3.05 | uM | 10.070 |

FIG. 3Y

| | | | | |
|---|---|---|---|---|
| | | 953.67 | nM | 21.700 |
| | | 298.02 | nM | 5.900 |
| | | 93.13 | nM | 4.870 |
| | | 29.10 | nM | -10.920 |
| | | 9.09 | nM | 10.080 |
| | | 2.84 | nM | -2.080 |
| 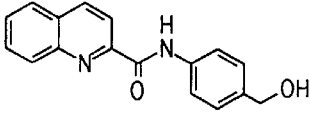 59-0085 | | | | |
| 59-0085 | | 100.00 | uM | 17.070 |
| | | 31.25 | uM | 41.890 |
| | | 9.77 | uM | 18.500 |
| | | 3.05 | uM | 20.340 |
| | | 953.67 | nM | 22.490 |
| | | 298.02 | nM | 8.090 |
| | | 93.13 | nM | 11.790 |
| | | 29.10 | nM | 1.240 |
| | | 9.09 | nM | -0.760 |
| | | 2.84 | nM | 5.940 |
| 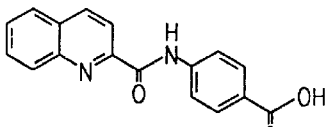 59-0086 | | | | |
| 59-0086 | | 100.00 | uM | 30.750 |
| | | 31.25 | uM | 31.190 |
| | | 9.77 | uM | 14.790 |
| | | 3.05 | uM | 13.500 |
| | | 953.67 | nM | 14.080 |
| | | 298.02 | nM | 3.940 |
| | | 93.13 | nM | 9.370 |
| | | 29.10 | nM | -2.610 |
| | | 9.09 | nM | -5.040 |
| | | 2.84 | nM | 1.530 |
| 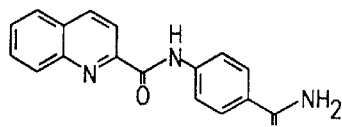 59-0087 | | | | |
| 59-0087 | | 100.00 | uM | 10.660 |
| | | 31.25 | uM | 11.080 |
| | | 9.77 | uM | 3.100 |
| | | 3.05 | uM | -1.320 |
| | | 953.67 | nM | 17.070 |
| | | 298.02 | nM | 7.950 |
| | | 93.13 | nM | -4.460 |
| | | 29.10 | nM | 4.510 |
| | | 9.09 | nM | -0.470 |
| | | 2.84 | nM | 9.660 |
FIG. 3Z

| | | | | | | |
|---|---|---|---|---|---|---|
| 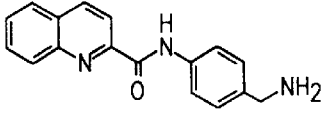 59-0088 | | | | | | |
| 59-0088 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
| | | 93.13 | nM | | | |
| | | 29.10 | nM | | | |
| | | 9.09 | nM | | | |
| | | 2.84 | nM | | | |
| 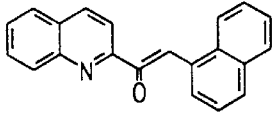 59-0089 | | | | | | |
| 59-0089 | | 100.00 | uM | 60.09 | | |
| | | 31.25 | uM | 116.25 | | |
| | | 9.77 | uM | 65.85 | | |
| | | 3.05 | uM | 36.1 | | |
| | | 953.67 | nM | 37.96 | | |
| | | 298.02 | nM | 18.42 | | |
| | | 93.13 | nM | 6.33 | | |
| | | 29.10 | nM | 13.58 | | |
| | | 9.09 | nM | 0.75 | | |
| | | 2.84 | nM | -5.77 | | |
| 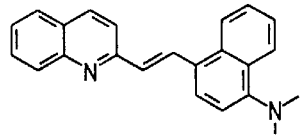 59-0090 | | | | | | |
| 59-0090 | | 100.00 | uM | 32.77 | | |
| | | 31.25 | uM | 24.63 | | |
| | | 9.77 | uM | 19.5 | | |
| | | 3.05 | uM | 41.31 | | |
| | | 953.67 | nM | 9.8 | | |
| | | 298.02 | nM | -1.76 | | |
| | | 93.13 | nM | 3.53 | | |
| | | 29.10 | nM | 2.95 | | |
| | | 9.09 | nM | 2.95 | | |
| | | 2.84 | nM | 7.8 | | |
| 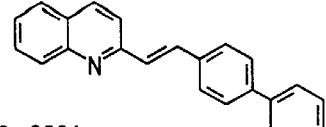 59-0091 | | | | | | |
| 59-0091 | | 100.00 | uM | 0.26 | | |
| | | 31.25 | uM | 13.54 | | |
FIG. 3AA

|  |  |  |  |  |
|---|---|---|---|---|
|  |  | 9.77 | uM | 95.94 |
|  |  | 3.05 | uM | 87.71 |
|  |  | 953.67 | nM | 44.17 |
|  |  | 298.02 | nM | 38.26 |
|  |  | 93.13 | nM | 23.87 |
|  |  | 29.10 | nM | 21.65 |
|  |  | 9.09 | nM | 10.95 |
|  |  | 2.84 | nM | 20.92 |
| 59-0092 | 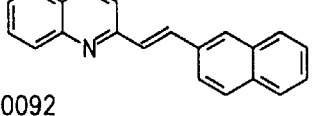 |  |  |  |
| 59-0092 |  | 100.00 | uM | -11.56 |
|  |  | 31.25 | uM | 17.84 |
|  |  | 9.77 | uM | 50.19 |
|  |  | 3.05 | uM | 25.84 |
|  |  | 953.67 | nM | 14.4 |
|  |  | 298.02 | nM | 6.77 |
|  |  | 93.13 | nM | 8.62 |
|  |  | 29.10 | nM | 2.22 |
|  |  | 9.09 | nM | 8.38 |
|  |  | 2.84 | nM | 1 |
| 59-0093 | 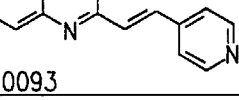 |  |  |  |
| 59-0093 |  | 100.00 | uM | -11.67 |
|  |  | 31.25 | uM | 15.02 |
|  |  | 9.77 | uM | 35.44 |
|  |  | 3.05 | uM | 29.89 |
|  |  | 953.67 | nM | 22.88 |
|  |  | 298.02 | nM | 19.56 |
|  |  | 93.13 | nM | 5.18 |
|  |  | 29.10 | nM | 7.39 |
|  |  | 9.09 | nM | 4.56 |
|  |  | 2.84 | nM | 5.9 |
| 59-0094 | 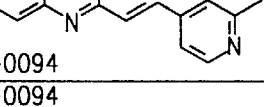 |  |  |  |
| 59-0094 |  | 100.00 | uM | -17.69 |
|  |  | 31.25 | uM | 45.15 |
|  |  | 9.77 | uM | 24.97 |
|  |  | 3.05 | uM | 19.81 |
|  |  | 953.67 | nM | 9.35 |
|  |  | 298.02 | nM | 1.36 |
|  |  | 93.13 | nM | 9.24 |
|  |  | 29.10 | nM | -0.48 |
|  |  | 9.09 | nM | 6.16 |
|  |  | 2.84 | nM | 1.61 |
FIG. 3BB

| | | | | | |
|---|---|---|---|---|---|
| 59-0095 [structure] | | | | | |
| 59-0095 | | 100.00 | uM | | 44.7 |
| | | 31.25 | uM | | 47.61 |
| | | 9.77 | uM | | 12.78 |
| | | 3.05 | uM | | 21.49 |
| | | 953.67 | nM | | 15.01 |
| | | 298.02 | nM | | 10.22 |
| | | 93.13 | nM | | 13.98 |
| | | 29.10 | nM | | 20.31 |
| | | 9.09 | nM | | 10.9 |
| | | 2.84 | nM | | 9.21 |
| 59-0096 [structure] | | | | | |
| 59-0096 | | 100.00 | uM | | 413.05 |
| | | 31.25 | uM | | 287.23 |
| | | 9.77 | uM | | 137.38 |
| | | 3.05 | uM | | 78.5 |
| | | 953.67 | nM | | 49.13 |
| | | 298.02 | nM | | 50.68 |
| | | 93.13 | nM | | 47.95 |
| | | 29.10 | nM | | 26.28 |
| | | 9.09 | nM | | 18.75 |
| | | 2.84 | nM | | 22.17 |
| 59-0097 [structure] | | | | | |
| 59-0097 | | 100.00 | uM | | 77.47 |
| | | 31.25 | uM | | 201.9 |
| | | 9.77 | uM | | 160.93 |
| | | 3.05 | uM | | 61.44 |
| | | 953.67 | nM | | 47.78 |
| | | 298.02 | nM | | 51.54 |
| | | 93.13 | nM | | 34.64 |
| | | 29.10 | nM | | 43.18 |
| | | 9.09 | nM | | 39.91 |
| | | 2.84 | nM | | 27.13 |

FIG. 3CC

| Structure | | Conc | | Value1 | Value2 |
|---|---|---|---|---|---|
| 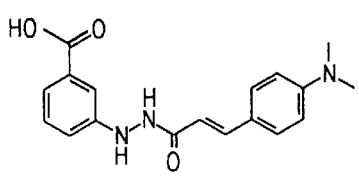 59-0098 | | | | | |
| 59-0098 | | 100.00 | uM | | -1.38 |
| | | 31.25 | uM | | 186.89 |
| | | 9.77 | uM | | 221.7 |
| | | 3.05 | uM | | 164.69 |
| | | 953.67 | nM | | 96.94 |
| | | 298.02 | nM | | 68.25 |
| | | 93.13 | nM | | 57 |
| | | 29.10 | nM | | 51.88 |
| | | 9.09 | nM | | 41.29 |
| | | 2.84 | nM | | 33.43 |
| 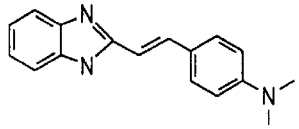 59-0099 | | | | | |
| 59-0099 | | 100.00 | uM | 13.040 | |
| | | 31.25 | uM | 56.880 | |
| | | 9.77 | uM | 119.340 | |
| | | 3.05 | uM | 237.420 | |
| | | 953.67 | nM | 285.440 | |
| | | 298.02 | nM | 164.610 | |
| | | 93.13 | nM | 123.300 | |
| | | 29.10 | nM | 69.240 | |
| | | 9.09 | nM | 44.500 | |
| | | 2.84 | nM | 47.390 | |
| 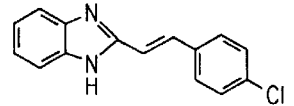 59-0100 | | | | | |
| 59-0100 | | 100.00 | uM | -10.020 | |
| | | 31.25 | uM | -10.730 | |
| | | 9.77 | uM | 30.340 | |
| | | 3.05 | uM | 114.410 | |
| | | 953.67 | nM | 77.540 | |
| | | 298.02 | nM | 40.290 | |
| | | 93.13 | nM | 35.730 | |
| | | 29.10 | nM | 28.290 | |
| | | 9.09 | nM | 17.480 | |
| | | 2.84 | nM | 11.470 | |
| 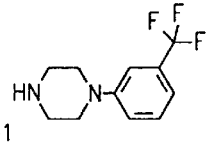 59-0101 | | | | | |
| 59-0101 | | 100.00 | uM | 26.370 | |
FIG. 3DD

| | | | | |
|---|---|---|---|---|
| | | 31.25 | uM | 12.440 |
| | | 9.77 | uM | -0.780 |
| | | 3.05 | uM | 10.280 |
| | | 953.67 | nM | 2.110 |
| | | 298.02 | nM | 7.860 |
| | | 93.13 | nM | 1.140 |
| | | 29.10 | nM | 2.820 |
| | | 9.09 | nM | 4.150 |
| | | 2.84 | nM | 5.590 |
| 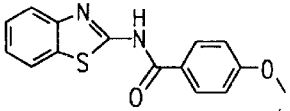 59-0102 | 284.34 | | | |
| 59-0102 | | 100.00 | uM | -24.350 |
| | | 31.25 | uM | -11.140 |
| | | 9.77 | uM | 63.540 |
| | | 3.05 | uM | 121.320 |
| | | 953.67 | nM | 79.530 |
| | | 298.02 | nM | 72.460 |
| | | 93.13 | nM | 66.290 |
| | | 29.10 | nM | 45.690 |
| | | 9.09 | nM | 27.260 |
| | | 2.84 | nM | 42.330 |
| | | 888.18 | nM | 33.430 |
| 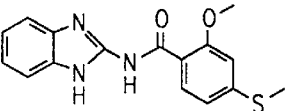 59-0103 | 313.38 | | | |
| | | 100.00 | uM | -29.69 |
| | | 31.25 | uM | -29.53 |
| | | 9.77 | uM | -28.22 |
| | | 3.05 | uM | -27.72 |
| | | 953.67 | nM | -5.58 |
| | | 298.02 | nM | 54.15 |
| | | 93.13 | nM | 170.95 |
| | | 29.10 | nM | 222.87 |
| | | 9.09 | nM | 210.39 |
| | | 2.84 | nM | 203.4 |
| | | 0.80 | nM | 114.55 |
| 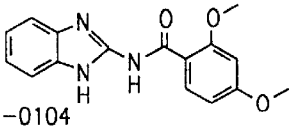 59-0104 | 297.31 | | | |
| | | 100.00 | uM | -29.84 |
| | | 31.25 | uM | -26.72 |
| | | 9.77 | uM | -29.2 |
| | | 3.05 | uM | -27.05 |
| | | 953.67 | nM | 24.37 |
| | | 298.02 | nM | 196.42 |
| | | 93.13 | nM | 213.89 |
FIG. 3EE

| | | | | |
|---|---|---|---|---|
| | | 29.10 | nM | 220.04 |
| | | 9.09 | nM | 245.42 |
| | | 2.84 | nM | 182.45 |
| | | 0.80 | nM | 119.55 |
| 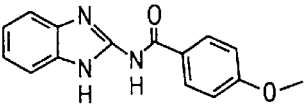 59-0105 | 267.29 | | | |
| | | 100.00 | uM | -25.72 |
| | | 31.25 | uM | -15.89 |
| | | 9.77 | uM | 31.7 |
| | | 3.05 | uM | 54.17 |
| | | 953.67 | nM | 53.67 |
| | | 298.02 | nM | 41.35 |
| | | 93.13 | nM | 44.5 |
| | | 29.10 | nM | 39.02 |
| | | 9.09 | nM | 25.38 |
| | | 2.84 | nM | 31.7 |
| | | 0.80 | nM | 18.05 |
| 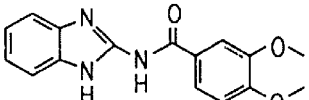 59-0106 | 297.31 | | | |
| | | 100.00 | uM | -14.05 |
| | | 31.25 | uM | 223.52 |
| | | 9.77 | uM | 202.58 |
| | | 3.05 | uM | 107.73 |
| | | 953.67 | nM | 71.3 |
| | | 298.02 | nM | 44.84 |
| | | 93.13 | nM | 26.54 |
| | | 29.10 | nM | 23.05 |
| | | 9.09 | nM | 27.87 |
| | | 2.84 | nM | 12.23 |
| | | 0.80 | nM | 11.4 |
| 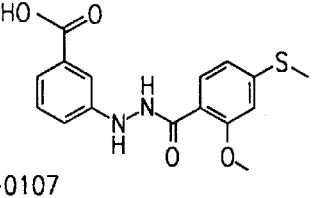 59-0107 | 332.38 | | | |
| | | 100.00 | uM | 48.55 |
| | | 31.25 | uM | 22.87 |
| | | 9.77 | uM | 7.19 |
| | | 3.05 | uM | 0.65 |
| | | 953.67 | nM | 11.12 |
| | | 298.02 | nM | -3.92 |
| | | 93.13 | nM | 1.09 |
| | | 29.10 | nM | -15.69 |
FIG. 3FF

| | | 9.09 | nM | -11.32 | |
| --- | --- | --- | --- | --- | --- |
| | | 2.84 | nM | -2.62 | |
| | | 0.80 | nM | -16.11 | |
| 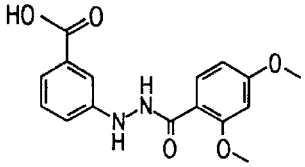 59-0108 | 316.31 | | | | |
| | | 100.00 | uM | 227.73 | |
| | | 31.25 | uM | 96.02 | |
| | | 9.77 | uM | 58.57 | |
| | | 3.05 | uM | 37.23 | |
| | | 953.67 | nM | 18.94 | |
| | | 298.02 | nM | 25.68 | |
| | | 93.13 | nM | -4.8 | |
| | | 29.10 | nM | 2.62 | |
| | | 9.09 | nM | -4.8 | |
| | | 2.84 | nM | 3.92 | |
| | | 0.80 | nM | 4.14 | |
| 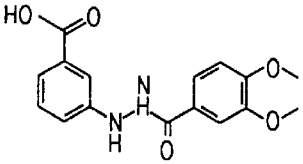 59-0109 | 316.31 | | | | |
| | | 100.00 | uM | 43.12 | |
| | | 31.25 | uM | 27.64 | |
| | | 9.77 | uM | 5.89 | |
| | | 3.05 | uM | 6.32 | |
| | | 953.67 | nM | 13.51 | |
| | | 298.02 | nM | 7.85 | |
| | | 93.13 | nM | 3.71 | |
| | | 29.10 | nM | -3.27 | |
| | | 9.09 | nM | 5.01 | |
| | | 2.84 | nM | -4.58 | |
| | | 0.80 | nM | 6.98 | |
| 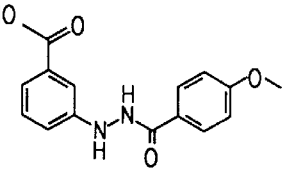 59-0110 | 286.29 | | | | |
| | | 100.00 | uM | 65.11 | |
| | | 31.25 | uM | 67.05 | |
| | | 9.77 | uM | 35.27 | |
| | | 3.05 | uM | 25.26 | |
| | | 953.67 | nM | 27.01 | |
| | | 298.02 | nM | 15.24 | |
FIG. 3GG

| | | 93.13 | nM | 10.68 | |
| --- | --- | --- | --- | --- | --- |
| | | 29.10 | nM | 5.89 | |
| | | 9.09 | nM | 5.45 | |
| | | 2.84 | nM | 10.24 | |
| | | 0.80 | nM | 4.14 | |
| 59-0111 (H₂N-NH-C₆H₄-COOH) | 152.15 | | | | |
| | | 100.00 | uM | 23.360 | |
| | | 31.25 | uM | 22.330 | |
| | | 9.77 | uM | 12.260 | |
| | | 3.05 | uM | 5.390 | |
| | | 953.67 | nM | 2.190 | |
| | | 298.02 | nM | 1.230 | |
| | | 93.13 | nM | 2.430 | |
| | | 29.10 | nM | 6.350 | |
| | | 9.09 | nM | 4.350 | |
| | | 2.84 | nM | 4.350 | |
| | | 0.80 | nM | 3.230 | |
| 59-0112 (4-dimethylaminobenzaldehyde) | 149.19 | | | | |
| | | 100.00 | uM | 2.670 | |
| | | 31.25 | uM | 4.670 | |
| | | 9.77 | uM | 2.750 | |
| | | 3.05 | uM | 3.790 | |
| | | 953.67 | nM | 4.270 | |
| | | 298.02 | nM | 1.150 | |
| | | 93.13 | nM | 9.630 | |
| | | 29.10 | nM | 0.920 | |
| | | 9.09 | nM | 0.510 | |
| | | 2.84 | nM | 12.900 | |
| | | 0.80 | nM | 2.990 | |
| 59-0113 (quinoline-dimethylaminostyryl) | 274.37 | | | | |
| | | 100.00 | uM | 22.010 | |
| | | 31.25 | uM | 25.940 | |
| | | 9.77 | uM | 7.500 | |
| | | 3.05 | uM | 3.070 | |
| | | 953.67 | nM | -0.760 | |
| | | 298.02 | nM | -4.690 | |
| | | 93.13 | nM | -4.790 | |
| | | 29.10 | nM | 5.090 | |
| | | 9.09 | nM | 0.150 | |
| | | 2.84 | nM | -0.250 | |
| | | 0.80 | nM | 0.150 | |

FIG. 3HH

| | | | | | |
|---|---|---|---|---|---|
| 59-0114 (structure) | 475.54 | | | | |
| | | 100.00 | uM | 52.030 | |
| | | 31.25 | uM | 36.120 | |
| | | 9.77 | uM | 25.840 | |
| | | 3.05 | uM | 16.670 | |
| | | 953.67 | nM | 12.540 | |
| | | 298.02 | nM | 9.420 | |
| | | 93.13 | nM | -1.060 | |
| | | 29.10 | nM | 2.160 | |
| | | 9.09 | nM | -6.000 | |
| | | 2.84 | nM | 2.470 | |
| | | 0.80 | nM | -1.460 | |
| 59-0115 (structure) | 318.87 | | | | |
| | | 100.00 | uM | 73.700 | |
| | | 31.25 | uM | 2.770 | |
| | | 9.77 | uM | -10.430 | |
| | | 3.05 | uM | -12.340 | |
| | | 953.67 | nM | -13.750 | |
| | | 298.02 | nM | -13.960 | |
| | | 93.13 | nM | -11.940 | |
| | | 29.10 | nM | -9.830 | |
| | | 9.09 | nM | -8.820 | |
| | | 2.84 | nM | -0.950 | |
| | | 0.80 | nM | -0.050 | |
| 59-0116 (structure) | 269.30 | | | | |
| | | 100.00 | uM | 31.380 | |
| | | 31.25 | uM | 109.060 | |
| | | 9.77 | uM | 231.070 | |
| | | 3.05 | uM | 240.670 | |
| | | 953.67 | nM | 132.020 | |
| | | 298.02 | nM | 75.820 | |
| | | 93.13 | nM | 53.250 | |
| | | 29.10 | nM | 47.500 | |
| | | 9.09 | nM | 39.440 | |
| | | 2.84 | nM | 42.170 | |
| | | 0.80 | nM | 31.180 | |
| 59-0117 (structure) | 268.38 | | | | |
| | | 100.00 | uM | -68.520 | |

FIG. 3II

| | | | | |
|---|---|---|---|---|
| | | 31.25 | uM | -7.450 |
| | | 9.77 | uM | 111.630 |
| | | 3.05 | uM | 64.340 |
| | | 953.67 | nM | 4.740 |
| | | 298.02 | nM | -19.270 |
| | | 93.13 | nM | -26.660 |
| | | 29.10 | nM | -28.880 |
| | | 9.09 | nM | -42.180 |
| | | 2.84 | nM | -41.300 |
| | | 0.80 | nM | -39.220 |
| 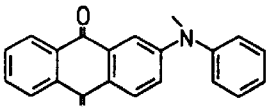 59-0118 | 313.36 | | | |
| | | 100.00 | uM | -67.170 |
| | | 31.25 | uM | -56.580 |
| | | 9.77 | uM | -58.060 |
| | | 3.05 | uM | -55.720 |
| | | 953.67 | nM | -48.200 |
| | | 298.02 | nM | -50.300 |
| | | 93.13 | nM | -33.310 |
| | | 29.10 | nM | -47.340 |
| | | 9.09 | nM | -49.310 |
| | | 2.84 | nM | -56.200 |
| | | 0.80 | nM | -57.310 |
| 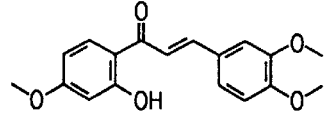 59-0119 | 314.34 | | | |
| | | 100.00 | uM | 167.500 |
| | | 31.25 | uM | -29.240 |
| | | 9.77 | uM | -57.800 |
| | | 3.05 | uM | -52.030 |
| | | 953.67 | nM | -54.240 |
| | | 298.02 | nM | -53.870 |
| | | 93.13 | nM | -38.110 |
| | | 29.10 | nM | -55.100 |
| | | 9.09 | nM | -52.270 |
| | | 2.84 | nM | -53.500 |
| | | 0.80 | nM | -43.650 |
| 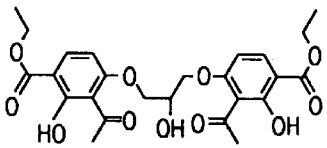 59-0120 | 504.49 | | | |
| | | 100.00 | uM | -82.790 |
| | | 31.25 | uM | -80.470 |
| | | 9.77 | uM | -66.800 |
| | | 3.05 | uM | -50.790 |
| | | 953.67 | nM | -54.240 |
| | | 298.02 | nM | -45.250 |
| | | 93.13 | nM | -50.660 |
FIG. 3JJ

| | | | | |
|---|---|---|---|---|
| | | 29.10 | nM | -50.300 |
| | | 9.09 | nM | -50.300 |
| | | 2.84 | nM | -50.300 |
| | | 0.80 | nM | -43.280 |
| 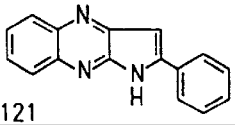 59-0121 | 245.29 | | | |
| | | 100.00 | uM | -79.690 |
| | | 31.25 | uM | -75.590 |
| | | 9.77 | uM | 25.650 |
| | | 3.05 | uM | 94.850 |
| | | 953.67 | nM | 43.910 |
| | | 298.02 | nM | -1.800 |
| | | 93.13 | nM | -4.150 |
| | | 29.10 | nM | -22.050 |
| | | 9.09 | nM | -31.110 |
| | | 2.84 | nM | -26.760 |
| | | 0.80 | nM | -28.270 |
| 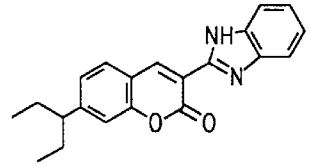 59-0122 | 333.39 | | | |
| | | 100.00 | uM | -19.050 |
| | | 31.25 | uM | -12.080 |
| | | 9.77 | uM | -7.610 |
| | | 3.05 | uM | 25.210 |
| | | 953.67 | nM | 83.580 |
| | | 298.02 | nM | 87.220 |
| | | 93.13 | nM | 63.890 |
| | | 29.10 | nM | 42.680 |
| | | 9.09 | nM | 45.320 |
| | | 2.84 | nM | 37.780 |
| | | 0.80 | nM | 27.030 |
| 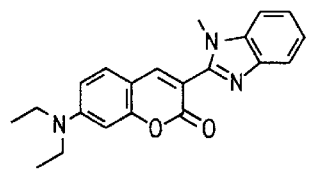 59-0123 | 347.42 | | | |
| | | 100.00 | uM | 34.430 |
| | | 31.25 | uM | 34.710 |
| | | 9.77 | uM | 38.620 |
| | | 3.05 | uM | 55.100 |
| | | 953.67 | nM | 51.900 |
| | | 298.02 | nM | 41.410 |
| | | 93.13 | nM | 29.970 |
| | | 29.10 | uM | 13.760 |
| | | 9.09 | nM | 17.120 |
| | | 2.84 | nM | 13.480 |
| | | 0.80 | nM | 1.190 |
FIG. 3KK

| | | | | | |
|---|---|---|---|---|---|
| 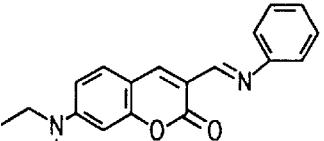 59-0124 | 350.44 | | | | |
| | | 100.00 | uM | 56.640 | |
| | | 31.25 | uM | 81.500 | |
| | | 9.77 | uM | 145.880 | |
| | | 3.05 | uM | 135.830 | |
| | | 953.67 | nM | 268.990 | |
| | | 298.02 | nM | 224.290 | |
| | | 93.13 | nM | 134.850 | |
| | | 29.10 | nM | 91.690 | |
| | | 9.09 | nM | 80.390 | |
| | | 2.84 | nM | 63.060 | |
| | | 0.80 | nM | 51.460 | |
| 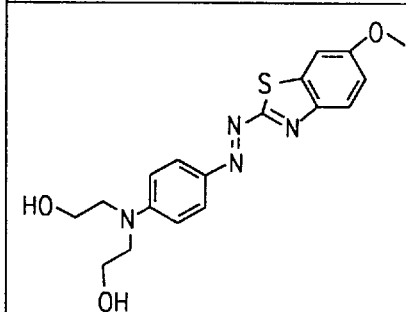 59-0125 | 372.45 | | | | |
| | | 100.00 | uM | -6.780 | |
| | | 31.25 | uM | 67.530 | |
| | | 9.77 | uM | 54.120 | |
| | | 3.05 | uM | 28.700 | |
| | | 953.67 | nM | 21.580 | |
| | | 298.02 | nM | 22.280 | |
| | | 93.13 | nM | 22.700 | |
| | | 29.10 | nM | 1.630 | |
| | | 9.09 | nM | 15.700 | |
| | | 2.84 | nM | 9.840 | |
| | | 0.80 | nM | 8.460 | |
FIG. 3LL

| Compound | MW | Conc | Unit | Value | |
|---|---|---|---|---|---|
| 59-0126 (structure) | 260.30 | | | | |
| | | 100.00 | uM | -17.390 | |
| | | 31.25 | uM | -13.100 | |
| | | 9.77 | uM | 9.270 | |
| | | 3.05 | uM | 40.530 | |
| | | 953.67 | nM | 21.390 | |
| | | 298.02 | nM | 25.660 | |
| | | 93.13 | nM | 9.430 | |
| | | 29.10 | nM | 6.360 | |
| | | 9.09 | nM | 6.510 | |
| | | 2.84 | nM | 0.080 | |
| | | 0.80 | nM | 3.750 | |
| 59-0127 (structure) | 329.41 | | | | |
| | | 100.00 | uM | -20.610 | |
| | | 31.25 | uM | -21.820 | |
| | | 9.77 | uM | -6.060 | |
| | | 3.05 | uM | -3.900 | |
| | | 953.67 | nM | -8.820 | |
| | | 298.02 | nM | -6.200 | |
| | | 93.13 | nM | 11.880 | |
| | | 29.10 | nM | 1.610 | |
| | | 9.09 | nM | 3.600 | |
| | | 2.84 | nM | -2.070 | |
| | | 0.80 | nM | 4.220 | |
| 59-0128 (structure) | 436.34 | | | | |
| | | 100.00 | uM | | |
| | | 31.25 | uM | | |
| | | 9.77 | uM | | |
| | | 3.05 | uM | | |
| | | 953.67 | nM | | |
| | | 298.02 | nM | | |
| | | 93.13 | nM | | |
| | | 29.10 | nM | | |

FIG. 3MM

| | | | | |
|---|---|---|---|---|
| | | 9.09 nM | | |
| | | 2.84 nM | | |
| | | 0.80 nM | | |
| 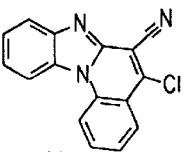 59-0129 | 277.71 | | | |
| | | 100.00 uM | -20.46 | |
| | | 31.25 uM | -21.21 | |
| | | 9.77 uM | 44.36 | |
| | | 3.05 uM | 4.38 | |
| | | 953.67 nM | 5.9 | |
| | | 298.02 nM | 3.6 | |
| | | 93.13 nM | 2.07 | |
| | | 29.10 nM | 4.22 | |
| | | 9.09 nM | -0.68 | |
| | | 2.84 nM | 12.48 | |
| | | 0.80 nM | -0.53 | |
| 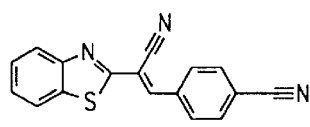 59-0130 | 287.34 | | | |
| | | 100.00 uM | 4.38 | |
| | | 31.25 uM | 8.35 | |
| | | 9.77 uM | 5.91 | |
| | | 3.05 uM | 4.98 | |
| | | 953.67 nM | 0.39 | |
| | | 298.02 nM | 8.66 | |
| | | 93.13 nM | 2.85 | |
| | | 29.10 nM | 3.6 | |
| | | 9.09 nM | 4.36 | |
| | | 2.84 nM | 8.96 | |
| | | 0.80 nM | 24.75 | |
| 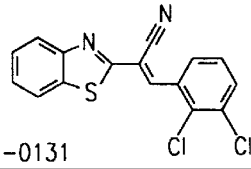 59-0131 | 331.22 | | | |
| | | 100.00 uM | 8.75 | |
| | | 31.25 uM | 0.12 | |
| | | 9.77 uM | -10.38 | |
| | | 3.05 uM | -6.39 | |
| | | 953.67 nM | -2.81 | |
| | | 298.02 nM | 1.61 | |
| | | 93.13 nM | -1.98 | |
| | | 29.10 nM | -2.59 | |
| | | 9.09 nM | 0.14 | |
| | | 2.84 nM | -5.77 | |
FIG. 3NN

| | | 0.80 | nM | -0.5 | |
|---|---|---|---|---|---|
| 59-0132 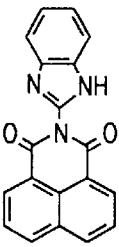 | 313.32 | | | | |
| | | 100.00 | uM | -17.1 | |
| | | 31.25 | uM | -14.81 | |
| | | 9.77 | uM | -14.37 | |
| | | 3.05 | uM | -12.92 | |
| | | 953.67 | nM | -13.54 | |
| | | 298.02 | nM | -10.38 | |
| | | 93.13 | nM | -3.65 | |
| | | 29.10 | nM | -7.66 | |
| | | 9.09 | nM | -6.18 | |
| | | 2.84 | nM | -9.97 | |
| | | 0.80 | nM | -2.81 | |
| 59-0133 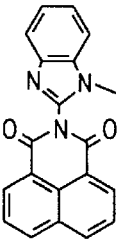 | 327.34 | | | | |
| | | 100.00 | uM | -16.04 | |
| | | 31.25 | uM | -16.91 | |
| | | 9.77 | uM | -17.31 | |
| | | 3.05 | uM | -16.7 | |
| | | 953.67 | nM | -9.34 | |
| | | 298.02 | nM | -12.69 | |
| | | 93.13 | nM | -11.23 | |
| | | 29.10 | nM | -17.74 | |
| | | 9.09 | nM | 6.02 | |
| | | 2.84 | nM | -4.71 | |
| | | 0.80 | nM | 0.55 | |
FIG. 300

| | | | | | |
|---|---|---|---|---|---|
| 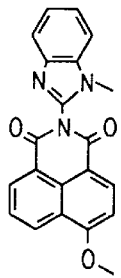 59-0134 | 357.37 | | | | |
| | | 100.00 | uM | | |
| | | 31.25 | uM | | |
| | | 9.77 | uM | | |
| | | 3.05 | uM | | |
| | | 953.67 | nM | | |
| | | 298.02 | nM | | |
| | | 93.13 | nM | | |
| | | 29.10 | nM | | |
| | | 9.09 | nM | | |
| | | 2.84 | nM | | |
| | | 0.80 | nM | | |
| 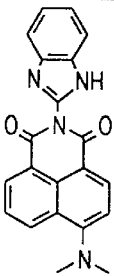 59-0135 | 356.39 | | | | |
| | | 100.00 | uM | -21.3 | |
| | | 31.25 | uM | -14.16 | |
| | | 9.77 | uM | -1.98 | |
| | | 3.05 | uM | 0.97 | |
| | | 953.67 | nM | 11.68 | |
| | | 298.02 | nM | -1.13 | |
| | | 93.13 | nM | -1.55 | |
| | | 29.10 | nM | -2.81 | |
| | | 9.09 | nM | 12.11 | |
| | | 2.84 | nM | -5.75 | |
| | | 0.80 | nM | 4.54 | |
| 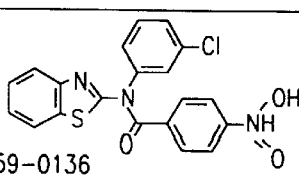 59-0136 | 411.87 | | | | |
| | | 100.00 | uM | | |
| | | 31.25 | uM | | |
| | | 9.77 | uM | | |
| | | 3.05 | uM | | |
| | | 953.67 | nM | | |
FIG. 3PP

| | | 298.02 | nM | | |
|---|---|---|---|---|---|
| | | 93.13 | nM | | |
| | | 29.10 | nM | | |
| | | 9.09 | nM | | |
| | | 2.84 | nM | | |
| | | 0.80 | nM | | |
| 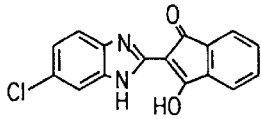 59-0137 | 296.71 | | | | |
| | | 100.00 | uM | | |
| | | 31.25 | uM | | |
| | | 9.77 | uM | | |
| | | 3.05 | uM | | |
| | | 953.67 | nM | | |
| | | 298.02 | nM | | |
| | | 93.13 | nM | | |
| | | 29.10 | nM | | |
| | | 9.09 | nM | | |
| | | 2.84 | nM | | |
| | | 0.80 | nM | | |
| 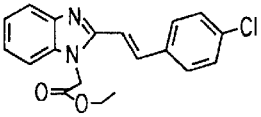 59-0138 | 340.81 | | | | |
| | | 100.00 | uM | -6.91 | |
| | | 31.25 | uM | -12.68 | |
| | | 9.77 | uM | 4.59 | |
| | | 3.05 | uM | 32.61 | |
| | | 953.67 | nM | 19.07 | |
| | | 298.02 | nM | 8.18 | |
| | | 93.13 | nM | 2.26 | |
| | | 29.10 | nM | 12.22 | |
| | | 9.09 | nM | 56.42 | |
| | | 2.84 | nM | 7.24 | |
| | | 0.80 | nM | 1.63 | |
| 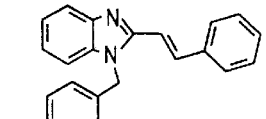 59-0139 | 340.43 | | | | |
| | | 100.00 | uM | 45.53 | |
| | | 31.25 | uM | 44.59 | |
| | | 9.77 | uM | 53.62 | |
| | | 3.05 | uM | 30.42 | |
| | | 953.67 | nM | 28.25 | |
| | | 298.02 | uM | 20.31 | |
| | | 93.13 | nM | 18.6 | |
FIG. 3QQ

| | | | | |
|---|---|---|---|---|
| | | 29.10 | nM | 14.4 |
| | | 9.09 | nM | 13.93 |
| | | 2.84 | nM | 18.61 |
| | | 0.80 | nM | 10.05 |
| 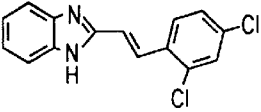 59-0140 | 289.17 | | | |
| | | 100.00 | uM | |
| | | 31.25 | uM | |
| | | 9.77 | uM | |
| | | 3.05 | uM | |
| | | 953.67 | nM | |
| | | 298.02 | nM | |
| | | 93.13 | nM | |
| | | 29.10 | nM | |
| | | 9.09 | nM | |
| | | 2.84 | nM | |
| | | 0.80 | nM | |
| 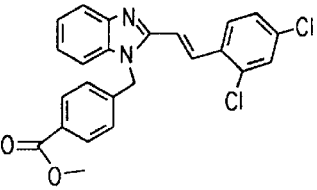 59-0141 | 437.33 | | | |
| | | 100.00 | uM | -6.76 |
| | | 31.25 | uM | 5.69 |
| | | 9.77 | uM | 19.85 |
| | | 3.05 | uM | 43.96 |
| | | 953.67 | nM | 44.73 |
| | | 298.02 | nM | 37.12 |
| | | 93.13 | nM | 24.36 |
| | | 29.10 | nM | 18.6 |
| | | 9.09 | nM | 26.7 |
| | | 2.84 | nM | 15.96 |
| | | 0.80 | nM | 7.87 |
| 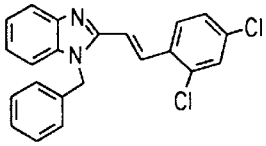 59-0142 | 379.29 | | | |
| | | 100.00 | uM | 9.43 |
| | | 31.25 | uM | 33.72 |
| | | 9.77 | uM | 47.33 |
| | | 3.05 | uM | 40.19 |
| | | 953.67 | nM | 36.53 |
| | | 298.02 | uM | 29.94 |
| | | 93.13 | nM | 22.11 |
FIG. 3RR

| | | | | |
|---|---|---|---|---|
| | | 29.10 | nM | 20.9 |
| | | 9.09 | nM | 19.14 |
| | | 2.84 | nM | 10.38 |
| | | 0.80 | nM | 17.12 |
| 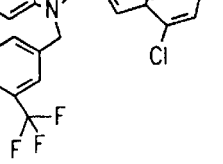 59-0143 | 447.29 | | | |
| | | 100.00 | uM | 0.4 |
| | | 31.25 | uM | 34.39 |
| | | 9.77 | uM | 42.21 |
| | | 3.05 | uM | 50.57 |
| | | 953.67 | nM | 36.94 |
| | | 298.02 | nM | 27.23 |
| | | 93.13 | nM | 16.99 |
| | | 29.10 | nM | 19.27 |
| | | 9.09 | nM | 14.42 |
| | | 2.84 | nM | 11.33 |
| | | 0.80 | nM | 23.72 |
| 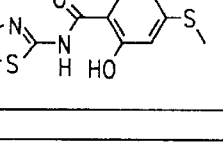 59-0144 | 316.40 | | | |
| | | 100.00 | uM | −14.59 |
| | | 31.25 | uM | −4.44 |
| | | 9.77 | uM | 47.1 |
| | | 3.05 | uM | 53.89 |
| | | 953.67 | nM | 43.11 |
| | | 298.02 | nM | 29.2 |
| | | 93.13 | nM | 18.5 |
| | | 29.10 | nM | 12.9 |
| | | 9.09 | nM | 5.54 |
| | | 2.84 | nM | 3.71 |
| | | 0.80 | nM | 5.87 |
| 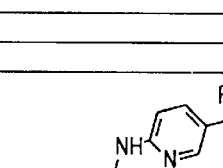 59-0145 | 350.27 | | | |
| | | 100.00 | uM | 435.91 |
| | | 31.25 | uM | 422.15 |
| | | 9.77 | uM | 446.93 |
| | | 3.05 | uM | 434.17 |
| | | 953.67 | nM | 238.34 |
| | | 298.02 | uM | 45.99 |
| | | 93.13 | nM | 9.22 |
| | | 29.10 | uM | 7.71 |
| | | 9.09 | nM | 0.11 |
FIG. 3SS

| | | | | | |
|---|---|---|---|---|---|
| | | 2.84 | nM | 6.27 | |
| | | 0.80 | nM | 3.55 | |
| 59-0146 | 246.27 | | | | |
| | | 100.00 | uM | -63.05 | |
| | | 31.25 | uM | 4.42 | |
| | | 9.77 | uM | -13.73 | |
| | | 3.05 | uM | -16.45 | |
| | | 953.67 | nM | -35.47 | |
| | | 298.02 | nM | -51.25 | |
| | | 93.13 | nM | -50.13 | |
| | | 29.10 | nM | -42.92 | |
| | | 9.09 | nM | -45.64 | |
| | | 2.84 | nM | -56.58 | |
| | | 0.80 | nM | -39.68 | |
| 59-0147 | 314.36 | | | | |
| | | 100.00 | uM | -85 | |
| | | 31.25 | uM | -85 | |
| | | 9.77 | uM | -80.29 | |
| | | 3.05 | uM | -41.67 | |
| | | 953.67 | nM | 78.69 | |
| | | 298.02 | nM | 269.13 | |
| | | 93.13 | nM | 323.59 | |
| | | 29.10 | nM | 339.88 | |
| | | 9.09 | nM | 270.48 | |
| | | 2.84 | nM | 245.58 | |
| | | 0.80 | nM | 180.33 | |
| 59-0148 | 291.35 | | | | |
| | | 100.00 | uM | -68.38 | |
| | | 31.25 | uM | -36.33 | |
| | | 9.77 | uM | -2.3 | |
| | | 3.05 | uM | 12.12 | |
| | | 953.67 | nM | -2.42 | |
| | | 298.02 | nM | -16.21 | |
| | | 93.13 | nM | -30.87 | |
| | | 29.10 | nM | -35.58 | |
| | | 9.09 | nM | -39.07 | |
| | | 2.84 | nM | -41.18 | |
| | | 0.80 | nM | -45.53 | |

FIG. 3TT

| | | | | |
|---|---|---|---|---|
| 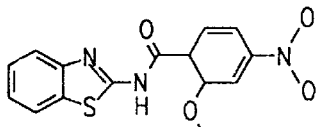 59-0149 | 329.33 | | | |
| | | 100.00 | uM | -16.9 |
| | | 31.25 | uM | -1.8 |
| | | 9.77 | uM | -0.53 |
| | | 3.05 | uM | 15.29 |
| | | 953.67 | nM | 78.78 |
| | | 298.02 | nM | 163.5 |
| | | 93.13 | nM | 223.57 |
| | | 29.10 | nM | 173.93 |
| | | 9.09 | nM | 122.3 |
| | | 2.84 | nM | 98.02 |
| | | 0.80 | nM | 69.06 |
| 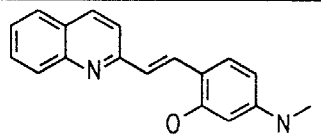 59-0150 | 304.39 | | | |
| | | 100.00 | uM | 63.32 |
| | | 31.25 | uM | 193.32 |
| | | 9.77 | uM | 419.26 |
| | | 3.05 | uM | 497.21 |
| | | 953.67 | nM | 295.19 |
| | | 298.02 | nM | 193.35 |
| | | 93.13 | nM | 99.46 |
| | | 29.10 | nM | 69.96 |
| | | 9.09 | nM | 59 |
| | | 2.84 | nM | 52.16 |
| | | 0.80 | nM | 48.75 |
| 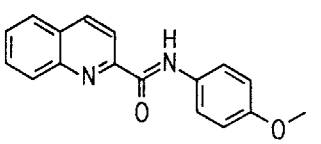 59-0151 | 278.311 | | | |
| 59-0151 | | 100.00 | uM | -6.660 |
| | | 31.25 | uM | 16.240 |
| | | 9.77 | uM | 18.300 |
| | | 3.05 | uM | 11.690 |
| | | 953.67 | nM | 8.500 |
| | | 298.02 | nM | 9.070 |
| | | 93.13 | nM | 6.110 |
| | | 29.10 | nM | 5.880 |
| | | 9.09 | nM | 7.700 |
| | | 2.84 | nM | 2.000 |
| | | 0.80 | nM | 1.210 |
FIG. 3UU

| | | | | |
|---|---|---|---|---|
| 59-0152 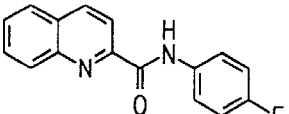 | 266.275 | | | |
| 59-0152 | | 100.00 uM | -6.890 | |
| | | 31.25 uM | 12.490 | |
| | | 9.77 uM | 21.950 | |
| | | 3.05 uM | 12.820 | |
| | | 953.67 nM | 7.350 | |
| | | 298.02 nM | 4.290 | |
| | | 93.13 nM | 9.750 | |
| | | 29.10 nM | 4.860 | |
| | | 9.09 nM | 1.320 | |
| | | 2.84 nM | 4.280 | |
| | | 0.80 nM | 4.160 | |
| 59-0153 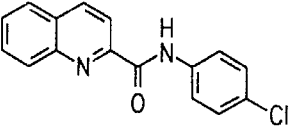 | 282.73 | | | |
| 59-0153 | | 100.00 uM | -4.150 | |
| | | 31.25 uM | -0.390 | |
| | | 9.77 uM | 11.120 | |
| | | 3.05 uM | 14.540 | |
| | | 953.67 nM | 9.520 | |
| | | 298.02 nM | 11.570 | |
| | | 93.13 nM | -0.160 | |
| | | 29.10 nM | 1.550 | |
| | | 9.09 nM | -0.960 | |
| | | 2.84 nM | 4.730 | |
| | | 0.80 nM | 5.650 | |
| 59-0154 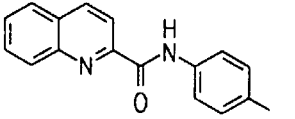 | 262.312 | | | |
| 59-0154 | | 100.00 uM | 0.290 | |
| | | 31.25 uM | 24.670 | |
| | | 9.77 uM | 15.680 | |
| | | 3.05 uM | 14.540 | |
| | | 953.67 nM | 13.170 | |
| | | 298.02 nM | 5.540 | |
| | | 93.13 nM | 2.690 | |
| | | 29.10 nM | -1.190 | |
| | | 9.09 nM | 2.460 | |
| | | 2.84 nM | 4.170 | |
| | | 0.80 nM | 1.890 | |
FIG. 3VV

| | | | | | | |
|---|---|---|---|---|---|---|
| 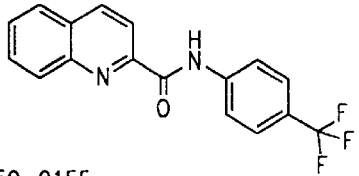 59-0155 | 316.282 | | | | | |
| 59-0155 | | 100.00 | uM | -2.950 | | |
| | | 31.25 | uM | 1.900 | | |
| | | 9.77 | uM | -9.450 | | |
| | | 3.05 | uM | -0.220 | | |
| | | 953.67 | nM | 0.690 | | |
| | | 298.02 | nM | 5.090 | | |
| | | 93.13 | nM | -3.250 | | |
| | | 29.10 | nM | 0.530 | | |
| | | 9.09 | nM | -1.900 | | |
| | | 2.84 | nM | 9.480 | | |
| | | 0.80 | nM | -1.130 | | |
| 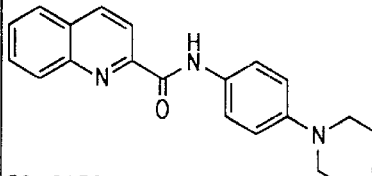 59-0156 | 333.391 | | | | | |
| 59-0156 | | 100.00 | uM | 5.840 | | |
| | | 31.25 | uM | 2.050 | | |
| | | 9.77 | uM | 7.960 | | |
| | | 3.05 | uM | 6.890 | | |
| | | 953.67 | nM | -0.370 | | |
| | | 298.02 | nM | -1.880 | | |
| | | 93.13 | nM | -3.550 | | |
| | | 29.10 | nM | -7.340 | | |
| | | 9.09 | nM | -1.590 | | |
| | | 2.84 | nM | 2.650 | | |
| | | 0.80 | nM | 2.500 | | |
| 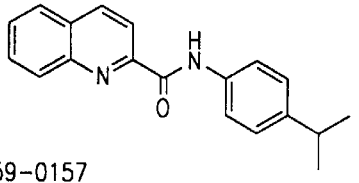 59-0157 | 290.366 | | | | | |
| 59-0157 | | 100.00 | uM | -6.440 | | |
| | | 31.25 | uM | 14.920 | | |
| | | 9.77 | uM | 19.930 | | |
| | | 3.05 | uM | 11.440 | | |
| | | 953.67 | nM | 8.570 | | |
| | | 298.02 | nM | -7.190 | | |
| | | 93.13 | nM | 0.080 | | |
| | | 29.10 | nM | -0.230 | | |
| | | 9.09 | nM | -4.460 | | |
| | | 2.84 | nM | 2.200 | | |
| | | 0.80 | nM | 9.920 | | |
FIG. 3WW

| | | | | | | |
|---|---|---|---|---|---|---|
| 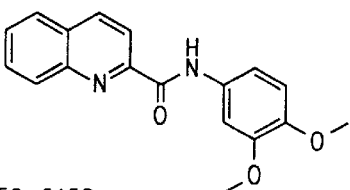 59-0158 | 308.337 | | | | | |
| 59-0158 | | 100.00 | uM | 5.980 | | |
| | | 31.25 | uM | 3.720 | | |
| | | 9.77 | uM | 16.140 | | |
| | | 3.05 | uM | 27.060 | | |
| | | 953.67 | nM | 9.930 | | |
| | | 298.02 | nM | 11.900 | | |
| | | 93.13 | nM | 2.810 | | |
| | | 29.10 | nM | 3.110 | | |
| | | 9.09 | nM | 0.690 | | |
| | | 2.84 | nM | 1.900 | | |
| | | 0.80 | nM | 7.970 | | |
| 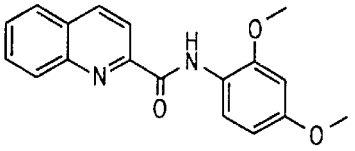 59-0159 | 308.337 | | | | | |
| 59-0159 | | 100.00 | uM | 2.790 | | |
| | | 31.25 | uM | 13.530 | | |
| | | 9.77 | uM | 4.700 | | |
| | | 3.05 | uM | 10.910 | | |
| | | 953.67 | nM | 2.800 | | |
| | | 298.02 | nM | 9.710 | | |
| | | 93.13 | nM | 4.830 | | |
| | | 29.10 | nM | 0.650 | | |
| | | 9.09 | nM | 5.900 | | |
| | | 2.84 | nM | 6.610 | | |
| | | 0.80 | nM | 6.250 | | |
| 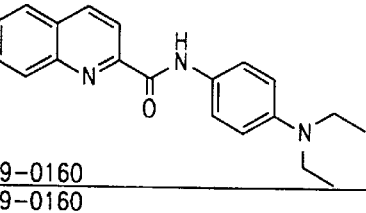 59-0160 | 319.408 | | | | | |
| 59-0160 | | 100.00 | uM | -5.060 | | |
| | | 31.25 | uM | -3.390 | | |
| | | 9.77 | uM | 5.300 | | |
| | | 3.05 | uM | 15.910 | | |
| | | 953.67 | nM | 6.610 | | |
| | | 298.02 | nM | 11.380 | | |
| | | 93.13 | nM | 4.460 | | |
| | | 29.10 | nM | 3.520 | | |
| | | 9.09 | nM | 4.700 | | |
| | | 2.84 | nM | -0.650 | | |
| | | 0.80 | nM | 7.560 | | |
FIG. 3XX

| | | | | | | |
|---|---|---|---|---|---|---|
| 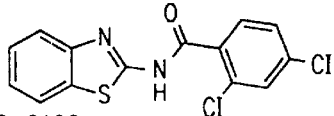 59-0196 | 323.201 | | | | | |
| 59-0196 | | 100.00 uM | | | | |
| | | 31.25 uM | | | | |
| | | 9.77 uM | | | | |
| | | 3.05 uM | | | | |
| | | 953.67 nM | | | | |
| | | 298.02 nM | | | | |
| | | 93.13 nM | | | | |
| | | 29.10 nM | | | | |
| | | 9.09 nM | | | | |
| | | 2.84 nM | | | | |
| | | 0.80 nM | | | | |
| 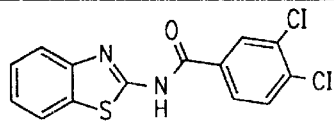 59-0197 | 323.201 | | | | | |
| 59-0197 | | 100.00 uM | | | | |
| | | 31.25 uM | | | | |
| | | 9.77 uM | | | | |
| | | 3.05 uM | | | | |
| | | 953.67 nM | | | | |
| | | 298.02 nM | | | | |
| | | 93.13 nM | | | | |
| | | 29.10 nM | | | | |
| | | 9.09 nM | | | | |
| | | 2.84 nM | | | | |
| | | 0.80 nM | | | | |
| 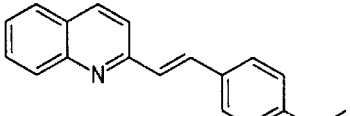 59-0198 | 261.324 | | | | | |
| 59-0198 | | 100.00 uM | | | | |
| | | 31.25 uM | | | | |
| | | 9.77 uM | | | | |
| | | 3.05 uM | | | | |
| | | 953.67 nM | | | | |
| | | 298.02 nM | | | | |
| | | 93.13 nM | | | | |
| | | 29.10 nM | | | | |
| | | 9.09 nM | | | | |
| | | 2.84 nM | | | | |
| | | 0.80 nM | | | | |
| 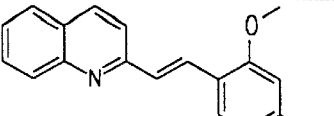 59-0199 | 291.35 | | | | | |
| 59-0199 | | 100.00 uM | | | | |
| | | 31.25 uM | | | | |
FIG. 3YY

| | | | | | | | |
|---|---|---|---|---|---|---|---|
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 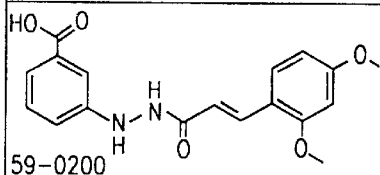 59-0200 | 342.351 | | | | | | |
| 59-0200 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 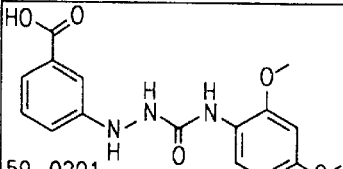 59-0201 | 331.328 | | | | | | |
| 59-0201 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 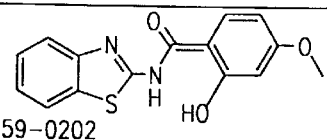 59-0202 | 300.336 | | | | | | |
| 59-0202 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
FIG. 3ZZ

| | | | | | | | |
|---|---|---|---|---|---|---|---|
| | | 9.09 | nM | | | | |
| | | 2.84 | nM | | | | |
| | | 0.80 | nM | | | | |
| 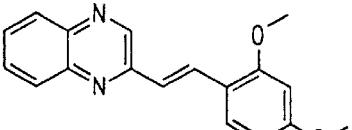 59-0203 | 292.338 | | | | | | |
| 59-0203 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 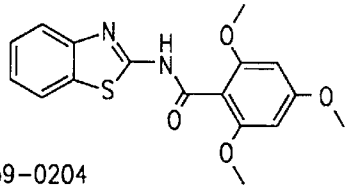 59-0204 | 344.389 | | | | | | |
| 59-0204 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 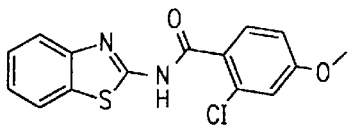 59-0205 | 318.782 | | | | | | |
| 59-0205 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
FIG. 3AAA

| | | | | | | | |
|---|---|---|---|---|---|---|---|
| 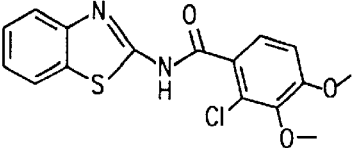 59-0206 | 348.808 | | | | | | |
| 59-0206 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 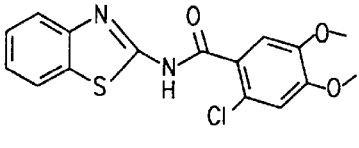 59-0207 | 348.808 | | | | | | |
| 59-0207 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 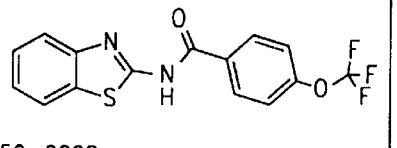 59-0208 | 338.307 | | | | | | |
| 59-0208 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
FIG. 3BBB

| | | | | | | | |
|---|---|---|---|---|---|---|---|
| 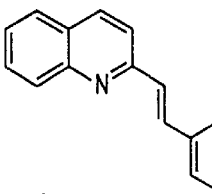 59-0209 | 247.297 | | | | | | |
| 59-0209 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 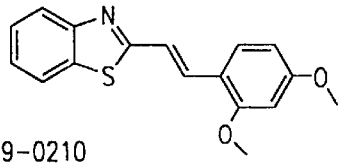 59-0210 | 297.376 | | | | | | |
| 59-0210 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 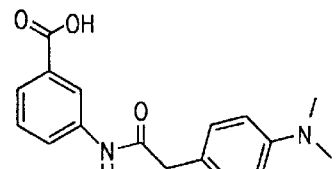 59-8000 | 298.342 | | | | | | |
| 59-8000 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
FIG. 3CCC

| | | | | | | | |
|---|---|---|---|---|---|---|---|
| 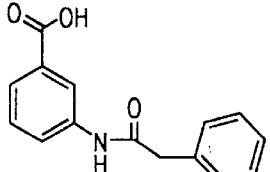 59-8001 | 255.273 | | | | | | |
| 59-8001 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 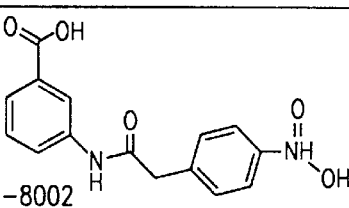 59-8002 | 302.286 | | | | | | |
| 59-8002 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 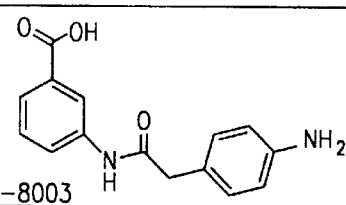 59-8003 | 270.288 | | | | | | |
| 59-8003 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
FIG. 3DDD

| Structure | MW | Conc | Unit | | | | |
|---|---|---|---|---|---|---|---|
| 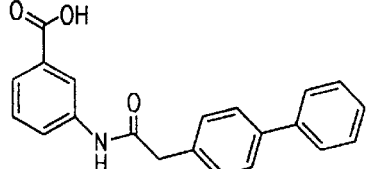 59-8004 | 331.371 | | | | | | |
| 59-8004 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 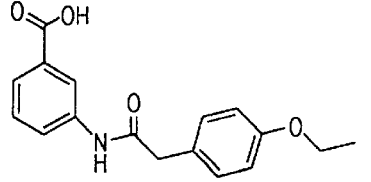 59-8005 | 299.326 | | | | | | |
| 59-8005 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 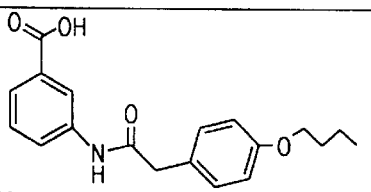 59-8006 | 327.38 | | | | | | |
| 59-8006 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
FIG. 3EEE

| | | | | | | | |
|---|---|---|---|---|---|---|---|
| 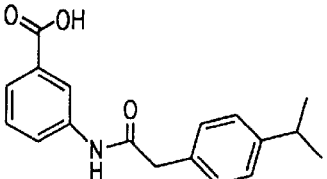 59-8007 | 297.354 | | | | | | |
| 59-8007 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 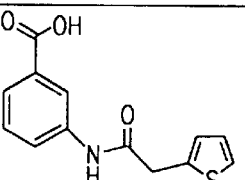 59-8008 | 261.299 | | | | | | |
| 59-8008 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
| | | 2.84 | nM | | | | |
| | | 0.80 | nM | | | | |
| 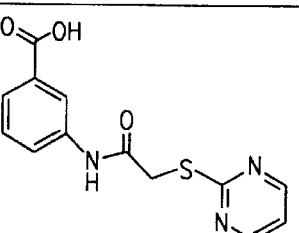 59-8009 | 289.313 | | | | | | |
| 59-8009 | | 100.00 | uM | | | | |
| | | 31.25 | uM | | | | |
| | | 9.77 | uM | | | | |
| | | 3.05 | uM | | | | |
| | | 953.67 | nM | | | | |
| | | 298.02 | nM | | | | |
| | | 93.13 | nM | | | | |
| | | 29.10 | nM | | | | |
| | | 9.09 | nM | | | | |
FIG. 3FFF

| | | | | | | |
|---|---|---|---|---|---|---|
| | | 2.84 | nM | | | |
| | | 0.80 | nM | | | |
| 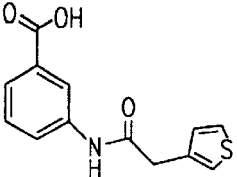 59-8010 | 261.299 | | | | | |
| 59-8010 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
| | | 93.13 | nM | | | |
| | | 29.10 | nM | | | |
| | | 9.09 | nM | | | |
| | | 2.84 | nM | | | |
| | | 0.80 | nM | | | |
| 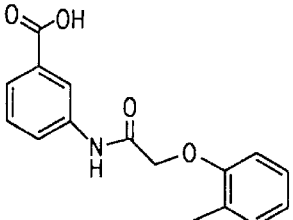 59-8011 | 285.299 | | | | | |
| 59-8011 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
| | | 93.13 | nM | | | |
| | | 29.10 | nM | | | |
| | | 9.09 | nM | | | |
| | | 2.84 | nM | | | |
| | | 0.80 | nM | | | |
| 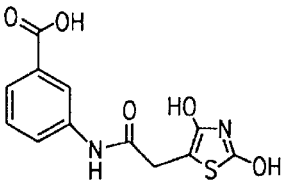 59-8012 | 294.285 | | | | | |
| 59-8012 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
FIG. 3GGG

| | | | | | | |
|---|---|---|---|---|---|---|
| | | 93.13 | nM | | | |
| | | 29.10 | nM | | | |
| | | 9.09 | nM | | | |
| | | 2.84 | nM | | | |
| | | 0.80 | nM | | | |
| 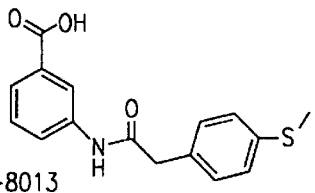 59-8013 | 301.364 | | | | | |
| 59-8013 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
| | | 93.13 | nM | | | |
| | | 29.10 | nM | | | |
| | | 9.09 | nM | | | |
| | | 2.84 | nM | | | |
| | | 0.80 | nM | | | |
| 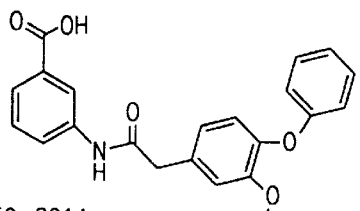 59-8014 | 377.396 | | | | | |
| 59-8014 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
| | | 93.13 | nM | | | |
| | | 29.10 | nM | | | |
| | | 9.09 | nM | | | |
| | | 2.84 | nM | | | |
| | | 0.80 | nM | | | |
| 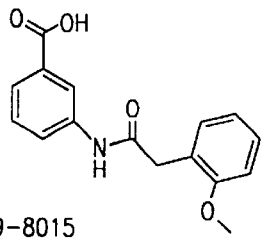 59-8015 | 285.299 | | | | | |
| 59-8015 | | 100.00 | uM | | | |
| | | 31.25 | uM | | | |
| | | 9.77 | uM | | | |
| | | 3.05 | uM | | | |
FIG. 3HHH

| | | 953.67 | nM | | | |
|---|---|---|---|---|---|---|
| | | 298.02 | nM | | | |
| | | 93.13 | nM | | | |
| | | 29.10 | nM | | | |
| | | 9.09 | nM | | | |
| | | 2.84 | nM | | | |
| | | 0.80 | nM | | | |
| 59-8016 (structure) | 285.299 | | | | | |
| 59-8016 | | 100.00 | uM | | | |
| | | 31.25 | uM | | | |
| | | 9.77 | uM | | | |
| | | 3.05 | uM | | | |
| | | 953.67 | nM | | | |
| | | 298.02 | nM | | | |
| | | 93.13 | nM | | | |
| | | 29.10 | nM | | | |
| | | 9.09 | nM | | | |
| | | 2.84 | nM | | | |
| | | 0.80 | nM | | | |

FIG. 3III

| CHEMISTRY | CONCENTRATION | | ABA-S |
|---|---|---|---|
| 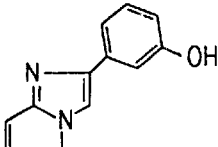 51-2229 | | | |
| 51-2229 | 100.00 | uM | 125.320 |
| | 10.00 | | 28.260 |
| 210.236 | 2.00 | | 20.140 |
| | 0.40 | | -9.740 |
| | 0.08 | | -9.710 |
| 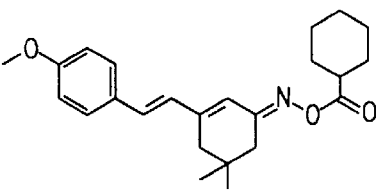 92-3052 | | | |
| 92-3052 | 131.056 | uM | -9.28 |
| | 13.106 | | 113.80 |
| 381.516 | 2.621 | | 12.61 |
| | 0.524 | | 20.25 |
| | 0.105 | | 24.45 |
| 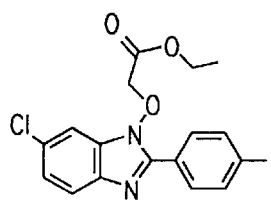 92-3390 | | | |
| 92-3390 | 145.012 | uM | -8.05 |
| | 14.501 | | 31.57 |
| 344.798 | 2.900 | | 139.68 |
| | 0.580 | | 49.82 |
| | 0.116 | | 21.01 |
| 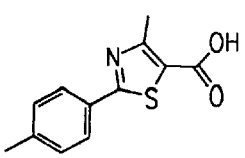 92-3552 | | | |
| 92-3552 | 214.326 | uM | 108.15 |
FIG. 4A

| | | | |
|---|---|---|---|
| | | 21.433 | 69.74 |
| | 233.289 | 4.287 | 31.59 |
| | | 0.857 | 39.70 |
| | | 0.171 | 18.29 |
| 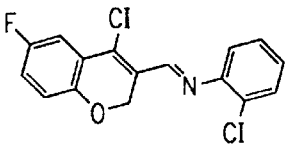 92-6353 | | | |
| 92-6353 | | 155.199 uM | |
| | | 31.040 | 204.14 |
| | 322.166 | 15.520 | 154.94 |
| | | 3.104 | 28.09 |
| | | 1.552 | |
| | | 0.310 | 3.53 |
| 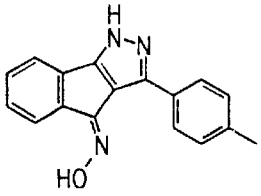 92-8007 | | | |
| 92-8007 | | 181.613 uM | −16.65 |
| | | 36.323 | 58.65 |
| | 275.311 | 18.161 | 142.33 |
| | | 3.632 | 45.65 |
| | | 1.816 | |
| | | 0.363 | 4.47 |
| 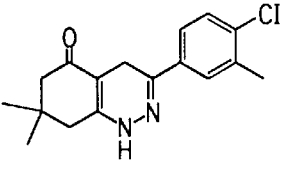 92-8215 | | | |
| 92-8215 | | 165.123 uM | 32.90 |
| | | 33.025 | 151.06 |
| | 302.805 | 16.512 | 132.29 |
| | | 3.302 | 59.90 |
| | | 1.651 | |
| | | 0.330 | 23.34 |
FIG. 4B

| | | | | |
|---|---|---|---|---|
| 92-8258 | | | | |
| 92-8258 | | 162.102 | uM | -16.65 |
| | | 32.420 | | 157.44 |
| | 308.447 | 16.210 | | 101.04 |
| | | 3.242 | | 39.02 |
| | | 1.621 | | |
| | | 0.324 | | 12.78 |
| 92-8362 | | | | |
| 92-8362 | | 154.647 | uM | 136.79 |
| | | 30.929 | | 137.00 |
| | 323.318 | 15.465 | | 65.02 |
| | | 3.093 | | 17.34 |
| | | 1.546 | | |
| | | 0.309 | | 0.41 |
| 92-8372 | | | | |
| 92-8372 | | 150.045 | uM | 63.76 |
| | | 30.009 | | 134.71 |
| | 333.234 | 15.004 | | 92.06 |
| | | 3.001 | | 31.35 |
| | | 1.500 | | |
| | | 0.300 | | 13.20 |
| 92-9183 | | | | |

FIG. 4C

| | | | |
|---|---|---|---|
| 92-9183 | | 137.568 | uM | -22.80 |
| | | 13.757 | | 16.61 |
| | 363.457 | 2.751 | | 101.96 |
| | | 1.376 | | |
| | | 0.550 | | 58.17 |
| | | 0.110 | | 38.47 |
| 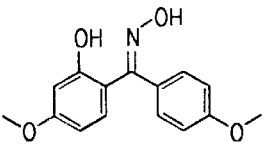 93-0215 | | | | |
| 93-0215 | | 182.957 | uM | 115.230 |
| | | 18.296 | | 88.110 |
| | 273.288 | 3.659 | | 20.870 |
| | | 0.732 | | -28.680 |
| | | 0.146 | | 5.250 |
| 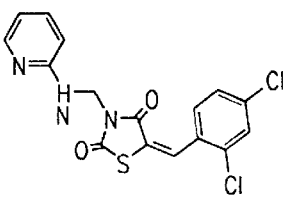 93-0399 | | | | |
| 93-0399 | | 131.491 | uM | 128.130 |
| | | 13.149 | | 38.560 |
| | 380.253 | 2.630 | | 41.240 |
| | | 0.526 | | -4.910 |
| | | 0.105 | | 3.910 |
| 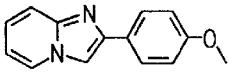 93-0587 | | | | |
| 93-0587 | | 222.953 | uM | 178.130 |
| | | 22.295 | | 60.410 |
| | 224.263 | 4.459 | | -0.180 |
| | | 0.892 | | -3.470 |
| | | 0.178 | | -8.460 |
| 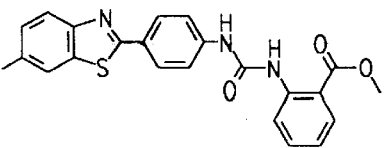 93-1327 | | | | |
| 93-1327 | | 119.764 | uM | -42.000 |
| | | 11.976 | | 119.130 |
| | 417.487 | 2.395 | | 67.930 |
| | | 0.479 | | 8.520 |
FIG. 4D

| Structure | | | |
|---|---|---|---|
| | | 0.096 | 14.870 |
|  93-1340 | | | |
| 93-1340 | | 196.576 uM | -31.290 |
| | | 19.658 | 127.340 |
| | 254.355 | 3.932 | 35.710 |
| | | 0.786 | 37.630 |
| | | 0.157 | 7.280 |
| 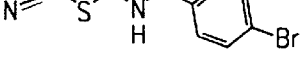 93-1474 | | | |
| 93-1474 | | 145.940 uM | -45.110 |
| | | 14.594 | 110.290 |
| | 342.607 | 2.919 | 35.080 |
| | | 0.584 | 109.040 |
| | | 0.117 | 40.130 |
| 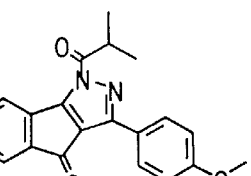 93-1766 | | | |
| 93-1766 | | 144.348 uM | |
| | | 14.435 | |
| | 346.366 | 2.887 | |
| | | 0.577 | |
| | | 0.115 | |
| 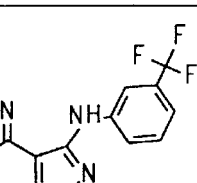 93-1866 | | | |
| 93-1866 | | 148.214 uM | 75.940 |
| | | 14.821 | 173.150 |
FIG. 4E

| Compound | | | | |
|---|---|---|---|---|
| 850-7377 | | | | |
| 850-7377 | | 131.062 | uM | -50.32 |
| | | 13.106 | | 68.27 |
| | 381.498 | 2.621 | | 116.61 |
| | | 0.524 | | 61.26 |
| | | 0.105 | | 25.86 |
| 850-7413 | | | | |
| 850-7413 | | 111.964 | uM | -40.44 |
| | | 11.196 | | -2.55 |
| | 446.572 | 2.239 | | 157.01 |
| | | 0.448 | | 78.73 |
| | | 0.090 | | 23.91 |
| 850-7449 | | | | |
| 850-7449 | | 69.938 | uM | -42.42 |
| | | 6.994 | | 73.79 |
| | 714.923 | 1.399 | | 112.16 |
| | | 0.280 | | 75.24 |
| | | 0.056 | | 26.36 |

FIG. 4F

| | | | |
|---|---|---|---|
| 93-7485 | | | |
| 93-7485 | 143.099 uM | | -42.91 |
| | 14.310 | | 28.36 |
| 349.409 | 2.862 | | 153.04 |
| | 0.572 | | 74.27 |
| | 0.114 | | 50.28 |
| 93-7991 | | | |
| 93-7991 | 127.367 uM | | -16.87 |
| | 12.737 | | 8.95 |
| 392.585 | 2.547 | | 105.51 |
| | 0.509 | | 47.53 |
| | 0.102 | | 54.26 |
| 850-8170 | | | |
| 850-8170 | 101.513 uM | | -33.79 |
| | 10.151 | | 158.65 |
| 492.55 | 2.030 | | 126.27 |
| | 0.406 | | 43.05 |
| | 0.061 | | 50.00 |

| Structure / ID | | | | |
|---|---|---|---|---|
| 850-8205 | | | | |
| 850-8205 | | 104.478 | uM | -39.52 |
| | | 10.448 | | 51.18 |
| | 478.57 | 2.090 | | 163.82 |
| | | 0.418 | | 106.06 |
| | | 0.084 | | 73.68 |
| CHIRAL 850-8241 | | | | |
| 850-8241 | | 82.279 | uM | -2.07 |
| | | 8.226 | | 181.77 |
| | 607.685 | 1.646 | | 118.23 |
| | | 0.329 | | 66.73 |
| | | 0.066 | | 36.14 |
| 850-8278 | | | | |
| 850-8278 | | 139.101 | uM | -40.09 |
| | | 13.910 | | 39.00 |
| | 359.451 | 2.782 | | 182.38 |
| | | 0.556 | | 122.84 |
| | | 0.111 | | 78.90 |
| 850-8387 | | | | |

| | | | | |
|---|---|---|---|---|
| 850-8387 | | 122.392 | uM | −17.06 |
| | | 12.239 | | 130.31 |
| | 408.523 | 2.448 | | 129.75 |
| | | 0.490 | | 62.69 |
| | | 0.098 | | 40.74 |
| 850-8459 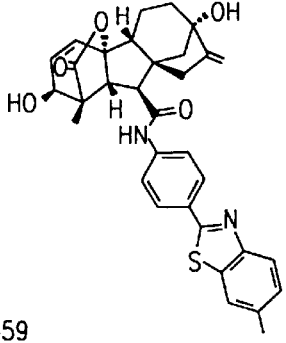 | | | | |
| 850-8459 | | 87.921 | uM | −21.13 |
| | | 8.792 | | 11.30 |
| | 568.692 | 1.758 | | 131.92 |
| | | 0.352 | | 71.13 |
| | | 0.070 | | 58.55 |
| 850-8613 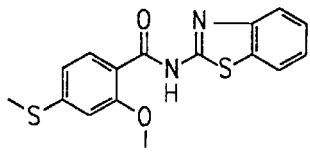 | | | | |
| 850-8613 | | 151.319 | uM | −26.05 |
| | | 15.132 | | 85.55 |
| | 330.428 | 3.026 | | 381.37 |
| | | 0.605 | | 255.32 |
| | | 0.121 | | 122.93 |
| 850-8637 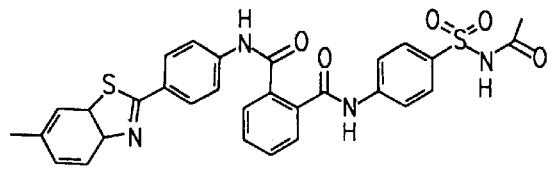 | | | | |
| 850-8637 | | 85.518 | uM | −25.17 |
| | | 8.552 | | 33.35 |
| | 584.673 | 1.710 | | 122.49 |
| | | 0.342 | | 57.19 |
| | | 0.068 | | 37.42 |
FIG. 4I

| Compound | | | | |
|---|---|---|---|---|
| 850-8889 | | | | |
| 850-8889 | | 111.493 | uM | -17.470 |
| | | 11.149 | | 142.970 |
| | 448.457 | 2.230 | | 74.150 |
| | | 0.446 | | 21.010 |
| | | 0.089 | | 8.530 |
| 850-8964 | | | | |
| 850-8964 | | 95.156 | uM | -30.92 |
| | | 9.516 | | 44.99 |
| | 525.454 | 1.903 | | 126.29 |
| | | 0.381 | | 49.84 |
| | | 0.076 | | 44.99 |
| 850-9071 | | | | |
| 850-9071 | | 109.998 | uM | -24.620 |
| | | 11.000 | | 84.120 |
| | 454.552 | 2.200 | | 149.030 |
| | | 0.440 | | 54.540 |

FIG. 4J

| | | | |
|---|---|---|---|
| | | 0.088 | 23.540 |
| 850-9106 [structure] | | | |
| 850-9106 | | 100.000 uM | -15.710 |
| | | 10.000 | 99.820 |
| | 499.999 | 2.000 | 111.960 |
| | | 0.400 | 74.500 |
| | | 0.080 | 23.150 |
| 850-9142 [structure] | | | |
| 850-9142 | | 85.596 uM | -14.980 |
| | | 8.560 | 165.770 |
| | 584.138 | 1.712 | 66.650 |
| | | 0.342 | 27.780 |
| | | 0.068 | 0.670 |
| 850-9179 [structure] | | | |
| 850-9179 | | 105.357 uM | -24.630 |
| | | 10.536 | 105.200 |
| | 474.579 | 2.107 | 89.280 |
| | | 0.421 | 46.110 |
| | | 0.064 | 19.160 |
| 850-9212 [structure] | | | |
| 850-9212 | | 92.139 uM | -26.580 |
| | | 9.214 | 40.900 |
| | 542.657 | 1.843 | 111.690 |
| | | 0.369 | 76.950 |
| | | 0.074 | 30.840 |

FIG. 4K

| | | | |
|---|---|---:|---|
| 850-9287 (structure) | | | |
| 850-9287 | | 147.170 | uM |
| | | 14.717 | |
| | 339.744 | 2.943 | |
| | | 0.589 | |
| | | 0.118 | |
| 850-9356 (structure) | | | |
| 850-9356 | | 99.506 | uM |
| | | 9.951 | |
| | 502.482 | 1.990 | |
| | | 0.396 | |
| | | 0.080 | |
| 850-9467 (structure) | | | |
| 850-9467 | | 120.646 | uM |
| | | 12.065 | |
| | 414.436 | 2.413 | |
| | | 0.483 | |
| | | 0.097 | |

| |
|---:|
| −15.82 |
| 15.82 |
| 130.71 |
| 91.11 |
| 69.05 |
| −24.650 |
| 83.140 |
| 168.810 |
| 45.470 |
| 9.740 |
| −19.800 |
| 112.990 |
| 122.730 |
| 43.520 |
| 33.140 |

FIG. 4L

| | | |
|---|---|---|
| 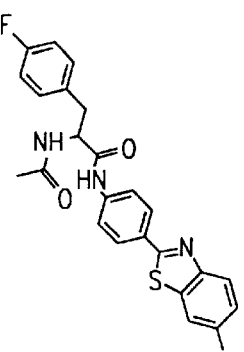 850-9576 | | |
| 850-9576 | 111.724 uM | −27.430 |
| | 11.172 | 90.560 |
| 447.532 | 2.234 | 101.610 |
| | 0.447 | 44.900 |
| | 0.089 | 19.930 |
| 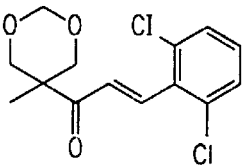 895-0262 | | |
| 895-0262 | 166.019 uM | −19.18 |
| | 33.204 | −12.60 |
| 301.169 | 16.602 | 148.28 |
| | 3.320 | −2.23 |
| | 0.332 | −3.07 |
| 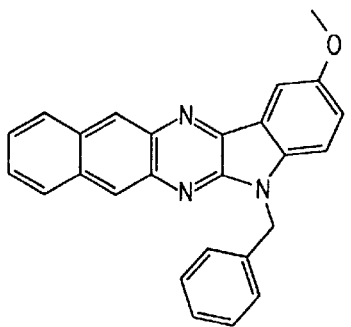 895-0268 | | |
| 895-0268 | 128.383 uM | −18.87 |
| | 25.677 | 40.25 |
| 369.458 | 12.836 | 169.96 |
| | 2.568 | 195.29 |
| | 0.257 | 14.02 |
FIG. 4M

| | | | |
|---|---|---|---|
| 895-0594 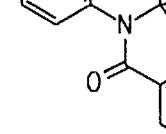 | | | |
| 895-0594 | | 120.896 uM | −21.63 |
| | | 12.090 | 25.89 |
| | 413.58 | 2.418 | 122.10 |
| | | 0.484 | 75.32 |
| | | 0.097 | 39.42 |
| 895-0857 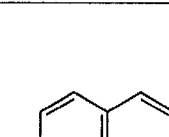 | | | |
| 895-0857 | | 159.026 uM | −30.46 |
| | | 15.903 | 146.74 |
| | 314.407 | 3.181 | 74.54 |
| | | 0.636 | 25.82 |
| | | 0.127 | 3.66 |
| 895-0964 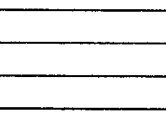 | | | |
| 895-0964 | | 162.655 uM | −31.06 |
| | | 16.265 | 325.06 |
| | 307.393 | 3.253 | 87.51 |
| | | 0.651 | 40.39 |
| | | 0.130 | 16.03 |
FIG. 4N

| | | | | |
|---|---|---|---|---|
| 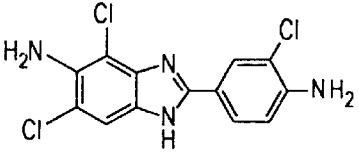 895-1161 | | | | |
| 895-1161 | | 152.625 | uM | -5.51 |
| | | 15.263 | | 109.31 |
| | 327.602 | 3.053 | | 56.06 |
| | | 0.611 | | 29.49 |
| | | 0.122 | | 24.71 |
| 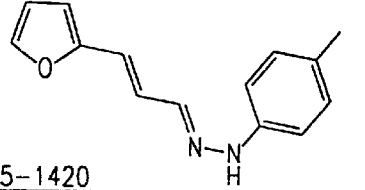 895-1420 | | | | |
| 895-1420 | | 220.965 | uM | -19.47 |
| | | 22.097 | | 110.90 |
| | 226.279 | 4.419 | | 49.94 |
| | | 0.884 | | 33.65 |
| | | 0.177 | | 20.06 |
| 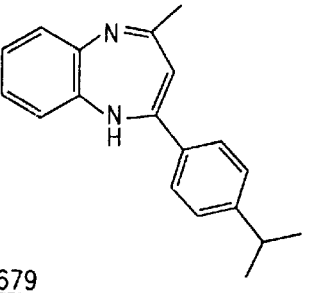 895-1679 | | | | |
| 895-1679 | | 180.910 | uM | -30.36 |
| | | 18.091 | | 111.72 |
| | 276.383 | 3.618 | | 102.83 |
| | | 0.724 | | 18.01 |
| | | 0.145 | | 0.44 |
| 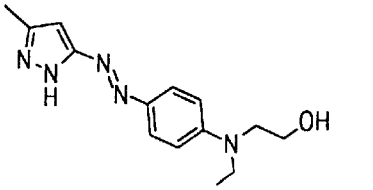 895-1691 | | | | |
| 895-1691 | | 182.992 | uM | -16.29 |
| | | 18.292 | | 50.84 |
| | 273.34 | 3.658 | | 105.70 |
FIG. 40

| | | | | |
|---|---|---|---|---|
| | | 0.732 | | 60.23 |
| | | 0.146 | | 23.42 |
| 895-1754 (structure) | | | | |
| 895-1754 | | 194.295 | uM | -31.44 |
| | | 19.430 | | 132.78 |
| | 257.341 | 3.886 | | 75.39 |
| | | 0.777 | | 39.30 |
| | | 0.155 | | 16.19 |
| 895-1888 (structure) | | | | |
| 895-1888 | | 212.504 | uM | -33.65 |
| | | 21.250 | | 29.75 |
| | 235.286 | 4.250 | | 148.84 |
| | | 0.850 | | 73.77 |
| | | 0.170 | | 28.14 |
| 895-2474 (structure) | | | | |
| 895-2474 | | 184.952 | uM | -20.74 |
| | | 18.495 | | 128.69 |
| | 270.335 | 3.699 | | 66.37 |
| | | 0.740 | | 43.27 |
| | | 0.148 | | 19.44 |
| 895-2475 (structure) | | | | |
| 895-2475 | | 162.159 | uM | 265.41 |
| | | 16.216 | | 287.86 |
| | 308.337 | 3.243 | | 227.34 |
| | | 0.649 | | 65.40 |
| | | 0.130 | | 28.96 |

FIG. 4P

| | | | |
|---|---|---|---|
| 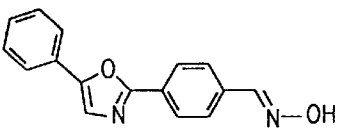 895-2544 | | | |
| 895-2544 | | 189.186 uM | 17.53 |
| | | 18.919 | 136.50 |
| | 264.284 | 3.784 | 59.15 |
| | | 0.757 | 24.75 |
| | | 0.151 | 11.86 |
| 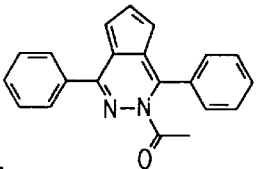 895-3113 | | | |
| 895-3113 | | 160.067 uM | -22.22 |
| | | 16.007 | 224.52 |
| | 312.372 | 3.201 | 68.46 |
| | | 0.640 | 43.36 |
| | | 0.128 | 30.56 |
| 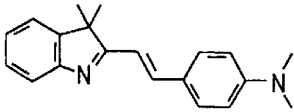 895-3306 | | | |
| 895-3306 | | 172.170 uM | -23.24 |
| | | 17.217 | 38.63 |
| | 290.41 | 3.443 | 333.10 |
| | | 0.689 | 164.63 |
| | | 0.136 | 64.33 |
| 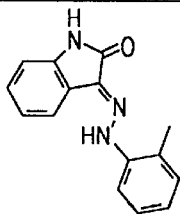 895-3810 | | | |
| 895-3810 | | 196.973 uM | 89.79 |
| | | 19.897 | 106.75 |
| | 251.289 | 3.979 | 73.78 |
| | | 0.796 | 33.45 |
| | | 0.159 | 16.86 |
FIG. 4Q

| Compound | | | | |
|---|---|---|---|---|
| 895-3846 | | | | |
| 895-3846 | | 193.267 | uM | -21.41 |
| | | 19.327 | | 13.40 |
| | 258.708 | 3.865 | | 114.46 |
| | | 0.773 | | 52.12 |
| | | 0.155 | | 38.29 |
| 895-4642 | | | | |
| 895-4642 | | 176.473 | uM | 6.97 |
| | | 17.647 | | 383.99 |
| | 283.331 | 3.529 | | 447.51 |
| | | 0.706 | | 304.86 |
| | | 0.141 | | 100.45 |
| 895-4843 | | | | |
| 895-4843 | | 159.581 | uM | -17.18 |
| | | 15.958 | | 24.54 |
| | 313.312 | 3.192 | | 100.12 |
| | | 0.638 | | 60.37 |
| | | 0.128 | | 27.85 |
| 895-5185 | | | | |
| 895-5185 | | 162.433 | uM | -6.47 |
| | | 16.243 | | 213.42 |
| | 307.821 | 3.249 | | 107.83 |
| | | 0.650 | | 46.75 |
| | | 0.130 | | 18.27 |

FIG. 4R

| Structure | | | | |
|---|---|---|---|---|
| 895-5960 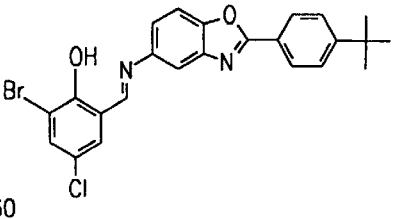 | | | | |
| 895-5960 | | 103.348 | uM | −10.03 |
| | | 10.335 | | 156.04 |
| | 483.796 | 2.067 | | 62.07 |
| | | 0.413 | | 34.47 |
| | | 0.083 | | 7.24 |
| 895-6353 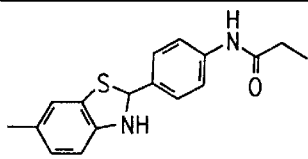 | | | | |
| 895-6353 | | 167.555 | uM | −10.45 |
| | | 16.755 | | 21.59 |
| | 298.408 | 3.351 | | 101.77 |
| | | 0.670 | | 54.91 |
| | | 0.134 | | 24.15 |
| 895-6643 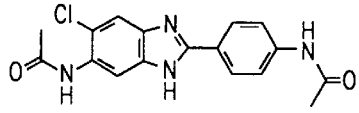 | | | | |
| 895-6643 | | 145.862 | uM | 100.09 |
| | | 14.586 | | 74.25 |
| | 342.786 | 2.917 | | 16.86 |
| | | 0.583 | | −0.89 |
| | | 0.117 | | −7.94 |
| 895-7828 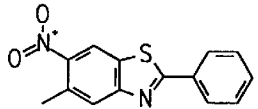 | | | | |
| 895-7828 | | 184.973 | uM | −32.44 |
| | | 18.497 | | −29.24 |
| | 270.31 | 3.699 | | 85.15 |
| | | 0.740 | | 125.64 |
| | | 0.148 | | −30.80 |
FIG. 4S

| | | | |
|---|---|---|---|
| 895-7985 | | | |
| 895-7985 | | 223.935 uM | 122.070 |
| | | 22.394 | 3.900 |
| | 223.279 | 4.479 | -7.790 |
| | | 0.896 | 5.520 |
| | | 0.179 | -2.270 |
| 895-7997 | | | |
| 895-7997 | | 176.461 uM | |
| | | 17.646 | |
| | 283.349 | 3.529 | |
| | | 0.706 | |
| | | 0.141 | |
| 895-8053 | | | |
| 895-8053 | | 134.398 uM | |
| | | 13.440 | |
| | 372.03 | 2.666 | |
| | | 0.538 | |
| | | 0.108 | |
| 895-8137 | | | |
| 895-8137 | | 169.326 uM | |

FIG. 4T

| | | | |
|---|---|---|---|
| | | 16.933 | |
| | 295.288 | 3.387 | |
| | | 0.677 | |
| | | 0.135 | |
| 895-8185 [structure] | | | |
| 895-8185 | | 219.057 | uM |
| | | 21.906 | |
| | 228.251 | 4.361 | |
| | | 0.876 | |
| | | 0.175 | |
| 895-8286 [structure] | | | |
| 895-8286 | | 142.765 | uM |
| | | 14.277 | |
| | 350.225 | 2.855 | |
| | | 0.571 | |
| | | 0.114 | |
| 895-8383 [structure] | | | |
| 895-8383 | | 191.774 | uM |
| | | 19.177 | |
| | 260.724 | 3.835 | |
| | | 0.767 | |
| | | 0.153 | |

| |
|---|
| |
| |
| |
| |
| |
| 142.210 |
| 40.390 |
| 17.850 |
| −10.890 |
| 6.580 |
| |
| −44.020 |
| 76.480 |
| 135.940 |
| 77.030 |
| 37.630 |

FIG. 4U

| | | | |
|---|---|---|---|
| 895-8862 | | | |
| 895-8862 | 165.876 | uM | 54.72 |
| | 16.588 | | 159.21 |
| 301.43 | 3.318 | | 113.97 |
| | 0.664 | | 41.96 |
| | 0.133 | | 38.28 |
| 895-9683 | | | |
| 895-9683 | 113.552 | uM | -20.67 |
| | 11.355 | | 201.56 |
| 440.326 | 2.271 | | 12.55 |
| | 0.454 | | 0.62 |
| | 0.091 | | -0.69 |
| 895-9896 | | | |
| 895-9896 | 178.349 | uM | -29.16 |
| | 17.835 | | 0.62 |
| 280.349 | 3.567 | | 182.84 |
| | 0.713 | | 118.55 |
| | 0.143 | | 42.75 |

FIG. 4V

| Structure | | | | |
|---|---|---|---|---|
| 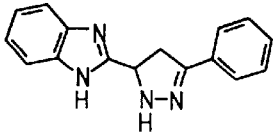 | | | | |
| 896-0122 | | | | |
| 896-0122 | | 190.610 | uM | -14.15 |
| | | 19.061 | | 151.42 |
| | 262.316 | 3.812 | | 56.90 |
| | | 0.762 | | 19.20 |
| | | 0.152 | | 11.42 |
| 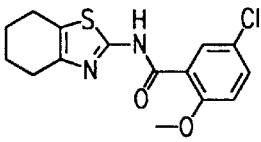 | | | | |
| 896-0246 | | | | |
| 896-0246 | | 154.888 | uM | -17.57 |
| | | 15.489 | | 34.35 |
| | 322.814 | 3.096 | | 102.03 |
| | | 0.620 | | 46.52 |
| | | 0.124 | | 20.52 |
| 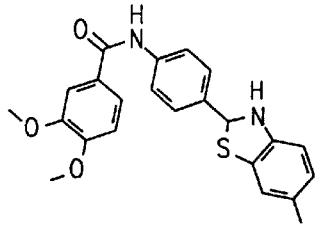 | | | | |
| 896-0255 | | | | |
| 896-0255 | | 123.000 | uM | -17.14 |
| | | 12.300 | | 67.75 |
| | 406.504 | 2.480 | | 168.78 |
| | | 0.492 | | 61.27 |
| | | 0.098 | | 49.97 |
| 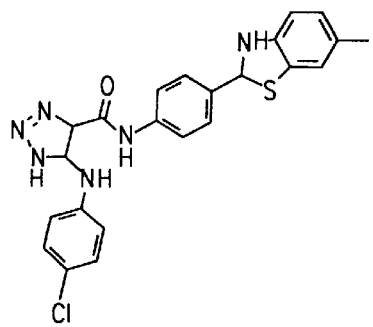 | | | | |
| 896-0345 | | | | |
| 896-0345 | | 107.532 | uM | -18.86 |
| | | 10.753 | | 77.80 |
FIG. 4W

| | | | |
|---|---:|---|---:|
| | 464.979 | 2.151 | | 188.94 |
| | | 0.430 | | 106.12 |
| | | 0.086 | | 37.18 |
| 896-0390 (structure) | | | | |
| 896-0390 | | 128.718 | uM | -16.90 |
| | | 12.872 | | 87.23 |
| | 388.445 | 2.574 | | 210.25 |
| | | 0.515 | | 73.35 |
| | | 0.103 | | 28.25 |
| 896-0535 (structure) | | | | |
| 896-0535 | | 132.810 | uM | -10.41 |
| | | 13.281 | | 73.84 |
| | 376.478 | 2.656 | | 199.80 |
| | | 0.531 | | 102.12 |
| | | 0.106 | | 35.72 |
| 896-0554 (structure) | | | | |
| 896-0554 | | 121.499 | uM | -16.32 |
| | | 12.150 | | 105.48 |
| | 411.527 | 2.430 | | 115.43 |
| | | 0.486 | | 53.88 |
| | | 0.097 | | 27.03 |

FIG. 4X

| | | | | |
|---|---|---|---|---|
| 896-0686 | | | | |
| 896-0686 | | 191.774 | uM | -19.80 |
| | | 19.177 | | 176.04 |
| | 260.724 | 3.835 | | 115.02 |
| | | 0.767 | | 97.67 |
| | | 0.153 | | 25.27 |
| 896-0692 | | | | |
| 896-0692 | | 131.269 | uM | 22.78 |
| | | 13.127 | | 149.23 |
| | 380.897 | 2.625 | | 78.33 |
| | | 0.525 | | 51.06 |
| | | 0.105 | | 46.12 |
| 896-0719 | | | | |
| 896-0719 | | 91.950 | uM | -6.49 |
| | | 9.195 | | 187.43 |
| | 543.774 | 1.839 | | 127.43 |
| | | 0.366 | | 50.04 |
| | | 0.074 | | 36.16 |
| 896-0773 | | | | |
| 896-0773 | | 147.228 | uM | -13.94 |
| | | 14.723 | | 175.33 |
| | 339.609 | 2.945 | | 221.91 |
| | | 0.589 | | 52.48 |
| | | 0.118 | | 32.99 |

FIG. 4Y

| | | | | |
|---|---|---|---|---|
| 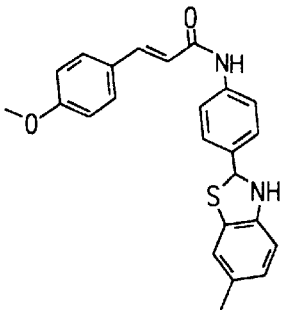 | | | | |
| 896-0819 | | | | |
| 896-0819 | | 124.219 | uM | -16.20 |
| | | 12.422 | | 70.03 |
| | 402.516 | 2.484 | | 165.79 |
| | | 0.497 | | 82.61 |
| | | 0.099 | | 49.06 |
| 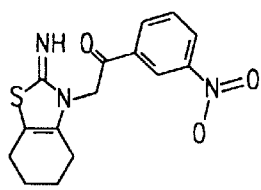 | | | | |
| 896-0853 | | | | |
| 896-0853 | | 157.546 | uM | -27.06 |
| | | 15.755 | | 75.38 |
| | 317.367 | 3.151 | | 208.69 |
| | | 0.630 | | 33.08 |
| | | 0.126 | | 32.63 |
| 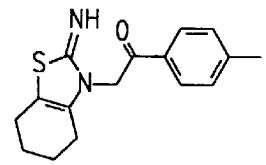 | | | | |
| 896-0921 | | | | |
| 896-0921 | | 174.583 | uM | -19.59 |
| | | 17.458 | | 44.07 |
| | 266.397 | 3.492 | | 103.23 |
| | | 0.698 | | 54.02 |
| | | 0.140 | | 23.86 |
FIG. 4Z

| | | |
|---|---|---|
| 896-0936 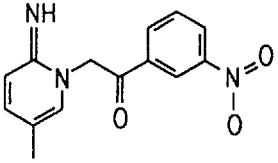 | | |
| 896-0936 | 184.314 uM | -16.20 |
| | 18.431 | 153.61 |
| 271.276 | 3.686 | 184.53 |
| | 0.737 | 79.16 |
| | 0.147 | 32.61 |
| 896-0959 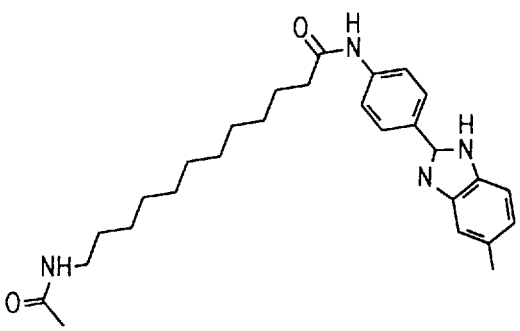 | | |
| 896-0959 | 103.796 uM | -1.73 |
| | 10.380 | 102.48 |
| 461.703 | 2.076 | 61.61 |
| | 0.415 | 63.56 |
| | 0.083 | 48.27 |
| 896-1201 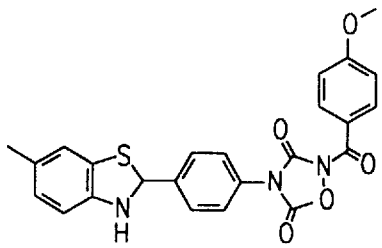 | | |
| 896-1201 | 106.343 uM | -45.70 |
| | 10.834 | 92.57 |
| 461.496 | 2.167 | 191.83 |
| | 0.433 | 47.22 |
| | 0.087 | 58.25 |
FIG. 4AA

| | | | |
|---|---:|---|---:|
| 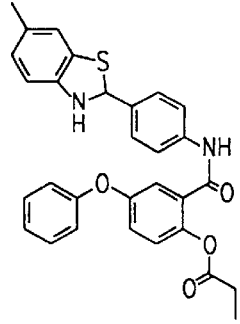 | | | |
| 896-1301 | | | |
| 896-1301 | 97.922 | uM | -24.32 |
| | 9.792 | | 102.49 |
| 510.612 | 1.958 | | 139.28 |
| | 0.392 | | 97.89 |
| | 0.078 | | 23.45 |
| 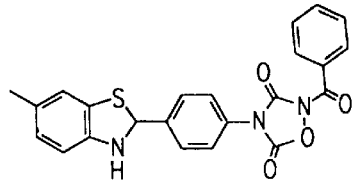 | | | |
| 896-1349 | | | |
| 896-1349 | 115.883 | uM | -39.92 |
| | 11.588 | | 55.08 |
| 431.47 | 2.318 | | 122.68 |
| | 0.464 | | 67.25 |
| | 0.093 | | 3.39 |
| 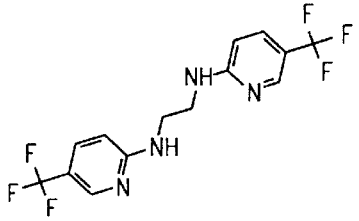 | | | |
| 896-1362 | | | |
| 896-1362 | 142.749 | uM | 1,073.91 |
| | 14.275 | | 1,082.17 |
| 360.266 | 2.855 | | 884.71 |
| | 0.571 | | -9.82 |
| | 0.114 | | -20.37 |
FIG. 4BB

COMPOSITIONS AND METHODS FOR TREATING BONE DEFICIT CONDITIONS

This application is a continuation of U.S. application Ser. No. 08/735.874 filed Oct. 23, 1996, now abandoned.

TECHNICAL FIELD

The invention relates to compositions and methods for use in limiting undesired one loss in a vertebrate at risk of such bone loss, in treating conditions that are characterized by undesired bone loss or by the need for bone growth, in treating fractures, and in treating cartilage disorders. More specifically, the invention concerns the use of specific classes of compounds identified or characterized by a high throughput screening assay.

BACKGROUND ART

Bone is not a static tissue. It is subject to constant breakdown and resynthesis in a complex process mediated by osteoblasts, which produce new bone, and osteoclasts, which destroy bone. The activities of these cells are regulated by a large number of cytokines and growth factors, many of which have now been identified and cloned. Mundy has described the current knowledge related to these factors (Mundy, G. R. Clin Orthop 324:24–28, 1996; Mundy, G. R. J Bone Miner Res 8:S505–10, 1993).

Although there is a great deal of information available on the factors which influence the breakdown and resorption of bone, information on growth factors which stimulate the formation of new bone is more limited. Investigators have searched for sources of such activities, and have found that bone tissue itself is a storehouse for factors which have the capacity for stimulating bone cells. Thus, extracts of bovine bone tissue obtained from slaughterhouses contain not only structural proteins which are responsible for maintaining the structural integrity of bone, but also biologically active bone growth factors which can stimulate bone cells to proliferate. Among these latter factors are transforming growth factor 13, the heparin-binding growth factors (acidic and basic fibroblast growth factor), the insulin-like growth factors (insulin-like growth factor I and insulin-like growth factor II), and a recently described family of proteins called bone morphogenetic proteins (BMPs). All of these growth factors have effects on other types of cells, as well as on bone cells.

The BMPs are novel factors in the extended transforming growth factor β superfamily. They were first identified by Wozney J. et al. Science (1988) 242:1528–34, using gene cloning techniques, following earlier descriptions characterizing the biological activity in extracts of demineralized bone (Urist M. Science (1965) 150:893–99). Recombinant BMP2 and BMP4 can induce new bone formation when they are injected locally into the subcutaneous tissues of rats (Wozney J. Molec Reprod Dev (1992) 32:160–67). These factors are expressed by normal osteoblasts as they differentiate, and have been shown to stimulate osteoblast differentiation and bone nodule formation in vitro as well as bone formation in vivo (Harris S. et al. J Bone Miner Res (1994) 9:855–63). This latter property suggests potential usefulness as therapeutic agents in diseases which result in bone loss.

The cells which are responsible for forming bone are osteoblasts. As osteoblasts differentiate from precursors to mature bone-forming cells, they express and secrete a number of enzymes and structural proteins of the bone matrix, including Type-1 collagen, osteocalcin, osteopontin and alkaline phosphatase (Stein G. et al. Curr Opin Cell Biol (1990) 2:1018–27; Harris S. et al. (1994), supra). They also synthesize a number of growth regulatory peptides which are stored in the bone matrix, and are presumably responsible for normal bone formation. These growth regulatory peptides include the BMPs (Harris S. et al. (1994), supra). In studies of primary cultures of fetal rat calvarial osteoblasts, BMPs 1, 2, 3, 4, and 6 are expressed by cultured cells prior to the formation of mineralized bone nodules (Harris S. et al. (1994), supra). Like alkaline phosphatase, osteocalcin and osteopontin, the BMPs are expressed by cultured osteoblasts as they proliferate and differentiate.

Although the BMPs are potent stimulators of bone formation in vitro and in vivo, there are disadvantages to their use as therapeutic agents to enhance bone healing. Receptors for the bone morphogenetic proteins have been identified in many tissues, and the BMPs themselves are expressed in a large variety of tissues in specific temporal and spatial patterns. This suggests that BMPs may have effects on many tissues other than bone, potentially limiting their usefulness as therapeutic agents when administered systemically. Moreover, since they are peptides, they would have to be administered by injection. These disadvantages impose severe limitations to the development of BMPs as therapeutic agents.

There is a plethora of conditions which are characterized by the need to enhance bone formation. Perhaps the most obvious is the case of bone fractures, where it would be desirable to stimulate bone growth and to hasten and complete bone repair. Agents that enhance bone formation would also be useful in facial reconstruction procedures. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, and glucocorticoid-related osteoporosis. In addition, or alternatively, the compounds of the present invention may modulate metabolism, proliferation and/or differentiation of normal or aberrant cells or tissues.

There are currently no satisfactory pharmaceutical approaches to managing any of these conditions. Bone fractures are still treated exclusively using casts, braces, anchoring devices and other strictly mechanical means. Further bone deterioration associated with post-menopausal osteoporosis has been decreased or prevented with estrogens or bisphosphonates.

U.S. Pat. No. 5,280,040 discloses a class of compounds which are 3,4-diaryl chromans. These compounds can be considered derivatives of 2,3,4 triphenyl butanol, where the hydroxy at the 1-position forms an ether with the ortho position of the phenyl group substituted at the 4-position of the butanol. The parent 3,4-diaryl chromans do not contain nitrogen atoms in the aromatic moieties or their linkers. A preferred compound, centchroman, contains a nitrogen substituent only in one of the substituents on a phenyl moiety. These compounds are disclosed in the '040 patent as useful in the treatment of osteoporosis.

The present invention discloses compounds useful for limiting or treating bone deficit conditions, and for other uses that should be apparent to those skilled in the art from the teachings herein.

DISCLOSURE OF THE INVENTION

The invention provides compounds that can be administered as ordinary pharmaceuticals and have the metabolic effect of enhancing bone growth. The compounds of the invention can be identified using an assay for their ability to activate control elements associated with these factors. Thus, the invention is directed to methods and compositions for stimulating the growth of skeletal (bone) tissue, which methods and compositions use, as active ingredients, compounds wherein two aromatic systems are coupled so as to be spaced apart from each other by about 1.5 to about 15 Angstroms. The thus-linked systems (including the linker coupling them) generally include at least one nitrogen atom.

Therefore, the compounds useful in the invention can be described as having the formula $Ar^1$-linker-$Ar^2$, wherein each of $Ar^1$ and $Ar^2$ is independently an aromatic system and the linker portion of the formula spaces $Ar^1$ and $Ar^2$ apart by a distance of approximately 1.5–15 Angstroms. $Ar^1$, $Ar^2$ and the linker may optionally be substituted with non interfering substituents. In the useful compounds, there is generally at least one nitrogen atom in either $Ar^1$, $Ar^2$ and/or the linker, independent of any substituents thereon. Preferably, the compounds of the invention contain at least one additional heteroatom selected from the group consisting of N, S and O, independent of any substituent.

Thus, in one aspect, the invention is directed to A method to treat a condition in a vertebrate animal characterized by a deficiency in, or need for, bone growth replacement and/or an undesirable level of bone resorption, which method comprises administering to a vertebrate subject in need of such treatment an effective amount of a compound of the formula

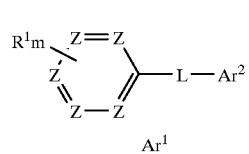

(1)

wherein each $R^1$ is independently a non-interfering substituent;

m is an integer of 0–5;

each Z is independently N or CR, where R is H or alkyl (1–6 C), with the proviso that at least one Z must be a heteroatom and at least one Z must be CR;

L is a linker; and $Ar^2$ is a substituted or unsubstituted phenyl, a substituted or unsubstituted naphthyl, a substituted or unsubstituted aromatic system containing a 6-membered heterocycle, or a substituted or unsubstituted aromatic system containing a 5-membered heterocycle.

In other aspects, the invention relates to pharmaceutical compositions for use in the method.

BRIEF DESCRIPTION OF THE DRAWINGS

FIG. 1 gives a schematic representation of the compounds used as active ingredients in the methods of the invention.

FIGS. 3 and 4 show illustrative compounds of the invention and the results obtained with them in an in vitro test.

MODES OF CARRYING OUT THE INVENTION

Figure 2:
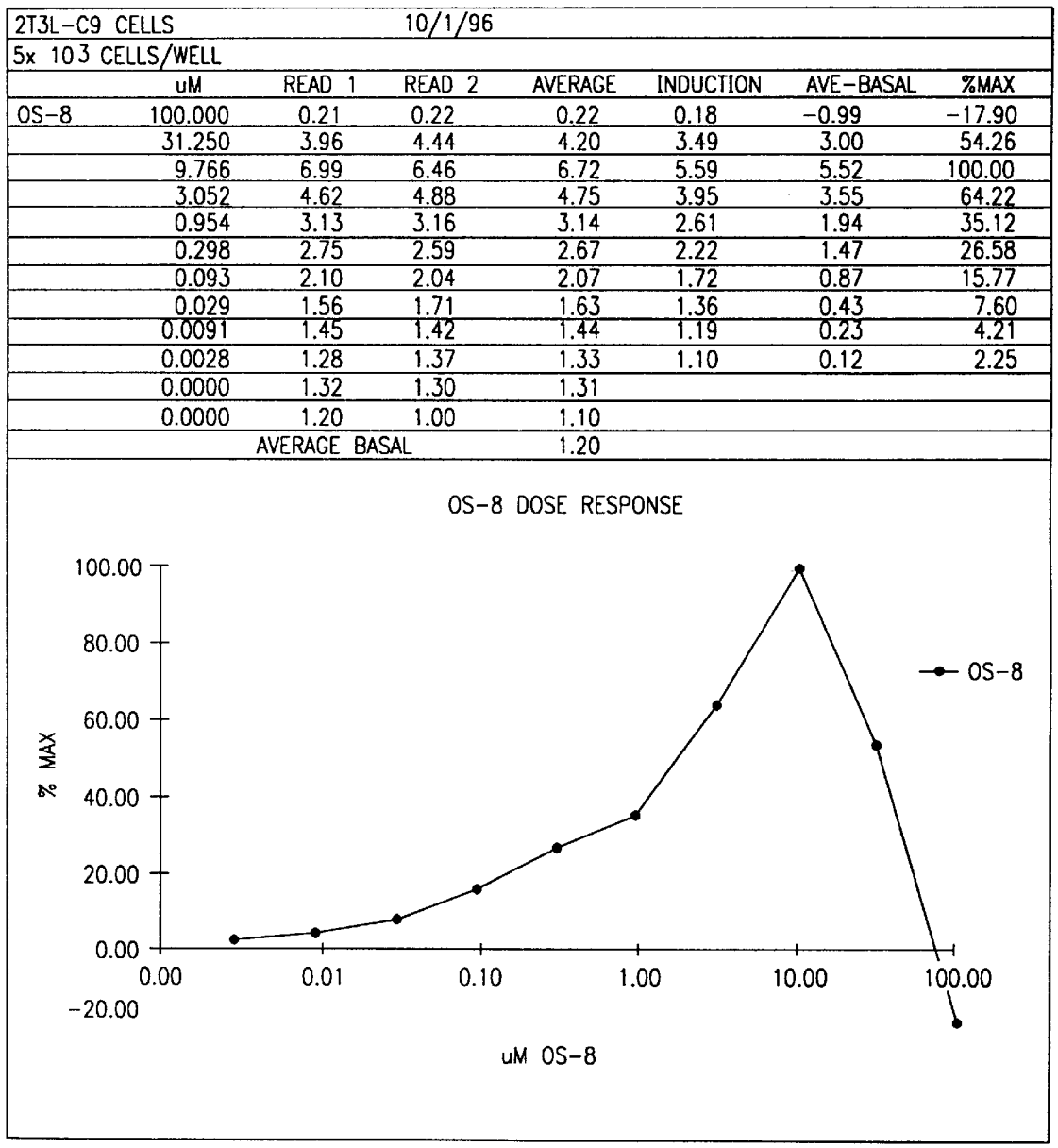
FIG. 2 shows the dose response curve for a positive control compound, designated 59-0008.

A rapid throughput screening test for compounds capable of stimulating expression of a reporter gene linked to a BMP promoter (a surrogate for the production of bone morphogenetic factors that are endogenously produced) is described in U.S. application Ser. No. 08/458,434, filed Jun. 2, 1995, the contents of which are incorporated herein by reference. This assay is also described as a portion of a study of immortalized murine osteoblasts (derived from a mouse expressing a transgene composed of a BMP2 promoter driving expression of T-antigen) in Ghosh-Choudhery, N. et al. *Endocrinology* (1996) 137:331–39. In this study, the immortalized cells were stably transfected with a plasmid containing a luciferase reporter gene driven by a mouse BMP2 promoter (−2736/114 bp), and responded in a dose-dependent manner to recombinant human BMP2.

Briefly, the assay utilizes cells transformed permanently or transiently with constructs in which the promoter of a bone morphogenetic protein, specifically BMP2 or BMP4, is coupled to a reporter gene, typically luciferase. These transformed cells are then evaluated for the production of the reporter gene product; compounds that activate the BMP promoter will drive production of the reporter protein, which can be readily assayed. Over 40,000 compounds have been subjected to this rapid screening technique, and only a very small percentage are able to elicit a level of production of luciferase 5-fold greater than that produced by vehicle. Compounds that activate the BMP promoter share certain structural characteristics not present in inactive compounds. The active compounds ("BMP promoter-active compounds" or "active compounds") are useful in promoting bone or cartilage growth, and thus in the treatment of vertebrates in need of bone or cartilage growth.

BMP promoter-active compounds can be examined in a variety of other assays that test specificity and toxicity. For instance, non-BMP promoters or response elements can be linked to a reporter gene and inserted into an appropriate host cell. Cytotoxicity can be determined by visual or microscopic examination of BMP promoter- and/or non-BMP promoter-reporter gene-containing cells, for instance. Alternatively, nucleic acid and/or protein synthesis by the cells can be monitored. For in vivo assays, tissues may be removed and examined visually or microscopically, and optionally examined in conjunction with dyes or stains that facilitate histologic examination. In assessing in vivo assay results. it may also be useful to examine biodistribution of the test compound, using conventional medicinal chemistry/animal model techniques.

As used herein, "limit" or "limiting" and "treat" or "treatment" are interchangeable terms. The terms include a postponement of development of bone deficit symptoms and/or a reduction in the severity of such symptoms that will or are expected to develop. The terms further include ameliorating existing bone or cartilage deficit symptoms, preventing additional symptoms, ameliorating or preventing the underlying metabolic causes of symptoms, preventing or reversing bone resorption and/or encouraging bone growth. Thus, the terms denote that a beneficial result has been conferred on a vertebrate subject with a cartilage, bone or skeletal deficit, or with the potential to develop such deficit.

By "bone deficit" is meant an imbalance in the ratio of bone formation to bone resorption, such that, if unmodified, the subject will exhibit less bone than desirable, or the subject's bones will be less intact and coherent than desired. Bone deficit may also result from fracture, from surgical intervention or from dental or periodontal disease. By "cartilage defect" is meant damaged cartilage, less cartilage than desired, or cartilage that is less intact and coherent than desired.

Representative uses of the compounds of the present invention include: repair of bone defects and deficiencies, such as those occuring in closed, open and non-union fractures; prophylactic use in closed and open fracture reduction; promotion of bone healing in plastic surgery; stimulation of bone ingrowth into non-cemented prosthetic joints and dental implants; elevation of peak bone mass in pre-menopausal women; treatment of growth deficiencies; treatment of peridontal disease and defects, and other tooth repair processes; increase in bone formation during distraction osteogenesis; and treatment of other skeletal disorders, such as age-related osteoporosis, post-menopausal osteoporosis, glucocorticoid-induced osteoporosis or disuse osteoporosis and arthritis. The compounds of the present invention can also be useful in repair of congenital, trauma-induced or surgical resection of bone (for instance, for cancer treatment), and in cosmetic surgery. Further, the compounds of the present invention can be used for limiting or treating cartilage defects or disorders, and may be useful in wound healing or tissue repair.

Bone or cartilage deficit or defect can be treated in vertebrate subjects by administering compounds of the invention which have been identified through suitable screening assays and which exhibit certain structural characteristics. The compositions of the invention may be administered systemically or locally. For systemic use, the compounds herein are formulated for parenteral (e.g., intravenous, subcutaneous, intramuscular, intraperitoneal, intranasal or transdermal) or enteral (e.g., oral or rectal) delivery according to conventional methods. Intravenous administration will be by a series of injections or by continuous infusion over an extended period. Administration by injection or other routes of discretely spaced administration will generally be performed at intervals ranging from weekly to once to three times daily. Alternatively, the compounds disclosed herein may be administered in a cyclical manner (administration of disclosed compound; followed by no administration; followed by administration of disclosed compound, and the like). Treatment will continue until the desired outcome is achieved. In general, pharmaceutical formulations will include a compound of the present invention in combination with a pharmaceutically acceptable vehicle, such as saline, buffered saline, 5% dextrose in water, borate-buffered saline containing trace metals or the like. Formulations may further include one or more excipients, preservatives, solubilizers, buffering agents, albumin to prevent protein loss on vial surfaces, lubricants, fillers, stabilizers, etc. Methods of formulation are well known in the art and are disclosed, for example, in *Remington's Pharmaceutical Sciences*, Gennaro, ed., Mack Publishing Co., Easton Pa., 1990, which is incorporated herein by reference. Pharmaceutical compositions for use within the present invention can be in the form of sterile, non-pyrogenic liquid solutions or suspensions, coated capsules, suppositories, lyophilized powders, transdermal patches or other forms known in the art. Local administration may be by injection at the site of injury or defect, or by insertion or attachment of a solid carrier at the site, or by direct, topical application of a viscous liquid. For local administration, the delivery vehicle preferably provides a matrix for the growing bone or cartilage, and more preferably is a vehicle that can be absorbed by the subject without adverse effects.

Delivery of compounds herein to wound sites may be enhanced by the use of controlled-release compositions, such as those described in pending U.S. patent application Ser. No. 07/871,246 (corresponding to WIPO publication WO 93/20859, which is incorporated herein by reference in its entirety). Films of this type are particularly useful as coatings for prosthetic devices and surgical implants. The films may, for example, be wrapped around the outer surfaces of surgical screws, rods, pins, plates and the like. Implantable devices of this type are routinely used in orthopedic surgery. The films can also be used to coat bone filling materials, such as hydroxyapatite blocks, demineralized bone matrix plugs, collagen matrices and the like. In general, a film or device as described herein is applied to the bone at the fracture site. Application is generally by implantation into the bone or attachment to the surface using standard surgical procedures.

In addition to the copolymers and carriers noted above, the biodegradable films and matrices may include other active or inert components. Of particular interest are those agents that promote tissue growth or infiltration, such as growth factors. Exemplary growth factors for this purpose include epidermal growth factor (EGF), fibroblast growth factor (FGF), platelet-derived growth factor (PDGF), transforming growth factors (TGFs), parathyroid hormone (PTH), leukemia inhibitory factor (LIF), and insulin-like growth factors (IGFs). Agents that promote bone growth, such as bone morphogenetic proteins (U.S. Pat. No. 4,761,471; PCT Publication WO 90/11366), osteogenin (Sampath et al. *Proc. Natl. Acad. Sci. USA* (1987) 84:7109–13) and NaF (Tencer et al. *J Biomed. Mat. Res.* (1989) 23: 571–89) are also preferred. Biodegradable films or matrices include calcium sulfate, tricalcium phosphate, hydroxyapatite, polylactic acid, polyanhydrides, bone or dermal collagen, pure proteins, extracellular matrix components and combinations thereof Such biodegradable materials may be used in combination with non-biodegradable materials, to provide desired mechanical, cosmetic or tissue or matrix interface properties.

Alternative methods for delivery of compounds of the present invention include use of ALZET osmotic minipumps (Alza Corp., Palo Alto, Calif.); sustained release matrix materials such as those disclosed in Wang et al (PCT Publication WO 90/11366); electrically charged dextran beads, as disclosed in Bao et al. (PCT Publication WO 92/03125); collagen-based delivery systems, for example, as disclosed in Ksander et al. *Ann. Surg.* (1990) 211(3):288–94; methylcellulose gel systems, as disclosed in Beck et al. *J. Bone Min. Res.* (1991) 6(11): 1257–65; and alginate-based systems, as disclosed in Edelman et al. *Biomaterials* (1991) 12:619–26. Other methods well known in the art for sustained local delivery in bone include porous coated metal protheses that can be impregnated and solid plastic rods with therapeutic compositions incorporated within them.

The compounds of the present invention may also be used in conjunction with agents that inhibit bone resorption. Antiresorptive agents, such as estrogen, bisphosphonates and calcitonin, are preferred for this purpose. More specifically, the compounds disclosed herein may be administered for a period of time (for instance, months to years) sufficient to obtain correction of a bone deficit condition. Once the bone deficit condition has been corrected, the vertebrate can be administered an anti-resorptive compound to maintain the corrected bone condition. Alternatively, the compounds disclosed herein may be adminstered with an anti-resorptive compound in a cyclical manner (administration of disclosed compound, followed by antiresorptive, followed by disclosed compound, and the like).

In additional formulations, conventional preparations such as those described below may be used.

Aqueous suspensions may contain the active ingredient in admixture with pharmacologically acceptable excipients, comprising suspending agents, such as methyl cellulose, and wetting agents, such as lecithin, lysolethicin or long-chain fatty alcohols. The said aqueous suspensions may also contain preservatives, coloring agents, flavoring agents and sweetening agents in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

If desired, the osteogenic agents can be incorporated into liposomes by any of the reported methods of preparing liposomes for use in treating various pathogenic conditions. The present compositions may utilize the compounds noted above incorporated in liposomes in order to direct these compounds to macrophages, monocytes, other cells and tissues and organs which take up the liposomal composition. The liposome-incorporated compounds of the invention can be utilized by parenteral administration, to allow for the efficacious use of lower doses of the compounds. Ligands may also be incorporated to further focus the specificity of the liposomes.

Suitable conventional methods of liposome preparation include, but are not limited to, those disclosed by Bangham, A. D. et al. *J Mol Biol* (1965) 23:238–252, Olson, F. et al. *Biochim Biophys Acta* (1979) 557:9–23, Szoka, F. et al. *Proc Natl Acad Sci USA* (1978) 75:4194–4198, Kim, S. et al. *Biochim Biophys Acta* (1983) 728:339:348, and Mayer, et al. *Biochim Biophys Acta* (1986) 858:161–168.

The liposomes may be made from the present compounds in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol. Synthetic phospholipids that may also be used, include, but are not limited to: dimyristoylphosphatidylcholine, dioleoylphosphatidylcholine, dipalmitoylphosphatidylcholine and distearoylphosphatidycholine, and the corresponding synthetic phosphatidylethanolamines and phosphatidylglycerols. Cholesterol or other sterols, cholesterol hemisuccinate, glycolipids, cerebrosides, fatty acids, gangliosides, sphingolipids, 1,2-bis(oleoyloxy)-3-(trimethyl ammonio) propane (DOTAP), N-[1-(2,3-dioleoyl) propyl-N,N,N-trimethylammonium chloride (DOTMA), and other cationic lipids may be incorporated into the liposomes, as is known to those skilled in the art. The relative amounts of phospholipid and additives used in the liposomes may be varied if desired. The preferred ranges are from about 60 to 90 mole percent of the phospholipid; cholesterol, cholesterol hemisuccinate, fatty acids or cationic lipids may be used in amounts ranging from 0 to 50 mole percent. The amounts of the present compounds incorporated into the lipid layer of liposomes can be varied with the concentration of their lipids ranging from about 0.01 to about 50 mole percent.

Using conventional methods, approximately 20 to 30% of the compound present in solution can be entrapped in liposomes; thus, approximately 70 to 80% of the active compound is wasted. In contrast, where the compound is incorporated into liposomes, virtually all of the compound is incorporated into the liposome, and essentially none of the active compound is wasted.

The liposomes with the above formulations may be made still more specific for their intended targets with the incorporation of monoclonal antibodies or other ligands specific for a target. For example, monoclonal antibodies to the BMP receptor may be incorporated into the liposome by linkage to phosphatidylethanolamine (PE) incorporated into the liposome by the method of Leserman, L. et al. *Nature* (1980) 288:602–604.

Veterinary uses of the disclosed compounds are also contemplated. Such uses would include limitation or treatment of bone or cartilage deficits or defects in domestic animals, livestock and thoroughbred horses. The compounds described herein can also modify a target tissue or organ environment, so as to attract bone-forming cells to an environment in need of such cells.

The compounds of the present invention may also be used to stimulate growth of bone-forming cells or their precursors, or to induce differentiation of bone-forming cell precursors, either in vitro or ex vivo. As used herein, the term "precursor cell" refers to a cell that is committed to a differentiation pathway, but that generally does not express markers or function as a mature, fully differentiated cell. As used herein, the term "mesenchymal cells" or "mesenchymal stem cells" refers to pluripotent progenitor cells that are capable of dividing many times, and whose progeny will give rise to skeletal tissues, including cartilage, bone, tendon, ligament, marrow stroma and connective tissue (see A. Caplan *J. Orthop. Res.* (1991) 9:641–50). As used herein, the term "osteogenic cells" includes osteoblasts and osteoblast precursor cells. More particularly, the disclosed compounds are useful for stimulating a cell population containing marrow mesenchymal cells, thereby increasing the number of osteogenic cells in that cell population. In a preferred method, hematopoietic cells are removed from the cell population, either before or after stimulation with the disclosed compounds. Through practice of such methods, osteogenic cells may be expanded. The expanded osteogenic cells can be infused (or reinfused) into a vertebrate subject in need thereof For instance, a subject's own mesenchymal stem cells can be exposed to compounds of the present invention ex vivo, and the resultant osteogenic cells could be infused or directed to a desired site within the subject, where further proliferation and/or differentiation of the osteogenic cells can occur without immunorejection. Alternatively, the cell population exposed to the disclosed compounds may be immortalized human fetal osteoblastic or osteogenic cells. If such cells are infused or implanted in a vertebrate subject, it may be advantageous to "immunoprotect" these non-self cells, or to immunosuppress (preferably locally) the recipient to enhance transplantation and bone or cartilage repair.

Within the present invention, an "effective amount" of a composition is that amount which produces a statistically significant effect. For example, an "effective amount" for therapeutic uses is the amount of the composition comprising an active compound herein required to provide a clinically significant increase in healing rates in fracture repair; reversal of bone loss in osteoporosis; reversal of cartilage defects or disorders; prevention or delay of onset of osteoporosis; stimulation and/or augmentation of bone formation in fracture non-unions and distraction osteogenesis; increase and/or acceleration of bone growth into prosthetic devices; and repair of dental defects. Such effective amounts will be determined using routine optimization techniques and are dependent on the particular condition to be treated, the condition of the patient, the route of administration, the formulation, and the judgment of the practitioner and other factors evident to those skilled in the art. The dosage required for the compounds of the invention (for example, in osteoporosis where an increase in bone formation is desired) is manifested as a statistically significant difference in bone mass between treatment and control groups. This difference in bone mass may be seen, for example, as a 5–20% or more increase in bone mass in the treatment group. Other measurements of clinically significant increases in healing may include, for example, tests for breaking strength and tension, breaking strength and torsion, 4-point bending, increased connectivity in bone biopsies and other biomechanical tests well known to those skilled in the art. General guidance for treatment regimens is obtained from experiments carried out in animal models of the disease of interest.

The dosage of the compounds of the invention will vary according to the extent and severity of the need for treatment, the activity of the administered compound, the general health of the subject, and other considerations well known to the skilled artisan. Generally, they can be administered to a typical human on a daily basis on an oral dose of about 0.1 mg/kg–1000 mg/kg, and more preferably from about 1 mg/kg to about 200 mg/kg. The parenteral dose will appropriately be 20–100% of the oral dose.

Screening Assays

The osteogenic activity of the compounds used in the methods of the invention can be verified using in vitro screening techniques, such as the assessment of transcription of a reporter gene coupled to a bone morphogenetic protein-associated promoter, as described above, or in alternative assays such as the following:

Technique for Neonatal Mouse Calvaria Assay (In vitro)

This assay is similar to that described by Gowen M. & Mundy G. *J Immunol* (1986) 136:2478–82. Briefly, four days after birth, the front and parietal bones of ICR Swiss white mouse pups are removed by microdissection and split along the sagittal suture. The bones are incubated in BGJb medium (Irvine Scientific, Santa Ana, Calif.) plus 0.02% (or lower concentration) β-methylcyclodextrin, wherein the medium also contains test or control substances, at 37 C in a humidified atmosphere of 5% $CO_2$ and 95% air for 96 hours.

Following this, the bones are removed from the incubation media and fixed in 10% buffered formalin for 24–48 hours, decalcified in 14% EDTA for 1 week, processed through graded alcohols; and embedded in paraffin wax. Three μm sections of the calvaria are prepared. Representative sections are selected for histomorphometric assessment of bone formation and bone resorption. Bone changes are measured on sections cut 200 μm apart. Osteoblasts and osteoclasts are identified by their distinctive morphology.

Other auxiliary assays can be used as controls to determine non-BMP promoter-mediated effects of test compounds. For example, mitogenic activity can be measured using screening assays featuring a serum-response element (SRE) as a promoter and a luciferase reporter gene. More specifically, these screening assays can detect signalling through SRE-mediated pathways, such as the protein kinase C pathway. For instance, an osteoblast activator SRE-luciferase screen and an insulin mimetic SRE-luciferase screen are useful for this purpose. Similarly, test compound stimulation of cAMP response element (CRE)-mediated pathways can also be assayed. For instance, cells transfected with receptors for PTH and calcitonin (two bone-active agents) can be used in CRE-luciferase screens to detect elevated cAMP levels. Thus, the BMP promoter specificity of a test compound can be examined through use of these types of auxiliary assays.

In vivo Assay of Effects of Compounds on Murine Calvarial Bone Growth

Male ICR Swiss white mice, aged 4-6 weeks and weighing 13–26 gm, are employed, using 4–5 mice per group. The calvarial bone growth assay is performed as described in PCT application WO 95/24211. Briefly, the test compound or appropriate control vehicle is injected into the subcutaneous tissue over the right calvaria of normal mice. Typically, the control vehicle is the vehicle in which the compound was solubilized, and is PBS containing 5% DMSO or is PBS containing Tween (2 μl/10 ml). The animals are sacrificed on day 14 and bone growth measured by histomorphometry. Bone samples for quantitation are cleaned from adjacent tissues and fixed in 10% buffered formalin for 24–48 hours, decalcified in 14% EDTA for 1–3 weeks, processed through graded alcohols, and embedded in paraffin wax. Three to five μm sections of the calvaria are prepared, and representative sections are selected for histomorphometric assessment of the effects on bone formation and bone resorption. Sections are measured by using a camera lucida attachment to trace directly the microscopic image onto a digitizing plate. Bone changes are measured on sections cut 200 μm apart, over 4 adjacent 1×1 mm fields on both the injected and noninjected sides of the calvaria. New bone is identified by its characteristic woven structure, and osteoclasts and osteoblasts are identified by their distinctive morphology. Histomorphometry software (OsteoMeasure, Osteometrix, Inc., Atlanta) is used to process digitizer input to determine cell counts and measure areas or perimeters.

Additional In Vivo Assays

Lead compounds can be further tested in intact animals using an in vivo, dosing assay. Prototypical dosing may be accomplished by subcutaneous, intraperitoneal or oral administration, and may be performed by injection, sustained release or other delivery techniques. The time period for administration of test compound may vary (for instance, 28 days as well as 35 days may be appropriate). An exemplary, in vivo subcutaneous dosing assay may be conducted as follows:

In a typical study, 70 three-month-old female Sprague-Dawley rats are weight-matched and divided into seven groups, with ten animals in each group. This includes a baseline control group of animals sacrificed at the initiation of the study; a control group administered vehicle only; a PBS-treated control group; and a positive control group administered a compound (non-protein or protein) known to promote bone growth. Three dosage levels of the compound to be tested are administered to the remaining three groups.

Briefly, test compound, positive control compound, PBS, or vehicle alone is administered subcutaneously once per day for 35 days. All animals are injected with calcein nine days and two days before sacrifice (two injections of calcein administered each designated day). Weekly body weights are determined. At the end of the 35-day cycle, the animals are weighed and bled by orbital or cardiac puncture. Serum calcium, phosphate, osteocalcin, and CBCs are determined. Both leg bones (femur and tibia) and lumbar vertebrae are removed, cleaned of adhering soft tissue, and stored in 70% ethanol for evaluation, as performed by peripheral quantitative computed tomography (pQCT; Ferretti, J. *Bone* (1995) 17:353S–64S), dual energy X-ray absorptiometry (DEXA;

Laval-Jeantet A. et al. *Calcif Tissue Intl* (1995) 56:14–18; J. Casez et al. *Bone and Mineral* (1994) 26:61–68) and/or histomorphometry. The effect of test compounds on bone remodeling can thus be evaluated.

Lead compounds also be tested in acute ovariectomized animals (prevention model) using an in vivo dosing assay. Such assays may also include an estrogen-treated group as a control. An exemplary subcutaneous dosing assay is performed as follows:

In a typical study, 80 three-month-old female Sprague-Dawley rats are weight-matched and divided into eight groups, with ten animals in each group. This includes a baseline control group of animals sacrificed at the initiation of the study; three control groups (sham ovariectomized (sham OVX)+vehicle only; ovariectomized (OVX)+vehicle only; PBS-treated OVX); and a control OVX group that is administered a compound known to promote bone growth. Three dosage levels of the compound to be tested are administered to the remaining three groups of OVX animals.

Since ovariectomy (OVX) induces hyperphagia, all OVX animals are pair-fed with sham OVX animals throughout the 35 day study. Briefly, test compound, positive control compound, PBS, or vehicle alone is administered subcutaneously once per day for 35 days. Alternatively, test compound can be formulated in implantable pellets that are implanted for 35 days, or may be administered orally, such as by gastric gavage. All animals, including sham OVX/vehicle and OVX/vehicle groups, are injected intraperitoneally with calcein nine days and two days before sacrifice (two injections of calcein administered each designated day, to ensure proper labeling of newly formed bone). Weekly body weights are determined. At the end of the 35-day cycle, the animals' blood and tissues are processed as described above.

Lead compounds may also be tested in chronic OVX animals (treatment model). An exemplary protocol for treatment of established bone loss in ovariectomized animals that can be used to assess efficacy of anabolic agents may be performed as follows. Briefly, 80 to 100 six month old female, Sprague-Dawley rats are subjected to sham surgery (sham OVX) or ovariectomy (OVX) at time 0, and 10 rats are sacrificed to serve as baseline controls. Body weights are recorded weekly during the experiment. After approximately 6 weeks of bone depletion (42 days), 10 sham OVX and 10 OVX rats are randomly selected for sacrifice as depletion period controls. Of the remaining animals, 10 sham OVX and 10 OVX rats are used as placebo-treated controls. The remaining OVX animals are treated with 3 to 5 doses of test drug for a period of 5 weeks (35 days). As a postitive control, a group of OVX rats can be treated with an agent such as PTH, a known anabolic agent in this model (Kimmel et al. *Endocrinology* (1993) 132:1577–84). To determine effects on bone formation, the following procedure can be followed. The femurs, tibiae and lumbar vertebrae 1 to 4 are excised and collected. The proximal left and right tibiae are used for pQCT measurements, cancellous bone mineral density (BMD) (gravimetric determination), and histology, while the midshaft of each tibiae is subjected to cortical BMD or histology. The femurs are prepared for pQCT scanning of the midshaft prior to biomechanical testing. With respect to lumbar vertebrae (LV), LV2 are processed for BMD (pQCT may also be performed); LV3 are prepared for undecalcified bone histology; and LV4 are processed for mechanical testing.

Nature of the Compounds Useful in the Invention

All of the compounds of the invention contain two aromatic systems, $Ar^1$ and $Ar^2$, spaced apart by a linker at a distance of 1.5–15 Å, and all generally contain at least one nitrogen atom. A summary of the structural features of the compounds included within the invention is shown in FIG. 1.

As shown, $Ar^1$ and $Ar^2$ may include various preferred embodiments. These are selected from the group consisting of a substituted or unsubstituted aromatic ring system containing a five-membered heterocycle; a substituted or unsubstituted aromatic ring system containing a six-membered heterocycle; a substituted or unsubstituted naphthalene moiety; and a substituted or unsubstituted benzene moiety. There are 16 possible combinations of these embodiments if $Ar^1$ and $Ar^2$, are considered distinguishable. As will be clear, however, the designation of one aromatic system as $Ar^1$ and the other as $Ar^2$ is arbitrary; thus there are only ten possible combinations. However, for simplicity, $Ar^1$ and $Ar^2$ are designated separately with the realization that the choice is arbitrarily made. All linkers described herein if not palindromic, are considered link $Ar^1$ to $Ar^2$ or vice-versa whether or not the complementary orientation is explicitly shown. Thus, if $Ar^1$ and $Ar^2$ are different and a linker is specified as —CONR, it is understood that also included is the linker —NRCO—.

The non-interfering substituents on the aromatic system represented by $Ar^1$ and the non-interfering substituents on the aromatic system represented by $Ar^2$ are represented in the formulae herein by $R^1$ and $R^2$, respectively. Generally, these substituents can be of wide variety. Among substituents that do not interfere with the beneficial effect of the compounds of the invention on bone in treated subjects are included alkyl (1–6C, preferably lower alkyl 1–4C), including straight or branched-chain forms thereof, alkenyl (1–6C, preferably 1–4C), alkynyl (1–6C, preferably 1–4C), all of which can be straight or branched chains and may contain further substituents; halogens, including F, Cl, Br and I; siloxy, OR, SR, $NR_2$, OOCR, COOR, NCOR, NCOOR, and benzoyl, $CF_3$, $OCF_3$, $SCF_3$, $N(CF_3)_2$, CN, SO, $SO_2R$ and $SO_3R$ wherein R is alkyl (1–6C) or is H. Where $R^1$ or $R^2$ substituents are in adjacent positions in the aromatic system, they may form a ring. Further, rings may be included in substituents which contain sufficient carbon and heteroatoms to provide this possibility.

Preferred non-interfering substituents include hydrocarbyl groups of 1–6C, including saturated and unsaturated, linear or branched hydrocarbyl as well as hydrocarbyl groups containing ring systems; halo groups, alkoxy, hydroxy, amino, monoalkyl- and dialkylamino where the alkyl groups are 1–6C, CN, $CF_3$, and COOR.

Although the number of $R^1$ and $R^2$ may typically be 0–4 or 0–5 depending on the available positions in the aromatic system, preferred embodiments include those wherein the number of $R^1$ is 0, 1 or 2 and of $R^2$ is 0, 1 or 2.

The linker group, L, may be a covalent bond or any group having a valence of at least two and covering a linear distance of from about 1.5 to about 15 Angstroms, including those that contain cyclic moieties, that meet this spatial requirement. Useful linkers are divided, by definition herein, into three general categories: (1) flexible non-conjugating linkers, (2) flexible conjugating linkers, and (3) constrained linkers. The preferred choice of linker will depend on the choices for $Ar^1$ and $Ar^2$.

As defined herein, flexible non-conjugating linkers are those that link only one position of $Ar^1$ to one position of $Ar^2$, and provide only a single covalent bond or a single chain between $Ar^1$ and $Ar^2$. The chain may contain branches, but may not contain π-bonds (except in the branches) or cyclic portions in the chain. The linker atoms in the chain itself rotate freely around single covalent bonds, and thus the linker has more than two degrees of freedom. Particularly useful flexible non-conjugating linkers, besides a covalent bond, are those of the formulae: —NR—, —CR$_2$—, —S—, or —O—, wherein R is H or alkyl (1–6C), more preferably H or lower alkyl (1–4C) and more preferably H. Also preferred are those of the formulae: —NRCO—, —CONR—, —CR$_2$S—, —SCR$_2$—, —OCR$_2$—, -CR$_2$O—, —NRNR—, —CR$_2$CR$_2$—, —NRSO$_2$—, —SO$_2$NR—, —CR$_2$CO—, —COCR$_2$—, and —NR—NR—CO—CR$_2$— and its complement —CR$_2$—CO—NR—NR—, including the isosteres thereof Also preferred are those of the formulae: —NR(CR$_2$)$_2$NR—, —O(CR$_2$)$_2$O—, and —S(CR$_2$)$_2$S—, including the isosteres thereof The optimum choice of linker is dependent on the nature of Ar$^1$ and Ar$^2$.

Flexible conjugating linkers are those that link only one position of Ar$^1$ to one position of Ar$^2$, but incorporate at least one double or triple bond or one or more cyclic systems and thus have only two degrees of freedom. A flexible conjugating linker may form a completely conjugated π-bond linking system between Ar$^1$ and Ar$^2$, thus providing for co-planarity of Ar$^1$ and Ar$^2$. Examples of useful flexible conjugating linkers include: —RC=CR—; —N=N—; —C—C—; —RC=N—; —N=CR—; —NR—N=CR—; —NR—NR—CO—CR=CR—; and the like, where R is H or alkyl (1–6C); preferably H or lower alkyl (1–4C); and more preferably H.

Constrained linkers are those that have more than one point of attachment to either or both Ar$^1$ and A$^2$ and, thus, generally allow for only one degree of freedom. Constrained linkers most frequently form fused 5- or 6-membered cyclic moieties with Ar$^1$ and/or Ar$^2$ where either Ar$^1$ or Ar$^2$ has at least one substituent appropriately positioned to form a second covalent bond with the linker, e.g., where Ar$^2$ is a phenyl group with a reactive, ortho-positioned substituent, or is derivatized to the linker directly at the ortho position. (Although the aromatic moieties should properly be refined to as phenylene or naphthylene in such cases, generally the term "phenyl" or "naphthyl" is used herein to include both monovalent and bivalent forms of these moieties.) Examples of particularly useful constrained linkers include

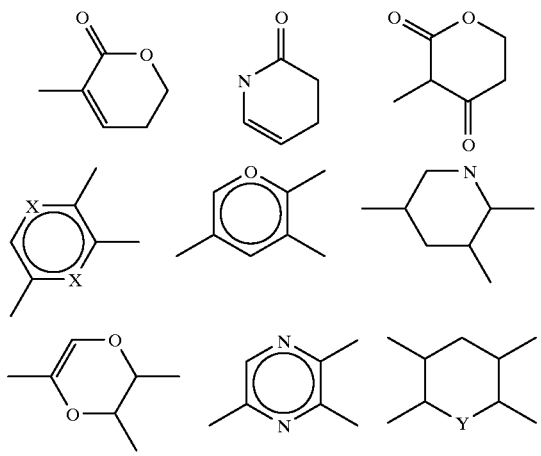

and the like, where X is O, N, S or CR, and Y is CR$_2$ or C=O.

Ar$^1$ is defined herein as of the formula

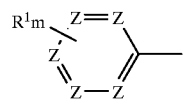

wherein R$^1$ is as set forth above and m is 0–5.

When Ar$^2$ is an aromatic system also containing a six-membered heterocycle, the formula of said system is preferably:

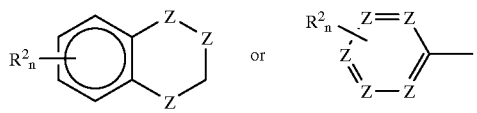

wherein each Z is independently a heteroatom selected from the group consisting of S, O, and N, or is CR or CR$_2$;

the dotted lines represent optional π-bonds;

each R$^2$ is independently a non-interfering substituent; and m is an integer of 0–5;

n is an integer of 0–4;

with the proviso that at least one Z must be a heteroatom.

In this embodiment, Ar$^2$ is preferably of the formula

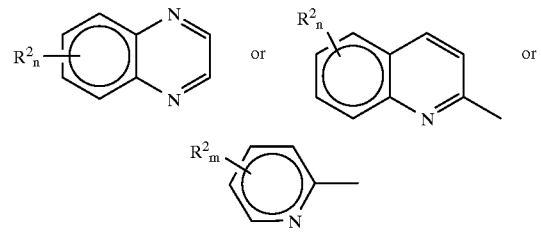

Ar$^2$ may also be preferably substituted or unsubstituted phenyl or naphthyl.

Preferred linkers include non-conjugated flexible linkers such as —NHCH$_2$CH$_2$NH— and —OCH$_2$CH$_2$O—.

Synthesis of the Compounds Useful in the Invention

Many of the compounds useful in the invention are commercially available and can be synthesized by art-known methods. Those compounds useful in the invention which are new compounds, can similarly be obtained by methods generally known in the art.

The following examples are intended to illustrate, but not to limit, the invention.

Preparation A

Compound 59-0008 was synthesized according to the procedure of McDonald, W. S., et al. *Chem Comm* (1969) 392–393; Irving, H. N. N. H. et al. *Anal Chim Acta* (1970) 49:261–266. Briefly, 10.0 g of dithizone was taken up in 100 ml EtOH and 50 ml AcOH and heated at reflux for 18 h. After cooling, this was diluted first with 100 ml water and then with 50 ml 1N NaOH. This was then further neutralized by the addition of 6N NaOH to bring the pH to 5.0. This deep purple mixture was then concentrated on a rotavapor to remove organics. Once the liquid had lost all of its purple color, this was filtered to collect the dark precipitate. Purification by flash chromatography (4.5×25.7 cm; EtAc/Hep.

(1:4); $R_f$ 0.22) followed by recrystalization from EtOH gave 2.15 g (25% yield) of dark purple crystals, mp=184–185° C. $^1$H NMR (CDCl$_3$) 7.90 (d of d, J$_1$=7.7, J$_2$=2.2, 2H), 7.64 (hump, 1H), 7.49 (m, 3H), 7.02 (m, 1H), 6.91 (m, 2H), 6.55 (d, J=8.1, 1H). MS (EI) 254 (47, M+), 105 (26), 77 [100], 51 (27). HRMS (EI, M+) 254.0626 (calcd 254.0626182). Anal. Calcd for C$_{13}$H$_{10}$N$_4$S: C, 61.40; H, 3.96; N, 22.03. Found: C, 61.40; H, 4.20; N, 22.06.

EXAMPLE 1

High Throughput Screening

Several thousand compounds were tested in the assay system set forth in U.S. Serial No. 08/458,434, filed Jun. 2, 1995, and incorporated herein by reference. The standard positive control was a compound of the invention, 59-0008 (also denoted "OS8"), which is of the formula:

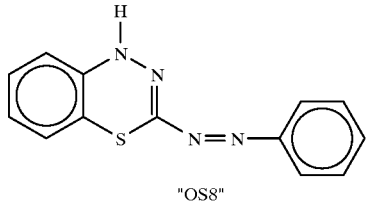

"OS8"

In more detail, the 2T3-BMP-2-LUC cells, a stably transformed osteoblast cell line described in Ghosh-Choudhury et al. *Endocrinology* (1996) 137:331–39, referenced above, was employed. The cells were cultured using α-MEM, 10% FCS with 1% penicillin/streptomycin and 1% glutamine ("plating medium"), and were split 1:5 once per week. For the assay, the cells were resuspended in a plating medium containing 4% FCS, plated in microtiter plates at a concentration of 5×10$^3$ cells (in 50 µl)/well, and incubated for 24 hours at 37° C. in 5% CO$_2$. To initiate the assay, 50 µl of the test compound or the control in DMSO was added at 2× concentration to each well, so that the final volume was 100 µl. The final serum concentration was 2% FCS, and the final DMSO concentration was 1%. Compound 59-0008 (10 µM) was used as a positive control.

The treated cells were incubated for 24 hours at 37° C. and 5% CO$_2$. The medium was then removed, and the cells were rinsed three times with PBS. After removal of excess PBS, 25 µl of 1× cell culture lysing reagent (Promega #E1 53A) was added to each well and incubated for at least ten minutes. Optionally, the plates/samples could be frozen at this point. To each well was added 50 µl of luciferase substrate (Promega #E1 52A; 10 ml Promega luciferase assay buffer per 7 mg Promega luciferase assay substrate). Luminescence was measured on an automated 96-well luminometer, and was expressed as either picograms of luciferase activity per well or as picograms of luciferase activity per microgram of protein.

In this assay, compound 59-0008 (3-phenylazo-1H-4,1,2-benzothiadiazine) exhibited a pattern of reactivity, as shown in FIG. 2. The activity for compound 59-0008 was maximal at a concentration of approximately 3–10 µM and, more particularly, at about 3 µM, and thus provided a response of approximately 175 light emission units. Accordingly, other tested compounds were evaluated at various concentrations, and these results were compared to the results obtained for 59-0008 at 10 µM (which value was normalized to 100). For instance, any tested compound in FIG. 3 and FIG. 4 that showed greater activity than 10 µM of 59-0008 would result in a value over 100.

As shown in FIG. 3 (46 sheets) and FIG. 4 (28 sheets), several compounds were found to be particularly effective.

EXAMPLE 2

In vivo Calvarial Bone Growth Data

Compound 59-0008 was assayed in vivo according to the procedure described previously (see "In vivo Assay of Effects of Compounds on Murine Calvarial Bone Growth", supra). As compared to a vehicle control, compound 59-0008 induced a 4-fold increase in width of new calvarial bone.

EXAMPLE 3

Chondrogenic Activity

Compounds 59-008, 59-0102 and 50-0197 were assayed for effects on the differentiation of cartilage cells, as compared to the action of recombinant human BMP-2. Briefly, a mouse clonal chondrogenic cell line, TMC-23, was isolated and cloned from costal cartilage of transgenic mice containing the BMP-2 gene control region driving SV-40 large T-antigen, generated as described in Ghosh-Choudhury et al *Endocrinology* 137:331–39, 1996. These cells were cultured in DMEM/10% FCS, and were shown to express T-antigen, and also to produce aggrecan (toluidine blue staining at pH 1.0) and Type-II collagen (immunostaining) by 7 days after confluence.

For measurement of alkaline phosphatase (ALP) activity, the technique of LF Bonewald et al. *J Biol Chem* (1992) 267:8943–49, was employed. Briefly, TMC-23 cells were plated in 96 well microtiter plates in DMEM containing 10% FCS at 4×10$^3$ cells/well. Two days after plating, the cells were confluent and the medium was replaced with fresh medium containing 10% FCS and different concentrations of compounds or recombinant BMP-2. After an additional 2 or 5 days incubation, the plates were washed twice with PBS, and then lysing solution (0.05% Triton X-100) was added (100 µl/well). The cells were lysed by three freeze-thaw cycles of –70° C. (30 min), followed by 37° C. (30 min with shaking). Twenty microliters of cell lysates were assayed with 80 µl of 5 mM p-nitrophenol phosphate in 1.5 M 2-amino-2-methyl-propanol buffer, pH 10.3 (Sigma ALP kit, Sigma Chemical Co., St. Louis, Mo.) for 10 min at 37° C. The reaction was stopped by the addition of 100 µl of 0.5 M NaOH. The spectrophotometric absorbance at 405 nm was compared to that of p-nitrophenol standards to estimate ALP activity in the samples. The protein content of the cell lysates was determined by the Bio-Rad protein assay kit (Bio-Rad, Hercules, Calif.). Specific activity was calculated using these two parameters.

At day 2, compounds 59-0008 (10$^{-9}$ M), 59-0102 (10$^{-7}$ M) and 59-0197 (10$^{-9}$ M) increased ALP levels approximately 3-, 2- and 2.5-fold, respectively, as compared to the vehicle control. Recombinant BMP2 at 100, 50 or 10 ng/ml induced ALP levels approximately 10-, 4- or 1.5-fold, respectively, as compared to the vehicle control.

EXAMPLE 4

Synthesis of Exemplary Compounds

A. Exemplary Compound 59-0145 can be synthesized according to the following method. Briefly, a mixture of 2-chloro-5-trifluoromethylpyridine (15 mmol), ethylenediamine (6 mmol), and diisopropylethylamine (18 mmol) was heated at reflux for 18 h. After cooling to room temperature, the solid mass was triturated with dichloromethane. The product was filtered and then suspended in hot EtOAc-:CHCl$_3$ (50:50, 800 mL) and filtered to remove insoluble material. The volume was reduced to ~200 mL by heating on a steam bath. On standing, crystals of pure product were deposited.

Related compounds may be synthesized by reference to the method described for Compound 59-0145, and by reference to the methods described in the following publications: Tzikas, A. & Carisch, C., U.S. Pat. No. 5,393,306, issued Feb. 28, 1995, Herzig, P. & Andreoli, A., EP 580554, published Jan. 26, 1994; Pohlke, R. & Fischer, W., DE 3938561, published May 23, 1991. Analogs containing the structure O—(CH$_2$)$_n$—O may be synthesized by reference to the previous citations, as well as the following publications: Kawato, T. & Newkome, G. *Heterocycles* (1990) 31:1097–104; Kameko, C. & Momose, Y. *Synthesis* (1982) 6:465–66; Tomlin, C. D. S. et al., GB 1161492, published Aug. 13, 1969.

B. Exemplary Compound 59-0097 and exemplary Compound 59-0201 were synthesized according to the following general procedure. Briefly, the isothiocyanate or isocyanate (1 mmol) was dissolved in 5 mL of anhydrous DMF in a vial and the solution was stirred at room temperature (RT). Diisopropylethyamine (2 mmol) was added dropwise to the above stirred solution followed by 3-hydrazinobenzoic acid (1 mmol), and the mixture was stirred overnight at RT. It was then diluted with 50 mL of cold water with vigorous stirring. The precipitate was collected by filtration, washed thoroughly with water several times, and then dried in vacuo overnight. The product was purified by flash column chromatography over silica gel eluting with 5% methanol in dichloromethane. The pure product was obtained as a red to purple powder. The compounds of the invention are produced by substituting for at least one phenyl group the appropriate heterocycle.

We claim:

1. A method to treat a condition in a vertebrate animal characterized by a deficiency in, or need for, bone growth replacement and/or an undesirable level of bone resorption, which method comprises administering to a vertebrate subject in need of such treatment an effective amount of a compound of the formula:

(1)

[Ar$^1$]

wherein each R$^1$ is independently a non-interfering substituent;

m is an integer of 0–5;

each Z is independently N or CR, where R is H or alkyl (1–6C), with the proviso that at least one Z must be a heteroatom and at least one Z must be CR;

L is a linker; and

Ar$^2$ is a substituted or unsubstituted phenyl, a substituted or unsubstituted naphthyl, a substituted or unsubstituted aromatic system containing a 6-membered heterocycle, or a substituted or unsubstituted aromatic system containing a 5-membered heterocycle.

2. The method of claim 1 wherein L is a flexible conjugating or nonconjugating linker.

3. The method of claim 2 wherein L is a nonconjugating linker.

4. The method of claim 3 wherein L is selected from the group consisting of NRCR$_2$CR$_2$NR, OCR$_2$CR$_2$O, where each R is independently H or alkyl (1–6C).

5. The method of claim 1 wherein Ar$^2$ is where R$^2$ is a non-interfering substituent and Z and m are as defined in claim 1.

6. The method of claim 5 wherein the compound of formula 1 is of the formula

7. The method of claim 1 wherein said condition is osteoporosis, bone fracture or deficiency, primary or secondary hyperparathyroidism, periodontal disease or defect, metastatic bone disease, osteolytic bone disease, post-plastic surgery, post-prosthetic joint surgery, or post-dental implantation.

8. The method of claim 1 which further comprises administering to said subject one or more agents that promote bone growth or that inhibit bone resorption.

9. The method of claim 8 wherein said agents are selected from the group consisting of bone morphogenetic factors, anti-resorptive agents, osteogenic factors, cartilage-derived morphogenic proteins, growth hormones, and differentiating factors.

10. A method to treat a condition in a vertebrate animal characterized by a deficiency in, or need for, bone growth replacement and/or an undesirable level of bone resorption, which method comprises administering to a vertebrate subject in need of such treatment an effective amount of a compound of the formula:

(2)

(3)

wherein each R$^1$ and R$^2$ is independently a non-interfering substituent;

m is an integer of 0–5; and

L is a linker.

11. The method of claim 10 wherein L is a flexible conjugating or nonconjugating linker.

12. The method of claim 11 wherein L is a nonconjugating linker.

13. The method of claim 12 wherein L is selected from the group consisting of $NRCR_2CR_2NR$, $OCR_2CR_2O$, where each R is independently H or alkyl (1–6C).

14. The method of claim 13 wherein each of $R^1$ and $R^2$ is independently alkyl (1–6C), alkenyl (1–6C), alkynyl (1–6C), each of which may optionally be substituted; halogen, siloxy, OR, SR, $NR_2$, OOCR, COOR, NCOR, NCOOR, benzoyl, $CF_3$, $OCF_3$, $SCF_3$, $N(CF_3)_2$, CN, SO, $SO_2R$, or $SO_3R$ wherein R is H or alkyl (1–6C).

15. The method of claim 14 wherein each m is independently 0, 1 or 2.

* * * * *